(12) United States Patent
Qiu et al.

(10) Patent No.: US 12,083,227 B2
(45) Date of Patent: *Sep. 10, 2024

(54) SOLID PHARMACEUTICAL FORMULATIONS FOR TREATING ENDOMETRIOSIS, UTERINE FIBROIDS, POLYCYSTIC OVARY SYNDROME OR ADENOMYOSIS

(71) Applicants: AbbVie Inc., North Chicago, IL (US); Neurocrine Biosciences, Inc., San Diego, CA (US)

(72) Inventors: Yihong Qiu, North Chicago, IL (US); Yuchuan Gong, North Chicago, IL (US); Alexander Ruggles, Lake Forest, IL (US); Jared A. Baird, Grayslake, IL (US); Hui Zu, North Chicago, IL (US); Gregory A. McClelland, San Diego, CA (US); Anna V. Stepanenko, Del Mar, CA (US)

(73) Assignees: AbbVie Inc., North Chicago, IL (US); Neurocrine Biosciences, Inc., San Diego, CA (US)

( * ) Notice: Subject to any disclaimer, the term of this patent is extended or adjusted under 35 U.S.C. 154(b) by 418 days.

This patent is subject to a terminal disclaimer.

(21) Appl. No.: 16/105,440

(22) Filed: Aug. 20, 2018

(65) Prior Publication Data
US 2019/0054027 A1 Feb. 21, 2019

Related U.S. Application Data

(60) Provisional application No. 62/547,410, filed on Aug. 18, 2017, provisional application No. 62/660,104, filed on Apr. 19, 2018.

(51) Int. Cl.
A61K 9/20 (2006.01)
A61K 31/513 (2006.01)
A61P 15/00 (2006.01)

(52) U.S. Cl.
CPC .......... *A61K 9/2031* (2013.01); *A61K 9/2009* (2013.01); *A61K 9/2013* (2013.01); *A61K 9/2027* (2013.01); *A61K 31/513* (2013.01); *A61P 15/00* (2018.01)

(58) Field of Classification Search
CPC .. A61K 9/2031; A61K 31/513; A61K 9/2009; A61K 9/2013; A61K 9/2027; A61P 15/00
See application file for complete search history.

(56) References Cited

U.S. PATENT DOCUMENTS

| | | |
|---|---|---|
| 4,311,606 A | 1/1982 | Kaeser |
| 4,800,035 A | 1/1989 | Broze et al. |
| 6,054,482 A | 4/2000 | Augart et al. |
| 6,323,193 B1 | 11/2001 | Somani et al. |
| 6,521,256 B2 | 2/2003 | Makino et al. |
| 7,056,927 B2 | 6/2006 | Guo et al. |
| 7,176,211 B2 | 2/2007 | Guo et al. |
| 7,419,983 B2 | 9/2008 | Guo et al. |
| 8,765,948 B2 | 7/2014 | Gallagher et al. |
| 8,969,379 B2 | 3/2015 | Furitsu et al. |
| 9,382,214 B2 | 7/2016 | Gallagher et al. |
| 9,687,453 B2 | 6/2017 | Uchida et al. |
| 9,868,706 B2 | 1/2018 | Gallagher et al. |
| 9,949,974 B2 | 4/2018 | Goss et al. |
| 10,350,170 B2 | 7/2019 | Yamane et al. |
| 2003/0143276 A1* | 7/2003 | Hsia ............... A61K 9/2054 514/178 |
| 2005/0271717 A1 | 12/2005 | Berchielli et al. |
| 2006/0057207 A1* | 3/2006 | Ziegler ............ A61K 9/2866 424/484 |
| 2009/0280169 A1 | 11/2009 | Leonard |
| 2009/0280170 A1 | 11/2009 | Lee et al. |
| 2011/0281929 A1* | 11/2011 | Cuypers ............ A61K 9/205 514/424 |
| 2012/0165386 A1 | 6/2012 | Agarwal et al. |
| 2013/0224296 A1* | 8/2013 | Narang ............ A61K 9/2009 514/23 |
| 2014/0271872 A1 | 9/2014 | Pham et al. |
| 2015/0164917 A1* | 6/2015 | Valducci ........... A61K 9/2095 514/179 |
| 2016/0008777 A1* | 1/2016 | Patel ............... B01F 13/0052 424/94.67 |
| 2016/0354315 A1 | 12/2016 | Li |
| 2017/0007600 A1* | 1/2017 | Gao ................ A61K 9/1688 |
| 2017/0056403 A1 | 3/2017 | Goss et al. |

(Continued)

FOREIGN PATENT DOCUMENTS

CN 100572491 C 12/2009
CN 106619547 A 5/2017

(Continued)

OTHER PUBLICATIONS

Co-pending U.S. Appl. No. 15/174,774, filed Jun. 6, 2016.
International Search Report and Written Opinion for Application No. PCT/US2018/47072, mailed Nov. 19, 2018, 11 pages.
International Search Report and Written Opinion for Application No. PCT/US2018/47073, mailed on Nov. 1, 2018, 16 pages.
The Menorrhagia Research Group, "Quantification of Menstrual Blood Loss.," The Obstetrician & Gynaecologist., 2004, vol. 6, pp. 88-92.
Desai Ujwala et al.: "Melt granulation: an alternative to traditional granulation techniques" Indian Drugs, vol. 50, No. 3, p. 5-13, Mar. 31, 2013.

(Continued)

*Primary Examiner* — Aradhana Sasan
(74) *Attorney, Agent, or Firm* — Neal, Gerber & Eisenberg LLP

(57) ABSTRACT

The present disclosure relates to pharmaceutical compositions comprising a gonadotropin-releasing hormone (GnRH) antagonist and methods of preparing and using such compositions. The disclosure also relates to methods of facilitating release of a GnRH antagonist from a pharmaceutical composition.

46 Claims, 15 Drawing Sheets

(56) References Cited

U.S. PATENT DOCUMENTS

| | | | |
|---|---|---|---|
| 2018/0235963 | A1 | 8/2018 | Goss et al. |
| 2018/0346428 | A1 | 12/2018 | Gallagher et al. |
| 2019/0054088 | A1* | 2/2019 | Jayanth ............ A61K 9/2018 |
| 2019/0218191 | A1 | 7/2019 | Gallagher et al. |
| 2020/0255387 | A1 | 8/2020 | Gallagher et al. |

FOREIGN PATENT DOCUMENTS

| | | | |
|---|---|---|---|
| CN | 108129400 A | | 6/2018 |
| CN | 108586359 A | | 9/2018 |
| JP | 2002326960 A | | 11/2002 |
| WO | WO-9944614 A1 | | 9/1999 |
| WO | WO-0121194 A2 | | 3/2001 |
| WO | WO-0155119 A2 | | 8/2001 |
| WO | WO-0211732 A1 | | 2/2002 |
| WO | WO-02061931 A1 | | 8/2002 |
| WO | WO-03101431 A1 | | 12/2003 |
| WO | WO-2004014356 A1 | | 2/2004 |
| WO | WO-2004032905 A1 | | 4/2004 |
| WO | WO-2005007165 A1 | | 1/2005 |
| WO | WO-2005020978 A1 | | 3/2005 |
| WO | WO-2005077332 A2 | | 8/2005 |
| WO | WO-2006057507 A1 | | 6/2006 |
| WO | WO-2007107835 A2 | | 9/2007 |
| WO | WO-2007128495 A2 | | 11/2007 |
| WO | 2009137078 A1 | | 11/2009 |
| WO | 2011131601 A1 | | 10/2011 |
| WO | WO-2014143669 A1 | | 9/2014 |
| WO | 2016136849 A1 | | 9/2016 |
| WO | WO-2017022144 A1 | | 2/2017 |
| WO | WO-2017221144 A1 | | 12/2017 |
| WO | WO-2018189212 A1 | | 10/2018 |
| WO | WO-2018189213 A1 | | 10/2018 |
| WO | WO-2018198086 A1 | | 11/2018 |
| WO | WO-2018224063 A2 | | 12/2018 |
| WO | WO-2020020999 A1 | | 1/2020 |
| WO | WO-2020043763 A1 | | 3/2020 |

OTHER PUBLICATIONS

Repka Michael A.: et al. "Applications of hot-melt extrusion for drug delivery", Expert opinion on drug delivery, vol. 5, No. 12, p. 1357-1376, Dec. 31, 2008.

Bai Xue-qian et al., "Application of microenvironmental pH modified technology in solid dispersions," Chinese Journal of New Drugs, 2011, vol. 20(20), pp. 1957-1965, abstract only.

Co-pending U.S. Appl. No. 16/105,396, filed Aug. 20, 2018.

Co-pending U.S. Appl. No. 16/739,263, filed Jan. 10, 2020.

Taylor H.S. et al., "Treatment of Endometriosis-Associated Pain with Elagolix, an Oral GnRH Antagonist", The New England Journal of Medicine, vol. 377, No. 1, Jul. 6, 2017 (Jul. 6, 2017), pp. 28-40.

Archer D.F., et al., "Elagolix for the Management of Heavy Menstrual Bleeding Associated with Uterine Fibroids: Results from a Phase 2a Proof-of-Concept Study," Fertility and Sterility. 2017, vol. 108(1), pp. 152-160.

Badawy, Sherif I. Farag, and Munir A. Hussain. "Microenvironmental pH modulation in solid dosage forms." Journal of Pharmaceutical Sciences 96.5 (2007): 948-959.

Bass N.M., et al., "Guide to Drug Dosage in Hepatic Disease," Clinical Pharmacokinetics, 1988, vol. 15, pp. 396-420.

Carr B., et al., "Elagolix, an Oral GnRH Antagonist, Versus Subcutaneous Depot Medroxyprogesterone Acetate for the Treatment of Endometriosis: Effects on Bone Mineral Density," Reproductive Sciences, 2014, vol. 21 (11), pp. 1341-1351.

Extended European Search Report for European Application No. 18847001.7 dated Apr. 12, 2021, 6 pages.

Hughey, et al., European Journal of Pharmaceutical Sciences, 48(4-5), 758-766 (2016).

Melis G.B., et al., "Overview of Elagolix for the Treatment of Endometriosis," Expert Opinion on Drug Metabolism & Toxicology, 2016, vol. 12 (5), pp. 581-588.

Mohr M.E., "Standards of Practice for the Pharmacy Technician," Lippincott Williams & Wilkins, Chapter 8, 2010.

Rajaabai-Siahboomi, Ali R., et al. "Excipient Selection in Oral Solid Dosage Formulations Containing Moisture Sensitive Drugs." Excipient Applications in Formulation Design and Drug Delivery. Springer, Cham, 385-421, (2015).

Rowe R.C., "Handbook of Pharmaceutical Excipients," Pharmaceutical Press, 2009.

Schwartz M., et al., "Strategies for the Management of Hepatocellular Carcinoma," Nature Clinical Practice Oncology, 2007, vol. 4, pp. 424-432.

Struthers R.S. et al., "Suppression of Gonadotropins and Estradiol in Premenopausal Women by Oral Administration of the Nonpeptide Gonadotropin-Releasing Hormone Antagonist Elagolix," The Journal of Clinical Endocrinology & Metabolism, 2009, vol. 94 (2), pp. 545-551.

Verbeeck R.K., "Pharmacokinetics and Dosage Adjustment in Patients with Hepatic Dysfunction," European Journal of Clinical Pharmacology, 2008, vol. 64, pp. 1147-1161.

Anticancer Drugs that Inhibit Hormone Action, Medicinal Chemistry of Anticancer Drugs, 2008, Elsevier B. V., p. 53-91, dated 2008.

Mohamed Sabry et al., Innovative Oral Treatments of Uterine Leiomyoma, Obstetrics and Gynecology International, vol. 2012, Article ID 943635, dated Aug. 17, 2011.

Federal Register, Jan. 5, 2001, vol. 66(4), pp. 1099-1111.

Extended European Search Report for Application No. EP19845569, mailed on May 6, 2022, 4 pages.

* cited by examiner

BOXES REPRESENT MEDIAN (SOLID BOLD LINE) WITH 25% AND 75% QUARTILES; WHISKERS ARE MINIMUM AND MAXIMUM VALUES. THE STIPPLED LINES REPRESENT Z-SCORE THRESHOLDS OF +1 AND -1 (BLACK) AND THE DOT AND DASHED LINES REPRESENT Z-SCORE THRESHOLDS OF +2 AND -2 (GREY).

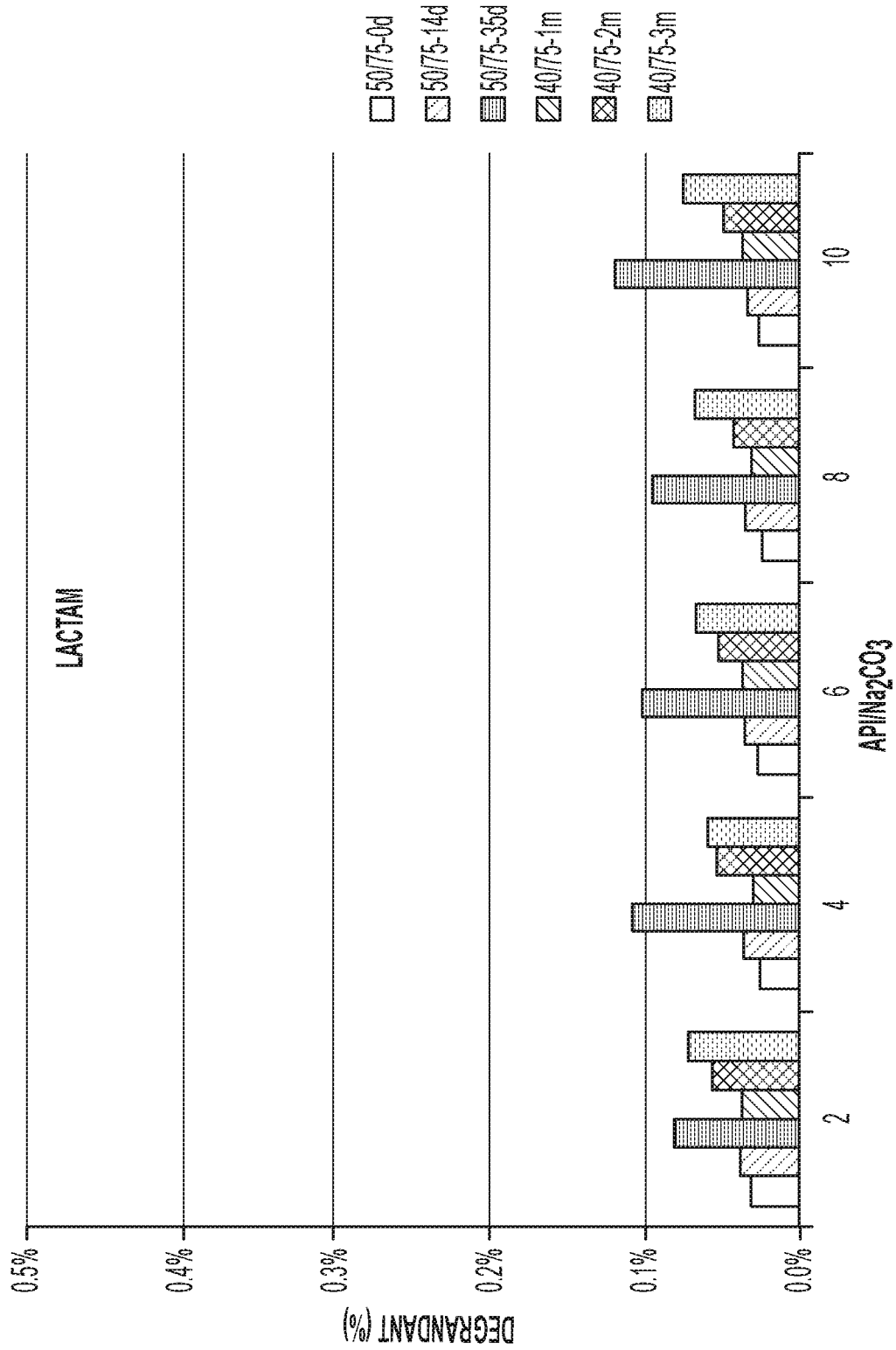
FIG. 10 contiuned

SOLID PHARMACEUTICAL FORMULATIONS FOR TREATING ENDOMETRIOSIS, UTERINE FIBROIDS, POLYCYSTIC OVARY SYNDROME OR ADENOMYOSIS

RELATED APPLICATIONS

The present application seeks priority from provisional application 62/547,410 filed on Aug. 18, 2017, provisional application 62/660,104 filed on Apr. 19, 2018, and non-provisional application PCT/US2018/043321, filed on Jul. 23, 2018, all of which are incorporated herein by reference in its entirety for all purposes.

TECHNICAL FIELD

The present invention relates to pharmaceutical compositions of elagolix or elagolix sodium or Compound A, or pharmaceutically acceptable salts thereof, and methods of use of such compositions.

BACKGROUND

Endometriosis is a disease in which tissue normally found in the uterine cavity (i.e., endometrium) is found outside the uterus, usually implanted on the peritoneal lining of the pelvis. Endometriosis affects an estimated 1 in 10 women of reproductive age and can cause pain, infertility, and sexual dysfunction. Growth of endometrial tissue outside of the uterine cavity is believed to be estrogen-dependent.

Uterine fibroids (leiomyomas) are benign tumors and are highly prevalent in women of reproductive age. Symptoms associated with uterine fibroids most commonly include heavy or prolonged menstrual bleeding, pelvic pressure and pelvic organ compression, back pain, and adverse reproductive outcomes. Heavy menstrual bleeding (HMB; menorrhagia, defined as greater than 80 mL per menstrual cycle) (The Menorrhagia Research Group. Quantification of menstrual blood loss. The Obstetrician & Gynaecologist. 2004; 6:88-92) is inconvenient and may lead to iron-deficiency anemia, which is the leading cause of surgical interventions that may include hysterectomy. Other symptoms, in particular pressure symptoms, are largely dependent on the size, number, and location of the tumors.

Although the pathogenesis has yet to be fully elucidated, the growth of uterine fibroids is known to be highly dependent on both estrogen and progestogen. Fibroids tend to shrink after menopause due to a decrease in hormone production.

Adenomyosis is a condition in which the inner lining of the uterus (the endometrium) breaks through the muscle wall of the uterus (the myometrium). Adenomyosis can cause menstrual cramps, lower abdominal pressure, and bloating before menstrual periods and can result in heavy periods. The condition can be located throughout the entire uterus or localized in one spot. Adenomyosis is a common condition. It is most often diagnosed in middle-aged women and women who have had children. Some studies also suggest that women who have had prior uterine surgery may be at risk for adenomyosis. Menorrhagia and intermenstrual bleeding are the most common complains, followed by pain, especially menstrual pain, and bladder and rectal pressure. Only surgery (myomectomy or hysterectomy) is regarded as curative.

Polycystic ovary syndrome (PCOS) is a hormonal disorder common among women of reproductive age. Women with PCOS may have infrequent or prolonged menstrual periods or excess male hormone (androgen) levels. The ovaries may develop numerous small collections of fluid (follicles) and fail to regularly release eggs.

Thus, there is a need in the art for new orally administered treatments for endometriosis, uterine fibroids, PCOS and adenomyosis and, in particular, management of pain associated with endometriosis, uterine fibroids, PCOS or adenomyosis and heavy menstrual bleeding associated with endometriosis, uterine fibroids, PCOS or adenomyosis. Moreover, there remains a need in the art to develop orally bioavailable dosage forms comprising such treatments and, in particular, a nonpeptide GnRH antagonist.

SUMMARY OF THE INVENTION

The disclosure is directed to solid pharmaceutical compositions comprising 4-((R)-2-[5-(2-fluoro-3-methoxy-phenyl)-3-(2-fluoro-6-trifluoromethyl-benzyl)-4-methyl-2,6-dioxo-3,6-dihydro-2H-pyrimidin-1-yl]-1-phenyl-ethylamino)-butyric acid (Compound A) or a pharmaceutically acceptable salt thereof; methods of using such compositions; and methods of achieving a high drug load of Compound A or a pharmaceutically acceptable salt thereof in such compositions.

The present application provides solid pharmaceutical compositions comprising a high drug load of Compound A or a pharmaceutically acceptable salt thereof. In certain embodiments, such compositions are manufactured by melt-processing. Conventional melt-processing utilizes compositions comprising at least 10% (w/w) of a binder. Thus, conventional melt-processing limits the amount of API and/or additional excipients that can be included in the composition. It has been determined in the present application that Compound A or a pharmaceutically acceptable salt thereof and, in particular, sodium 4-((R)-2-[5-(2-fluoro-3-methoxy-phenyl)-3-(2-fluoro-6-trifluoromethyl-benzyl)-4-methyl-2,6-dioxo-3,6-dihydro-2H-pyrimidin-1-yl]-1-phenyl-ethylamino)butanoate is miscible with a pharmaceutically acceptable meltable binder, such as polyethylene glycol (PEG). The miscibility of PEG and sodium 4-((R)-2-[5-(2-fluoro-3-methoxy-phenyl)-3-(2-fluoro-6-trifluoromethyl-benzyl)-4-methyl-2,6-dioxo-3,6-dihydro-2H-pyrimidin-1-yl]-1-phenyl-ethylamino)butanoate is one factor that allows the formulation to be processed with less polymer, such as PEG than a conventional melt-processed formulation. Thus, in certain aspects, the present application provides high drug load compositions comprising an active pharmaceutical ingredient (API), preferably sodium 4-((R)-2-[5-(2-fluoro-3-methoxy-phenyl)-3-(2-fluoro-6-trifluoromethyl-benzyl)-4-methyl-2,6-dioxo-3,6-dihydro-2H-pyrimidin-1-yl]-1-phenyl-ethylamino)butanoate and less than about 10% (w/w) of a pharmaceutically acceptable meltable binder. In other aspects, the present application provides a single-phase system comprising amorphous sodium 4-((R)-2-[5-(2-fluoro-3-methoxy-phenyl)-3-(2-fluoro-6-trifluoromethyl-benzyl)-4-methyl-2,6-dioxo-3,6-dihydro-2H-pyrimidin-1-yl]-1-phenyl-ethylamino)butanoate miscible with a binder in a solid matrix. In still other aspects, the present application provides a multi-phase system comprising amorphous sodium 4-((R)-2-[5-(2-fluoro-3-methoxy-phenyl)-3-(2-fluoro-6-trifluoromethyl-benzyl)-4-methyl-2,6-dioxo-3,6-dihydro-2H-pyrimidin-1-yl]-1-phenyl-ethylamino) butanoate molecularly dispersed in a solid matrix and amorphous sodium 4-((R)-2-[5-(2-fluoro-3-methoxy-phenyl)-3-(2-fluoro-6-trifluoromethyl-benzyl)-4-methyl-2,6-dioxo-3,6-dihydro-2H-pyrimidin-1-yl]-1-phenyl-ethylamino)

butanoate particles or clusters mixed with the solid matrix. In still other aspects, the present application provides a multi-phase system comprising a binder that is molecularly dispersed in a solid matrix containing amorphous sodium 4-((R)-2-[5-(2-fluoro-3-methoxy-phenyl)-3-(2-fluoro-6-trifluoromethyl-benzyl)-4-methyl-2,6-dioxo-3,6-dihydro-2H-pyrimidin-1-yl]-1-phenyl-ethylamino)butanoate and amorphous sodium 4-((R)-2-[5-(2-fluoro-3-methoxy-phenyl)-3-(2-fluoro-6-trifluoromethyl-benzyl)-4-methyl-2,6-dioxo-3, 6-dihydro-2H-pyrimidin-1-yl]-1-phenyl-ethylamino) butanoate particles or clusters mixed with the solid matrix. In still other aspects, the present application provides a multi-phase system comprising a binder that is dispersed in a solid matrix containing amorphous sodium 4-((R)-2-[5-(2-fluoro-3-methoxy-phenyl)-3-(2-fluoro-6-trifluoromethyl-benzyl)-4-methyl-2,6-dioxo-3,6-dihydro-2H-pyrimidin-1-yl]-1-phenyl-ethylamino)butanoate and amorphous sodium 4-((R)-2-[5-(2-fluoro-3-methoxy-phenyl)-3-(2-fluoro-6-trifluoromethyl-benzyl)-4-methyl-2,6-dioxo-3,6-dihydro-2H-pyrimidin-1-yl]-1-phenyl-ethylamino)butanoate particles or clusters mixed with the solid matrix. In still other aspects, the present application provides a multi-phase system comprising a binder that is dispersed in a solid matrix containing amorphous sodium 4-((R)-2-[5-(2-fluoro-3-methoxy-phenyl)-3-(2-fluoro-6-trifluoromethyl-benzyl)-4-methyl-2,6-dioxo-3,6-dihydro-2H-pyrimidin-1-yl]-1-phenyl-ethylamino)butanoate and one or more excipients mixed with the solid matrix. In still other aspects, the present application provides a multi-phase system comprising a binder mixed with amorphous sodium 4-((R)-2-[5-(2-fluoro-3-methoxy-phenyl)-3-(2-fluoro-6-trifluoromethyl-benzyl)-4-methyl-2,6-dioxo-3,6-dihydro-2H-pyrimidin-1-yl]-1-phenyl-ethylamino)butanoate dispersed in a solid matrix. In yet other aspects, the present application provides a multi-phase system comprising a binder mixed with amorphous sodium 4-((R)-2-[5-(2-fluoro-3-methoxy-phenyl)-3-(2-fluoro-6-trifluoromethyl-benzyl)-4-methyl-2,6-dioxo-3,6-dihydro-2H-pyrimidin-1-yl]-1-phenyl-ethylamino)butanoate dispersed in a solid matrix containing one or more excipients.

The present application provides high drug load compositions comprising an active pharmaceutical ingredient (API), preferably sodium 4-((R)-2-[5-(2-fluoro-3-methoxy-phenyl)-3-(2-fluoro-6-trifluoromethyl-benzyl)-4-methyl-2,6-dioxo-3,6-dihydro-2H-pyrimidin-1-yl]-1-phenyl-ethylamino)butanoate and, more preferably, amorphous sodium 4-((R)-2-[5-(2-fluoro-3-methoxy-phenyl)-3-(2-fluoro-6-trifluoromethyl-benzyl)-4-methyl-2,6-dioxo-3,6-dihydro-2H-pyrimidin-1-yl]-1-phenyl-ethylamino)butanoate. Typically, a high drug load may require large dosage forms, especially if the compound has low compressibility. Such large dosage forms are associated with poor patient compliance (e.g., due to difficulty in swallowing). The physical properties, such as bulk density and particle size, of amorphous sodium 4-((R)-2-[5-(2-fluoro-3-methoxy-phenyl)-3-(2-fluoro-6-trifluoromethyl-benzyl)-4-methyl-2,6-dioxo-3,6-dihydro-2H-pyrimidin-1-yl]-1-phenyl-ethylamino)butanoate may vary from batch to batch. API with low bulk density may have poor flow properties, which present challenges in blending and compression. Known techniques for working with API having poor flow properties (e.g., dry granulation or roller compaction) often compromise the compressibility of the formulation. Thus, in certain aspects, the present application provides solid pharmaceutical compositions, and methods of making such compositions, having a high drug load yet maintain sufficient compressibility to achieve a suitable dosage form (e.g., a tablet with a total weight less than about 2 g, preferably less than about 1.6 g).

In one aspect, the disclosed solid pharmaceutical compositions comprise Compound A or a pharmaceutically acceptable salt thereof molecularly dispersed in a solid matrix, such as solid dispersion.

In one aspect, the disclosed solid pharmaceutical compositions comprise Compound A or a pharmaceutically acceptable salt thereof dispersed in a solid matrix.

In certain embodiments, the salt of Compound A is the monosodium salt (sodium 4-((R)-2-[5-(2-fluoro-3-methoxy-phenyl)-3-(2-fluoro-6-trifluoromethyl-benzyl)-4-methyl-2,6-dioxo-3,6-dihydro-2H-pyrimidin-1-yl]-1-phenyl-ethylamino)butanoate). In certain embodiments, Compound A or a pharmaceutically acceptable salt thereof is amorphous sodium 4-((R)-2-[5-(2-fluoro-3-methoxy-phenyl)-3-(2-fluoro-6-trifluoromethyl-benzyl)-4-methyl-2,6-dioxo-3,6-dihydro-2H-pyrimidin-1-yl]-1-phenyl-ethylamino)butanoate.

In certain embodiments, the solid matrix, such as solid dispersion further comprises at least one additional excipient, such as a pharmaceutically acceptable meltable binder.

In certain embodiments, the solid matrix, such as solid dispersion comprises a pharmaceutically acceptable meltable binder. In some such embodiments, the pharmaceutically acceptable meltable binder is polyalkylene glycol, such as polyethylene glycol (PEG). In some such embodiments, the pharmaceutically acceptable meltable binder is PEG 3350.

In certain embodiments, the solid pharmaceutical composition is prepared by melt granulation. In certain embodiments, a product, such as an extrudate prepared by melt extrusion, is cut or milled into granules.

In certain embodiments, the solid pharmaceutical composition further comprises a disintegrant. In some such embodiments, the disintegrant is a cross-linked polymer. In some such embodiments, the disintegrant is crospovidone.

In certain embodiments, the solid pharmaceutical composition further comprises a glidant. In some such embodiments, the glidant is colloidal silicon dioxide.

In certain embodiments, the solid pharmaceutical composition further comprises a pH modifying agent, or properties thereof, such as a pH modifying agent. In some such embodiments, the pH modifying agent is an alkali or alkaline earth metal hydroxide (e.g., sodium hydroxide, calcium hydroxide, magnesium hydroxide, aluminum hydroxide) or an alkali or alkaline earth metal salt (e.g., sodium acetate, sodium bicarbonate, sodium carbonate, sodium hydrogen carbonate, sodium phosphate, potassium carbonate, potassium hydrogen carbonate, potassium phosphate, magnesium acetate, magnesium bicarbonate, magnesium carbonate, magnesium phosphate, and the like) or weak bases with pKa ≥6 including amino acid bases or weak polymeric bases (eg, alanine, lysine, arginine, amino methacrylate copolymer, etc.).

In some such embodiments, the pH modifying agent is sodium carbonate, such as sodium carbonate monohydrate or sodium carbonate anhydrous.

In certain embodiments, the solid pharmaceutical composition comprises a solid matrix, such as solid dispersion comprising Compound A or a pharmaceutically acceptable salt thereof and a pharmaceutically acceptable meltable binder; and the solid pharmaceutical composition further comprises Compound A or a pharmaceutically acceptable salt thereof mixed with the solid matrix, such as solid dispersion. In some such embodiments, the solid pharmaceutical composition comprises a two-phase system wherein Compound A or a pharmaceutically acceptable salt thereof is miscible with the binder in the solid matrix, such as in the solid dispersion and Compound A or a pharmaceutically acceptable salt thereof is mixed with the solid dispersion. In some such embodiments, the solid pharmaceutical composition comprises a two-phase system wherein sodium 4-((R)-2-[5-(2-fluoro-3-methoxy-phenyl)-3-(2-fluoro-6-trifluoromethyl-benzyl)-4-methyl-2,6-dioxo-3,6-dihydro-2H-pyrimidin-1-yl]-1-phenyl-ethylamino)butanoate is molecularly dispersed in a solid matrix, such as a solid dispersion and additional sodium 4-((R)-2-[5-(2-fluoro-3-methoxy-phenyl)-3-(2-fluoro-6-trifluoromethyl-benzyl)-4-methyl-2,6-dioxo-3,6-dihydro-2H-pyrimidin-1-yl]-1-phenyl-ethylamino)butanoate is mixed with the solid matrix. In some such embodiments, the solid pharmaceutical composition comprises a two-phase system wherein amorphous sodium 4-((R)-2-[5-(2-fluoro-3-methoxy-phenyl)-3-(2-fluoro-6-trifluoromethyl-benzyl)-4-methyl-2,6-dioxo-3,6-dihydro-2H-pyrimidin-1-yl]-1-phenyl-ethylamino)butanoate is molecularly dispersed in the solid matrix, such as solid dispersion and additional amorphous sodium 4-((R)-2-[5-(2-fluoro-3-methoxy-phenyl)-3-(2-fluoro-6-trifluoromethyl-benzyl)-4-methyl-2,6-dioxo-3,6-dihydro-2H-pyrimidin-1-yl]-1-phenyl-ethylamino)butanoate is mixed with the solid matrix. In certain embodiments, the solid pharmaceutical composition comprises Compound A or a pharmaceutically acceptable salt thereof in an amount of about 100 mg to about 400 mg; and from about 1% to about 20% by weight, preferably from about 2% to about 10% by weight, more preferably from about 4% to about 6% of a pharmaceutically acceptable meltable binder. In some such embodiments, the pharmaceutically acceptable meltable binder is polyethylene glycol (PEG), such as PEG 3350.

The disclosure is also directed to solid pharmaceutical compositions comprising an amount of Compound A or a pharmaceutically acceptable salt thereof and at least one pharmaceutically acceptable meltable binder, and, optionally, a disintegrant and/or a glidant.

In certain embodiments, Compound A or a pharmaceutically acceptable salt thereof is present in the solid pharmaceutical composition in an amount from about 20% to about 90% by weight, preferably from about 35% by weight to about 80%, preferably from about 50% by weight to about 70%, and more preferably from about 55% to about 60% of the solid pharmaceutical composition.

In certain embodiments, the amount of Compound A or a pharmaceutically acceptable salt thereof is from about 175 mg to about 225 mg, alternatively from about 190 mg to about 210 mg, and preferably about 200 mg. In certain embodiments, the amount of Compound A or a pharmaceutically acceptable salt thereof is from about 275 mg to about 325 mg, alternatively from about 290 mg to about 310 mg, and preferably about 300 mg.

In certain embodiments, the salt of Compound A is the monosodium salt (sodium 4-((R)-2-[5-(2-fluoro-3-methoxy-phenyl)-3-(2-fluoro-6-trifluoromethyl-benzyl)-4-methyl-2,6-dioxo-3,6-dihydro-2H-pyrimidin-1-yl]-1-phenyl-ethylamino)butanoate). In certain embodiments, Compound A or a pharmaceutically acceptable salt thereof is amorphous sodium 4-((R)-2-[5-(2-fluoro-3-methoxy-phenyl)-3-(2-fluoro-6-trifluoromethyl-benzyl)-4-methyl-2,6-dioxo-3,6-dihydro-2H-pyrimidin-1-yl]-1-phenyl-ethylamino)butanoate.

In certain embodiments, the pharmaceutically acceptable meltable binder is miscible with Compound A or the pharmaceutically acceptable salt thereof.

In certain embodiments, at least a first portion of the amount of Compound A or the pharmaceutically acceptable salt thereof is miscible with a binder in a solid matrix, wherein the solid matrix comprises the pharmaceutically acceptable meltable binder. In certain embodiments, a second portion of the amount of Compound A or a pharmaceutically acceptable salt thereof is mixed with the solid matrix. In some such embodiments, the solid pharmaceutical composition comprises a first portion of the amount of Compound A or a pharmaceutically acceptable salt thereof molecularly dispersed in the solid matrix and a second portion of the amount of Compound A or a pharmaceutically acceptable salt thereof mixed with the solid matrix. In some such embodiments, the solid pharmaceutical composition comprises sodium 4-((R)-2-[5-(2-fluoro-3-methoxy-phenyl)-3-(2-fluoro-6-trifluoromethyl-benzyl)-4-methyl-2,6-dioxo-3,6-dihydro-2H-pyrimidin-1-yl]-1-phenyl-ethylamino)butanoate molecularly dispersed in the solid matrix and sodium 4-((R)-2-[5-(2-fluoro-3-methoxy-phenyl)-3-(2-fluoro-6-trifluoromethyl-benzyl)-4-methyl-2,6-dioxo-3,6-dihydro-2H-pyrimidin-1-yl]-1-phenyl-ethylamino)butanoate mixed with the solid matrix. In some such embodiments, the solid pharmaceutical composition comprises amorphous sodium 4-((R)-2-[5-(2-fluoro-3-methoxy-phenyl)-3-(2-fluoro-6-trifluoromethyl-benzyl)-4-methyl-2,6-dioxo-3,6-dihydro-2H-pyrimidin-1-yl]-1-phenyl-ethylamino)butanoate molecularly dispersed in the solid matrix and amorphous sodium 4-((R)-2-[5-(2-fluoro-3-methoxy-phenyl)-3-(2-fluoro-6-trifluoromethyl-benzyl)-4-methyl-2,6-dioxo-3,6-dihydro-2H-pyrimidin-1-yl]-1-phenyl-ethylamino)butanoate mixed with the solid matrix.

In certain embodiments, the solid matrix comprises a pharmaceutically acceptable meltable binder. In some such embodiments, the pharmaceutically acceptable meltable binder is present in the solid matrix in an amount from about 0.5% to about 15%, preferably from about 2% to about 10% by weight of the solid pharmaceutical composition. In some such embodiments, the pharmaceutically acceptable meltable binder is polyethylene glycol (PEG), such as PEG 3350.

In certain embodiments, the solid pharmaceutical composition comprises a disintegrant. In some such embodiments, the disintegrant is present in the solid pharmaceutical composition in an amount from about 2% to about 30% by weight of the solid pharmaceutical composition. In some such embodiments, the disintegrant is crospovidone.

In certain embodiments, the solid pharmaceutical composition comprises a glidant. In some such embodiments, the glidant is present in the solid pharmaceutical composition in an amount from about 0.1% to about 5% by weight of the solid pharmaceutical composition, alternatively from about 0.1% to about 2% by weight of the solid pharmaceutical composition. In some such embodiments, the glidant is colloidal silicon dioxide.

In certain embodiments, the solid pharmaceutical composition further comprises a pH modifying agent. In some such embodiments, the pH modifying agent is mixed with the solid matrix. In some such embodiments, the pH modifying agent is present in an amount wherein the weight ratio of Compound A, or salt thereof to the pH modifying agent is from about 1:1 to about 10:1. Alternatively the ratio is from about 2:1 to about 10:1. Alternatively, the ratio is from about 2:1 to about 8:1. Alternatively, the ratio is from about 2:1 to about 6:1. Alternatively, the ratio is from about 2:1 to about 4:1. Alternatively the ratio is from about 2:1 to about 1:1.

In some such embodiments, the pH modifying agent is sodium carbonate, such as sodium carbonate monohydrate.

In certain embodiments, the solid pharmaceutical composition further comprises a glidant and/or a lubricant.

The disclosure is also directed to solid pharmaceutical compositions comprising Compound A or a pharmaceutically acceptable salt thereof, a pharmaceutically acceptable meltable binder, which are in a solid matrix, such as amorphous solid dispersion, and, optionally, a disintegrant, and/or a glidant.

In certain embodiments, Compound A or a pharmaceutically acceptable salt thereof is present in the solid matrix, such as amorphous solid dispersion in an amount from about 40% to about 80% by weight of the solid pharmaceutical composition.

In certain embodiments, the salt of Compound A is the monosodium salt (sodium 4-((R)-2-[5-(2-fluoro-3-methoxy-phenyl)-3-(2-fluoro-6-trifluoromethyl-benzyl)-4-methyl-2,6-dioxo-3,6-dihydro-2H-pyrimidin-1-yl]-1-phenyl-ethyl-amino)butanoate).

In certain embodiments, the pharmaceutically acceptable meltable binder is present in the solid matrix, such as amorphous solid dispersion in an amount from about 0.5% to about 15%, preferably from about 2% to about 10% by weight of the solid pharmaceutical composition. In certain embodiments, the pharmaceutically acceptable meltable binder is present in the solid pharmaceutical composition in an amount from about 0.5% to about 15%, preferably from about 2% to about 10% by weight of the solid pharmaceutical composition. In some such embodiments, the pharmaceutically acceptable meltable binder is polyethylene glycol (PEG), such as PEG 3350.

In certain embodiments, the disintegrant is present the solid pharmaceutical composition in an amount from about 2% to about 30% by weight of the solid pharmaceutical composition. In some such embodiments, the disintegrant is crospovidone.

In certain embodiments, the glidant is present in the solid pharmaceutical composition in an amount from about 0.1% to about 5% by weight of the solid pharmaceutical composition, alternatively from about 0.1% to about 2% by weight of the solid pharmaceutical composition. In some such embodiments, the glidant is colloidal silicon dioxide.

In certain embodiments, the solid pharmaceutical composition is prepared by melt processing, such as by melt extrusion or by melt granulation. In certain embodiments, an extrudate prepared by melt extrusion is cut or milled into granules.

In certain embodiments, the solid pharmaceutical composition further comprises a pH modifying agent. In some such embodiments, the pH modifying agent is mixed with the solid matrix, such as amorphous solid dispersion. In some such embodiments, the pH modifying agent is present in an amount wherein the weight ratio of Compound A, or salt thereof to the pH modifying agent is from about 1:1 to about 10:1. Alternatively the ratio is from about 2:1 to about 10:1. Alternatively, the ratio is from about 2:1 to about 8:1. Alternatively, the ratio is from about 2:1 to about 6:1. Alternatively, the ratio is from about 2:1 to about 4:1. Alternatively the ratio is from about 2:1 to about 1:1. In some such embodiments, the pH modifying agent is sodium carbonate, such as sodium carbonate monohydrate.

In certain embodiments, the solid pharmaceutical composition further comprises a lubricant.

In certain embodiments, the solid pharmaceutical composition comprises an intragranular portion and an extragranular portion. In some such embodiments, the intragranular portion comprises the solid matrix, such as amorphous solid dispersion. In some such embodiments, the extragranular portion comprises a lubricant.

The disclosure is also directed to solid pharmaceutical compositions comprising a melt-processed mixture of (a) Compound A or a pharmaceutically acceptable salt thereof, (b) at least one pharmaceutically acceptable meltable binder, and, optionally, (c) a pH modifying agent, (d) a disintegrant, and/or (e) a glidant.

In certain embodiments, Compound A or a pharmaceutically acceptable salt thereof is present in an amount from about 20% to about 90% by weight of the total weight of the melt-processed mixture. In certain embodiments, Compound A or a pharmaceutically acceptable salt thereof is present in an amount from about 35% to about 80% by weight of the total weight of the melt-processed mixture. In certain embodiments, Compound A or a pharmaceutically acceptable salt thereof is present in an amount from about 50% to about 70% by weight of the total weight of the melt-processed mixture. In certain embodiments, Compound A or a pharmaceutically acceptable salt thereof is present in an amount from about 55% to about 60% by weight of the total weight of the melt-processed mixture.

In certain embodiments, the salt of Compound A is the monosodium salt (sodium 4-((R)-2-[5-(2-fluoro-3-methoxy-phenyl)-3-(2-fluoro-6-trifluoromethyl-benzyl)-4-methyl-2,6-dioxo-3,6-dihydro-2H-pyrimidin-1-yl]-1-phenyl-ethyl-amino)butanoate).

In certain embodiments, the pharmaceutically acceptable meltable binder is present in an amount from about 2% to about 10% by weight of the total weight of the melt-processed mixture. In some such embodiments, the pharmaceutically acceptable meltable binder is polyethylene glycol (PEG), such as PEG 3350.

In certain embodiments, the solid pharmaceutical composition comprises a melt-processed mixture of (a) Compound A or a pharmaceutically acceptable salt thereof, and (b) at least one pharmaceutically acceptable meltable binder, optionally (c) a pH modifying agent, (d) a disintegrant, and/or (e) a glidant. In some such embodiments, the pH modifying agent is present in an amount wherein the weight ratio of Compound A, or salt thereof to the pH modifying agent is from about 1:1 to about 10:1. Alternatively the ratio is from about 2:1 to about 10:1. Alternatively, the ratio is from about 2:1 to about 8:1. Alternatively, the ratio is from about 2:1 to about 6:1. Alternatively, the ratio is from about 2:1 to about 4:1. Alternatively the ratio is from about 2:1 to about 1:1. In some such embodiments, the pH modifying agent is sodium carbonate, such as sodium carbonate monohydrate.

In certain embodiments, the disintegrant is present in an amount from about 2% to about 10% by weight of the total weight of the melt-processed mixture. In some such embodiments, the disintegrant is crospovidone.

In certain embodiments, the glidant is present in an amount from about 0.1% to about 5% by weight of the total weight of the melt-processed mixture, alternatively from about 0.1% to about 2% by weight of the total weight of the melt-processed mixture. In some such embodiments, the glidant is colloidal silicon dioxide.

In certain embodiments, the melt-processed mixture is prepared by melt extrusion or melt-granulation. In some such embodiments, the melt-processed mixture is prepared by melt extrusion. In some such embodiments, an extrudate prepared by melt extrusion is cut or milled into granules. In some such embodiments, the melt-processed mixture is prepared by melt granulation.

In certain embodiments, the solid pharmaceutical composition further comprises a glidant and/or a lubricant.

The disclosure is also directed to a solid dispersion comprising Compound A or a pharmaceutically acceptable salt thereof dispersed in a solid matrix, wherein the solid matrix comprises at least one pharmaceutically acceptable meltable binder. In certain embodiments, the solid dispersion is in essentially non-crystalline, for example amorphous, form.

In certain embodiments, the salt of Compound A is the monosodium salt (sodium 4-((R)-2-[5-(2-fluoro-3-methoxyphenyl)-3-(2-fluoro-6-trifluoromethyl-benzyl)-4-methyl-2,6-dioxo-3,6-dihydro-2H-pyrimidin-1-yl]-1-phenyl-ethylamino)butanoate).

In certain embodiments, the pharmaceutically acceptable meltable binder is a poloxomer, such as poloxamer 188, a cellulose derivative, such as hydroxypropylcellulose, or a polyethylene glycol (PEG), such as PEG 3350, glycerol monosteatrate or stearic acid.

In certain embodiments, the weight ratio of Compound A or a pharmaceutically acceptable salt thereof to the pharmaceutically acceptable meltable binder in the solid dispersion is from about 1:1 to about 15:1, alternatively from about 3:1 to about 12:1. In certain embodiments, the weight ratio of Compound A or a pharmaceutically acceptable salt thereof to the pharmaceutically acceptable meltable binder is about 3:1, about 4:1, about 5:1, about 6:1, about 7:1, about 8:1, about 9:1, about 10:1, about 11:1, or about 12:1. In some such embodiments, the weight ratio of Compound A or a pharmaceutically acceptable salt thereof to the pharmaceutically acceptable meltable binder is about 12:1.

In certain embodiments, the solid dispersion is prepared by melt processing, such as by melt extrusion or by melt granulation. In certain embodiments, an extrudate prepared by melt extrusion is cut or milled into granules. In certain embodiments, one or more additional excipients, such as a pH modifying agent and/or a disintegrant is included in the melt granulation.

The disclosure is also directed to a solid matrix, such as amorphous solid dispersion comprising Compound A or a pharmaceutically acceptable salt thereof, a pharmaceutically acceptable meltable binder.

In certain embodiments, the salt of Compound A is the monosodium salt (sodium 4-((R)-2-[5-(2-fluoro-3-methoxyphenyl)-3-(2-fluoro-6-trifluoromethyl-benzyl)-4-methyl-2,6-dioxo-3,6-dihydro-2H-pyrimidin-1-yl]-1-phenyl-ethylamino)butanoate).

In certain embodiments, the pharmaceutically acceptable meltable binder is a poloxomer, such as poloxamer 188, a cellulose derivative, such as hydroxypropylcellulose, or a polyethylene glycol (PEG), such as PEG 3350.

In certain embodiments, the weight ratio of Compound A or a pharmaceutically acceptable salt thereof to the pharmaceutically acceptable meltable binder in the solid matrix, such as amorphous solid dispersion is from about 1:1 to about 15:1, alternatively from about 3:1 to about 12:1. In certain embodiments, the weight ratio of Compound A or a pharmaceutically acceptable salt thereof to the pharmaceutically acceptable meltable binder is about 3:1, about 4:1, about 5:1, about 6:1, about 7:1, about 8:1, about 9:1, about 10:1, about 11:1, or about 12:1. In some such embodiments, the weight ratio of Compound A or a pharmaceutically acceptable salt thereof to the pharmaceutically acceptable meltable binder is about 12:1.

In certain embodiments, the solid matrix, such as a solid matrix, such as amorphous solid dispersion is prepared by melt processing, such as by melt extrusion or by melt granulation. In certain embodiments, an extrudate prepared by melt extrusion is cut or milled into granules. In certain embodiments, one or more additional excipients, such as a pH modifying agent and/or a disintegrant is included in the melt granulation.

The disclosure is also directed to a pharmaceutical composition comprising a granule, the granule comprising (i) a solid dispersion, wherein the solid dispersion comprises Compound A or a pharmaceutically acceptable salt thereof and at least one pharmaceutically acceptable meltable binder, and (ii) one or more additional components outside the solid dispersion.

In certain embodiments, the salt of Compound A is the monosodium salt (sodium 4-((R)-2-[5-(2-fluoro-3-methoxyphenyl)-3-(2-fluoro-6-trifluoromethyl-benzyl)-4-methyl-2,6-dioxo-3,6-dihydro-2H-pyrimidin-1-yl]-1-phenyl-ethylamino)butanoate).

In certain embodiments, Compound A or a pharmaceutically acceptable salt thereof is present in the granule in an amount from about 40% to about 80% by weight of the pharmaceutical composition.

In certain embodiments, the pharmaceutically acceptable meltable binder is present in the granule in an amount from about 0.5% to about 15%, preferably from about 2% to about 10% by weight of the pharmaceutical composition. In some such embodiments, the pharmaceutically acceptable meltable binder is a poloxomer, such as poloxamer 188, a cellulose derivative, such as hydroxypropylcellulose, or a polyethylene glycol (PEG), such as PEG 3350.

In certain embodiments, the one or more additional components outside the solid dispersion includes a pH modifying agent. In some such embodiments, the pH modifying agent is present in the granule, wherein the weight ratio of Compound A, or salt thereof to the pH modifying agent is from about 1:1 to about 10:1. Alternatively the ratio is from about 2:1 to about 10:1. Alternatively, the ratio is from about 2:1 to about 8:1. Alternatively, the ratio is from about 2:1 to about 6:1. Alternatively, the ratio is from about 2:1 to about 4:1. Alternatively the ratio is from about 2:1 to about 1:1. In some such embodiments, the pH modifying agent is sodium carbonate, such as sodium carbonate monohydrate.

In certain embodiments, the one or more additional components outside the solid dispersion includes a disintegrant. In some such embodiments, the disintegrant is present in the granule in an amount from about 2% to about 30% by weight of the pharmaceutical composition. In some such embodiments, the disintegrant is crospovidone.

In certain embodiments, the one or more additional components outside the solid dispersion includes a glidant. In some such embodiments, the glidant is present in the granule in an amount from about 0.1% to about 5% by weight of the pharmaceutical composition, alternatively from about 0.1% to about 2% by weight of the pharmaceutical composition. In some such embodiments, the glidant is colloidal silicon dioxide.

In certain embodiments, the granule is prepared by melt processing, such as by melt granulation.

The disclosure is yet further directed to methods of achieving a high drug load of Compound A or a pharmaceutically acceptable salt thereof in an oral dosage form.

In certain embodiments, the methods comprise preparing a pharmaceutical composition comprising Compound A or a pharmaceutically acceptable salt thereof in a solid matrix, for example, an amorphous solid dispersion.

In certain embodiments, the methods comprise melt-processing Compound A or a pharmaceutically acceptable salt thereof and at least one pharmaceutically acceptable meltable binder, such as by melt granulation or melt extrusion.

The disclosure is also directed to methods for treating endometriosis in a subject in need of such treatment, wherein the method comprises administering to the subject a solid pharmaceutical composition of the present disclosure. In certain embodiments, the method further comprises administering to the subject a hormone to reduce or alleviate potential side effects of Compound A or a pharmaceutically acceptable salt thereof. For example, the method may comprise administration of an estrogen, a progestogen, such as a progestin, or a combination thereof. Such treatments are commonly referred to as "add-back" therapy. In some such embodiments, the add-back therapy comprises estradiol and a norethisterone prodrug, such as norethindrone acetate.

The disclosure is also directed to solid pharmaceutical compositions for use in treating endometriosis.

The disclosure is also directed to methods for treating uterine fibroids in a subject in need of such treatment, wherein the method comprises administering to the subject a solid pharmaceutical composition of the present disclosure. In certain embodiments, the method further comprises administering to the subject a hormone to reduce or alleviate potential side effects of Compound A or a pharmaceutically acceptable salt thereof. For example, the method may comprise administration of an estrogen, a progestin, or a combination thereof. Such treatments are commonly referred to as "add-back" therapy. In some such embodiments, the add-back therapy comprises estradiol and a norethisterone prodrug, such as norethindrone acetate.

The disclosure is also directed to solid pharmaceutical compositions for use in treating uterine fibroids.

These and other objects of the invention are described in the following paragraphs. These objects should not be deemed to narrow the scope of the invention.

DETAILED DESCRIPTION OF THE INVENTION

Figure 1:
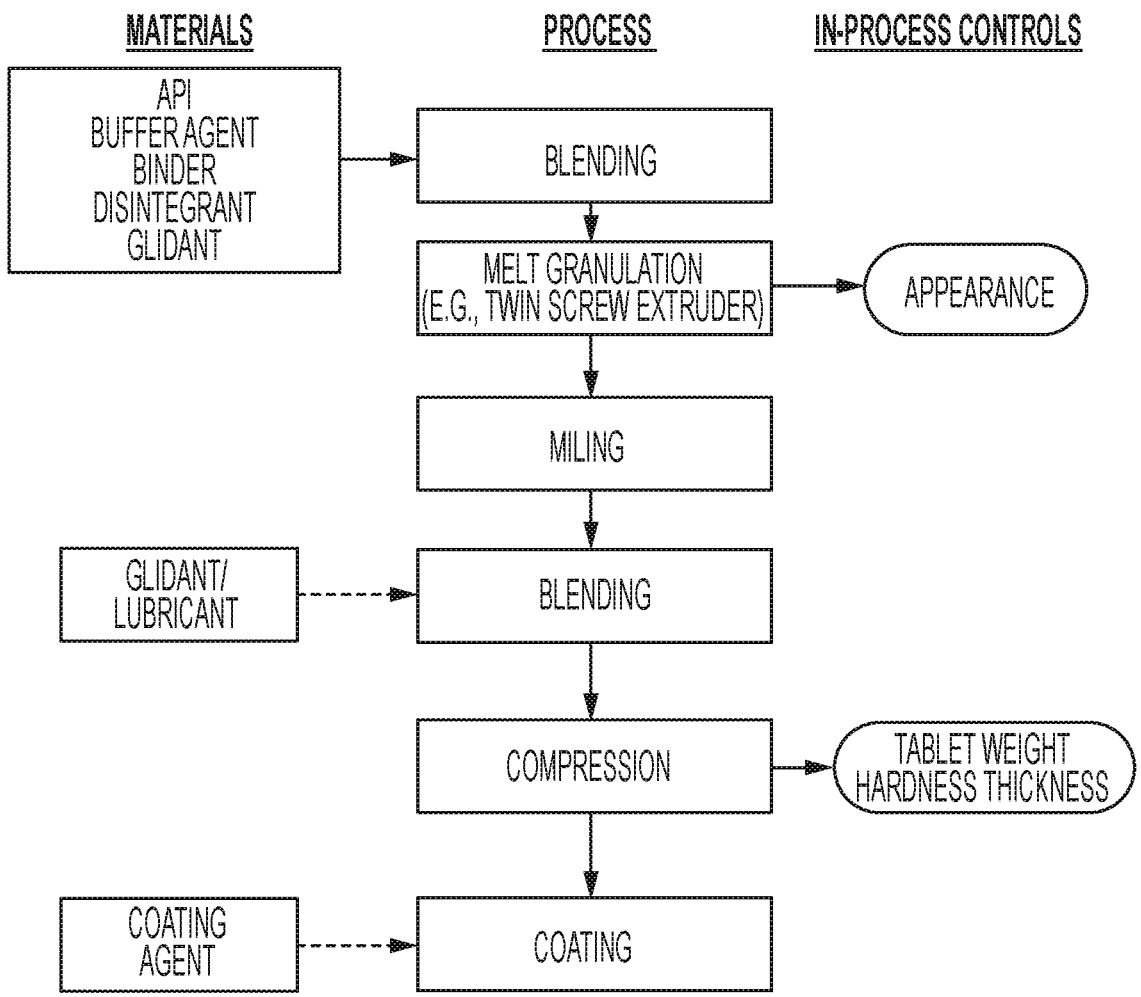
FIG. 1 is a melt-processing flow diagram.

This detailed description is intended only to acquaint others skilled in the art with the present invention, its principles, and its practical application so that others skilled in the art may adapt and apply the invention in its numerous forms, as they may be best suited to the requirements of a particular use. This description and its specific examples are intended for purposes of illustration only. This invention, therefore, is not limited to the embodiments described in this patent application, and may be variously modified.

A. DEFINITIONS

As used in the specification and the appended claims, unless specified to the contrary, the following terms have the meaning indicated:

The term "API" as used herein stands for "active pharmaceutical ingredient." The preferred API as disclosed herein is 4-((R)-2-[5-(2-fluoro-3-methoxy-phenyl)-3-(2-fluoro-6-trifluoromethyl-benzyl)-4-methyl-2,6-dioxo-3,6-dihydro-2H-pyrimidin-1-yl]-1-phenyl-ethylamino)-butyric acid (Compound A) or a pharmaceutically acceptable salt thereof and, preferably is sodium 4-((R)-2-[5-(2-fluoro-3-methoxy-phenyl)-3-(2-fluoro-6-trifluoromethyl-benzyl)-4-methyl-2,6-dioxo-3,6-dihydro-2H-pyrimidin-1-yl]-1-phenyl-ethylamino)butanoate.

The term "solid matrix" as used herein refers to a molecular mixture of an API and one or more meltable binders. In one embodiment, the solid matrix may be an amorphous and crystalline solid dispersion. The API may be dispersed as amorphous clusters or crystalline particles in the matrix and/or the API may be molecularly dispersed and/or dispersed throughout the matrix. Different types of solid dispersions can be distinguished based on their molecular arrangements. These different types of solid dispersions include, but are not limited to, (1) eutectic mixtures; (2) solid solutions where matrix is in crystalline state, including continuous solid solutions, discontinuous solid solutions, substitutional solid solutions, and interstitial solid solutions; and (3) glass solutions where matrix is in amorphous state and API is molecularly dispersed throughout the matrix. The term "molecularly dispersed" as used herein refers to the random distribution of a compound (e.g., Compound A or a salt thereof) with a polymer. In certain embodiments, a compound may be dispersed within a matrix formed by the polymer in its solid state such that the compound is immobilized in its amorphous form.

As used herein, the term "pharmaceutical composition" means a composition comprising Compound A or a pharmaceutically acceptable salt thereof and, optionally, one or more pharmaceutically acceptable excipients.

The term "pharmaceutically acceptable" is used adjectivally to mean that the modified noun is appropriate for use as a pharmaceutical product for human use or as a part of a pharmaceutical product for human use.

The term "subject" includes humans and other primates as well as other mammals. The term subject includes, for example, a healthy premenopausal female as well as a female patient having, for example, endometriosis or uterine fibroids. In certain embodiments, the subject is a human. In certain embodiments, the subject is an adult human female. In certain embodiments, the subject is a woman, typically a premenopausal woman, having endometriosis. In certain embodiments, the subject is a woman, typically a premenopausal woman, having uterine fibroids.

The term "therapeutically effective amount" means a sufficient amount of the API or pharmaceutical composition to treat a condition, disorder, or disease, at a reasonable benefit/risk ratio applicable to any medical treatment.

The terms "treat", "treating" and "treatment" refer to a method of alleviating or abrogating a condition, disorder, or disease and/or the signs and/or attendant symptoms thereof.

B. DRUG SUBSTANCE

Pharmaceutical compositions disclosed herein comprise at least one active pharmaceutical ingredient: 4-((R)-2-[5-(2-fluoro-3-methoxy-phenyl)-3-(2-fluoro-6-trifluoromethyl-benzyl)-4-methyl-2,6-dioxo-3,6-dihydro-2H-pyrimidin-1-yl]-1-phenyl-ethylamino)-butyric acid (Compound A) or a pharmaceutically acceptable salt thereof.

Compound A has the following formula:

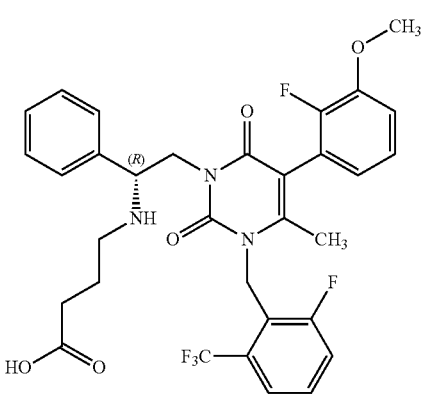

Compound A is an orally active, non-peptide GnRH antagonist and is unlike other GnRH agonists and injectable (peptide) GnRH antagonists. Compound A produces a dose dependent suppression of pituitary and ovarian hormones in women. Methods of making Compound A and a pharmaceutically acceptable salt thereof, as well as similar compounds, are described in WO2001/055119, WO 2005/007165, and PCT application WO2017/221144, the contents of which are herein incorporated by reference. Deuterated version of the drug substance is also contemplated to be within the scope of this invention. Deuterated versions of the drug substance are described in patent application CN108129400 A, the contents of which are incorporated herein by reference. Elagolix and elagolix sodium are used interchangeably to refer to the drug substance. Unless specifically directed, elagolix contemplates elagolix sodium within its scope.

In certain embodiments, 4-((R)-2-[5-(2-fluoro-3-methoxy-phenyl)-3-(2-fluoro-6-trifluoromethyl-benzyl)-4-methyl-2,6-dioxo-3,6-dihydro-2H-pyrimidin-1-yl]-1-phenyl-ethylamino)-butyric acid exists in zwitterionic form. For example, both the carboxylic acid and the tertiary amine are ionized and, thus, the molecule has no overall charge but does have charge separation. Such zwitterionic forms are included within the scope of the term "Compound A or a pharmaceutically acceptable salt thereof."

The acid dissociation constants were determined by potentiometric titration method. The pKa values of elagolix are 4.0 (A) and 7.9 (B) Based on the pKa values and the molecular structure, there are three species that can exist at different pHs for elagolix. The first is XH2+, where the carboxylic acid is not ionized but the secondary amine is; the molecule has an overall +1 charge, and the main species at pHs below 4.0. The second is XH, where both the carboxylic acid and the tertiary amine are ionized. The molecule is zwitterionic in nature, i.e. the molecule has no overall charge but charge separation; this is the main species for elagolix at pHs between 4.0 and 7.9. The third is X−, where the carboxylic acid is ionized but the tertiary amine is not. The molecule has an overall −1 charge; this is the main species for elagolix at pHs about 7.9.

Compound A may be present in a pharmaceutical composition in the form of acid or base addition salts. Acid addition salts of the free amino compounds of the present invention may be prepared by methods well known in the art, and may be formed from organic and inorganic acids. Suitable organic acids include maleic, fumaric, benzoic, ascorbic, succinic, methanesulfonic, acetic, trifluoroacetic, oxalic, propionic, tartaric, salicylic, citric, gluconic, lactic, mandelic, cinnamic, aspartic, stearic, palmitic, glycolic, glutamic, and benzenesulfonic acids. Suitable inorganic acids include hydrochloric, hydrobromic, sulfuric, phosphoric, and nitric acids. Suitable base addition salts include those salts that form with the carboxylate anion and include salts formed with organic and inorganic cations such as those chosen from the alkali and alkaline earth metals (for example, lithium, sodium, potassium, magnesium, barium and calcium), as well as the ammonium ion and substituted derivatives thereof (for example, dibenzylammonium, benzylammonium, 2-hydroxyethylammonium, and the like). Thus, the term "pharmaceutically acceptable salt" of Compound A is intended to encompass any and all acceptable salt forms.

In certain embodiments, Compound A is present in a pharmaceutical composition in the form of a pharmaceutically acceptable salt. In certain embodiments, a pharmaceutically acceptable salt of Compound A is the sodium salt of Compound A. The monosodium salt of Compound A has a molecular formula of $C_{32}H_{29}F_5N_3O_5Na$, which corresponds to a molecular weight of about 653.6 (salt) and about 631.6 (free form). The monosodium salt of Compound A has the following formula:

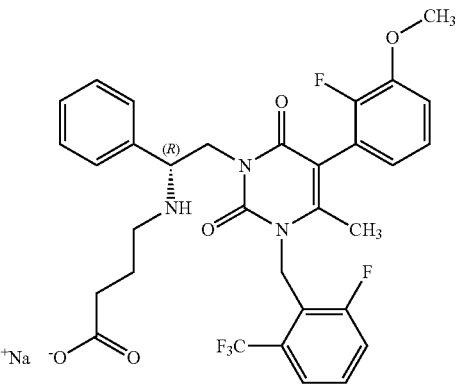

In certain embodiments, the monosodium salt is in the form of an amorphous solid. In certain embodiments, the monosodium salt is in crystalline or partially crystalline form.

As used herein, and in the absence of a specific reference to a particular pharmaceutically acceptable salt of Compound A, any dosages, whether expressed in milligrams or as a percentage by weight or as a ratio with another ingredient, should be taken as referring to the amount of Compound A free form.

In certain embodiments, Compound A or a pharmaceutically acceptable salt thereof is present in a pharmaceutical composition in an amount from about 45 mg to about 450 mg of Compound A. In certain embodiments, the amount of Compound A, or pharmaceutically acceptable salt thereof, is from about 50 mg to about 400 mg. In certain embodiments, the amount of Compound A, or pharmaceutically acceptable salt thereof, is from about 100 mg to about 350 mg. In other such embodiments, the amount of Compound A, or pharmaceutically acceptable salt thereof, is from about 190 mg to about 210 mg, preferably about 200 mg. In still other embodiments, the amount of Compound A, or pharmaceutically acceptable salt thereof, is from about 290 mg to about 310 mg, preferably about 300 mg.

In certain embodiments, the pharmaceutical composition provides a high drug load. For example, in embodiments where the composition is a tablet, the tablet may contain at least 20% drug substance, at least 25% drug substance, at least 30% drug substance, at least 35% drug substance, at least 40% drug substance, at least 45% drug substance, at least 50% drug substance, at least 55% drug substance, or at least 60% drug substance. Alternatively, the tablet may contain about 40%, about 41%, about 42%, about 43%, about 44%, about 45%, about 46%, about 47%, about 48%, about 49%, about 50%, about 51%, about 52%, about 53%, about 54%, about 55%, about 56%, about 57%, about 58%, about 59%, about 60%, about 61%, about 62%, about 63%, about 64%, or about 65% drug substance. As another example, in embodiments where the composition is a tablet, the pharmaceutical composition comprises sodium 4-((R)-2-[5-(2-fluoro-3-methoxy-phenyl)-3-(2-fluoro-6-trifluoromethyl-benzyl)-4-methyl-2,6-dioxo-3,6-dihydro-2H-pyrimidin-1-yl]-1-phenyl-ethylamino)butanoate, such as at least 40%, at least 45%, at least 50%, at least 55%, or at least 60% sodium 4-((R)-2-[5-(2-fluoro-3-methoxy-phenyl)-3-(2-fluoro-6-trifluoromethyl-benzyl)-4-methyl-2,6-dioxo-3,6-dihydro-2H-pyrimidin-1-yl]-1-phenyl-ethylamino)butanoate. Alternatively, the tablet may contain about 40%, about 41%, about 42%, about 43%, about 44%, about 45%, about 46%, about 47%, about 48%, about 49%, about 50%, about 51%, about 52%, about 53%, about 54%, about 55%, about 56%, about 57%, about 58%, about 59%, about 60%, about 61%, about 62%, about 63%, about 64%, or about 65% sodium 4-((R)-2-[5-(2-fluoro-3-methoxy-phenyl)-3-(2-fluoro-6-trifluoromethyl-benzyl)-4-methyl-2,6-dioxo-3,6-dihydro-2H-pyrimidin-1-yl]-1-phenyl-ethylamino)butanoate.

C. PHARMACEUTICAL COMPOSITIONS

Solid pharmaceutical compositions comprising Compound A or a pharmaceutically acceptable salt thereof may be used to treat endometriosis or uterine fibroids. Solid pharmaceutical compositions or dosage forms as described herein may preferably be oral dosage forms, which can be administered to humans. A solid oral dosage form may be in the form of, for example, capsules, granules, granulates, pellets, pills, powders and/or tablets.

The present disclosure provides pharmaceutical formulations and functional excipients to, inter alia, provide a high drug load of Compound A or a pharmaceutically acceptable salt thereof in an oral dosage form.

In certain embodiments, the disclosed solid pharmaceutical compositions comprise at least one pharmaceutically acceptable meltable binder. In some such embodiments, the pharmaceutically acceptable meltable binder comprises a meltable polymer, a meltable glyceride derivative, a meltable polyol, a meltable polysaccharide, a meltable cellulose derivative, a meltable povidone, a meltable amphiphile, or a combination thereof. In some such embodiments, the solid pharmaceutical composition further comprises an optional plasticizer.

In certain embodiments, the pharmaceutically acceptable meltable binder comprises a meltable polymer. In some such embodiments, the pharmaceutically acceptable meltable binder comprises a hydrophilic meltable polymer. For example, the pharmaceutically acceptable meltable binder may be a polyalkylene glycol, such as polyethylene glycol (PEG), or a poloxamer. In some such embodiments, the pharmaceutically acceptable meltable binder comprises PEG 3350. In some such embodiments, the pharmaceutically acceptable meltable binder comprises poloxamer 188. In some such embodiments, the pharmaceutically acceptable meltable polymer comprises an amphiphilic polymer. For example, the pharmaceutically acceptable meltable binder may be polyvinyl caprolactam-polyvinyl acetate-polyethylene glycol graft copolymer. In some such embodiments, the meltable polymer may be selected from copolymer of N-vinyl lactam, polyalkylene glycol, polyacrylate, polymethacrylate, polyacrylamide, polyvinyl alcohol, vinyl acetate polymer, or combinations thereof.

In certain embodiments, the pharmaceutically acceptable meltable binder comprises a meltable glyceride derivative, such as polyoxylglyceride, behenoyl polyoxyl-8 glyceride, or glyceryl monostearate. In certain embodiments, the pharmaceutically acceptable meltable binder comprises a meltable polyol, such as maltitol or isomalt. In certain embodiments, the pharmaceutically acceptable meltable binder comprises a meltable polysaccharide, such as maltodextrin. In certain embodiments, the pharmaceutically acceptable meltable binder comprises a meltable cellulose derivative, such as hydroxypropyl cellulose. In certain embodiments, the pharmaceutically acceptable meltable binder comprises a meltable povidone, such as copovidone. In certain embodiments, the pharmaceutically acceptable meltable binder comprises a meltable amphiphile, such as d-α tocopheryl polyethylene glycol 1000 succinate.

In certain embodiments, a pharmaceutically acceptable meltable binder is present in the solid pharmaceutical composition in an amount from about 0.1% to about 20% by weight (w/w) of the solid pharmaceutical composition. In certain embodiments, a pharmaceutically acceptable meltable binder is present in the solid pharmaceutical composition in an amount from about 2% to about 10% by weight (w/w) of the solid pharmaceutical composition. In certain embodiments, a pharmaceutically acceptable meltable binder is present in the solid pharmaceutical composition in an amount from about 3% to about 8% by weight (w/w) of the solid pharmaceutical composition. In certain embodiments, a pharmaceutically acceptable meltable binder is present in the solid pharmaceutical composition in an amount from about 4% to about 6% by weight (w/w) of the solid pharmaceutical composition. In certain embodiments, the solid pharmaceutical composition includes about 5% by weight of a pharmaceutically acceptable meltable binder.

In certain embodiments, the meltable binder is polyethylene glycol (PEG), such as PEG 1450, PEG 3350, PEG 4000, PEG 6000, or PEG 8000. In certain embodiments, the meltable binder is PEG 3350. In certain embodiments, polyethylene glycol is present in the solid pharmaceutical composition in an amount from about 0.1% to about 20% by weight (w/w) of the solid pharmaceutical composition. In certain embodiments, polyethylene glycol is present in the solid pharmaceutical composition in an amount from about 2% to about 10% by weight (w/w) of the solid pharmaceutical composition. In certain embodiments, polyethylene glycol is present in the solid pharmaceutical composition in an amount from about 3% to about 8% by weight (w/w) of the solid pharmaceutical composition. In certain embodiments, polyethylene glycol is present in the solid pharmaceutical composition in an amount from about 4% to about 6% by weight (w/w) of the solid pharmaceutical composition. In certain embodiments, the solid pharmaceutical composition includes about 4.8% by weight of polyethylene glycol, such as PEG 3350.

In certain embodiments, the weight ratio of Compound A or a pharmaceutically acceptable salt thereof to the pharmaceutically acceptable meltable binder is from about 1:1 to about 15:1, alternatively from about 3:1 to about 12:1. In certain embodiments, the weight ratio of Compound A or a pharmaceutically acceptable salt thereof to the pharmaceutically acceptable meltable binder is about 3:1, about 4:1, about 5:1, about 6:1, about 7:1, about 8:1, about 9:1, about 10:1, about 11:1, or about 12:1. In some such embodiments, the weight ratio of Compound A or a pharmaceutically acceptable salt thereof to the pharmaceutically acceptable meltable binder is about 12:1.

In certain embodiments, Compound A or the pharmaceutically acceptable salt thereof, the pharmaceutically acceptable meltable binder, and, optionally, one or more additional excipients are mixed, preferably by melt-processing. There are at least two types of interaction possible between Compound A or a pharmaceutically acceptable salt thereof, the pharmaceutically acceptable meltable binder, and the optional additional excipients. In certain embodiments, Compound A or a pharmaceutically acceptable salt thereof and the pharmaceutically acceptable meltable binder form a single-phase system where API is miscible with the binder. In certain embodiments, Compound A or a pharmaceutically acceptable salt thereof and the pharmaceutically acceptable meltable binder form a multi-phase system where API-binder physically mixed with the other excipients in the matrix.

In certain embodiments, the solid pharmaceutical composition comprises the following components: Compound A or a pharmaceutically acceptable salt thereof, a pharmaceutically acceptable meltable binder, and, optionally, one or more additional excipients. In certain embodiments, two or more components of the composition are miscible with each other. In some such embodiments, miscibility is dependent upon the properties of the components and/or upon the processing conditions (e.g., time and/or temperature of melting). In some such embodiments, two or more components of the composition are completely miscible with each other. For example, in certain embodiments, sodium 4-((R)-2-[5-(2-fluoro-3-methoxy-phenyl)-3-(2-fluoro-6-trifluorom-ethyl-benzyl)-4-methyl-2,6-dioxo-3,6-dihydro-2H-pyrimidin-1-yl]-1-phenyl-ethylamino)butanoate and the pharmaceutically acceptable meltable binder are completely miscible with each other. In some such embodiments, the miscible components can be combined to form a single-phase system. In other such embodiments, two or more components of the composition are only partially miscible or immiscible with each other. In some such embodiments, the partially miscible or immiscible components can be combined to form a multi-phase system. A multi-phase system may be, for example, characterized by two distinct phases. For example, in certain embodiments, sodium 4-((R)-2-[5-(2-fluoro-3-methoxy-phenyl)-3-(2-fluoro-6-trifluorom-ethyl-benzyl)-4-methyl-2,6-dioxo-3,6-dihydro-2H-pyrimidin-1-yl]-1-phenyl-ethylamino)butanoate and the pharmaceutically acceptable meltable binder are only partially miscible. In some such embodiments, the multi-phase system comprises API molecularly dispersed in a matrix and API in a separate phase—mixed with the matrix. As another example, in certain embodiments, a pH modifying agent, such as sodium carbonate, and the pharmaceutically acceptable meltable binder are immiscible. In some such embodiments, the multi-phase system comprises API molecularly dispersed in a matrix and a pH modifying agent in a separate phase—mixed with the matrix.

In certain embodiments, the solid pharmaceutical composition comprises a solid dispersion. In certain embodiments, the solid dispersion comprises Compound A or a pharmaceutically acceptable salt thereof and a pharmaceutically acceptable meltable binder. In certain embodiments, the solid dispersion comprises amorphous Compound A or a pharmaceutically acceptable salt thereof. In certain embodiments, the solid dispersion comprises sodium 4-((R)-2-[5-(2-fluoro-3-methoxy-phenyl)-3-(2-fluoro-6-trifluorom-ethyl-benzyl)-4-methyl-2,6-dioxo-3,6-dihydro-2H-pyrimidin-1-yl]-1-phenyl-ethylaminor)butanoate. In certain embodiments, the solid dispersion comprises amorphous sodium 4-((R)-2-[5-(2-fluoro-3-methoxy-phenyl)-3-(2-fluoro-6-trifluoromethyl-benzyl)-4-methyl-2,6-dioxo-3,6-dihydro-2H-pyrimidin-1-yl]-1-phenyl-ethylamino)butanoate. In certain embodiments, the pharmaceutically acceptable meltable binder is polyethylene glycol, such as PEG 3350. In certain embodiments, the solid pharmaceutical composition further comprises drug particles mixed with the solid dispersion. In certain embodiments, the solid pharmaceutical composition comprises a solid dispersion having Compound A or a pharmaceutically acceptable salt thereof molecularly dispersed in a meltable binder as well as Compound A or a pharmaceutically acceptable salt thereof mixed with the solid dispersion.

In certain embodiments, the solid pharmaceutical composition comprises a multi-phase system, such as a two-phase system. In certain embodiments, the multi-phase system comprises API both as a molecular dispersion in a meltable binder matrix and API in a separate phase—mixed with the meltable binder matrix. In certain embodiments, Compound A or a pharmaceutically acceptable salt thereof is molecularly dispersed in a meltable binder matrix. In certain embodiments, sodium 4-((R)-2-[5-(2-fluoro-3-methoxy-phenyl)-3-(2-fluoro-6-trifluoromethyl-benzyl)-4-methyl-2,6-dioxo-3,6-dihydro-2H-pyrimidin-1-yl]-1-phenyl-ethylamino)butanoate is molecularly dispersed in a meltable binder matrix. In certain embodiments, a meltable binder is molecularly dispersed in a solid matrix containing Compound A or a pharmaceutically acceptable salt thereof. In certain embodiments, one or more additional excipients are also present in the solid pharmaceutical composition (e.g., mixed with the meltable binder matrix). In certain embodiments, a meltable binder is molecularly dispersed in a solid matrix containing Compound A or a pharmaceutically acceptable salt thereof.

Drugs administered via oral solid dosage forms should dissolve in vivo before systemic absorption can take place. There are number of factors which affect drug dissolution, including physicochemical properties of the drug substance.

In certain embodiments, dissolution is assessed utilizing USP apparatus II in 900 mL of sodium phosphate, pH 6.8, at 37° C. and paddle speed of 50 rpm. In certain embodiments, dissolution is assessed utilizing USP apparatus II in 900 mL of hydrochloric acid, pH 1.2, at 37° C. and paddle speed of 50 rpm. The analytical finish may be by a high performance liquid chromatography (HPLC) system with ultraviolet (UV) detection The solid pharmaceutical compositions described herein will typically be solid oral dosage forms, preferably in the form of a tablet and, more preferably, an immediate release tablet. In certain embodiments, the immediate release tablet releases at least 50% of Compound A or a pharmaceutically acceptable salt thereof in 45 minutes, measured using USP apparatus II, in 900 mL of sodium phosphate, pH 6.8, at 37° C. and paddle speed of 50 rpm. In certain embodiments, the immediate release tablet releases at least 80% of Compound A or a pharmaceutically acceptable salt thereof in 60 minutes, measured using USP apparatus II, in 900 mL of sodium phosphate, pH 6.8, at 37° C. and paddle speed of 50 rpm. In certain embodiments, the pH is 1.2, measured using USP apparatus II, in 900 ml in 0.1N HCl at 37° C.

The solid oral dosage forms described herein will typically be in the form of a tablet. The provision of a tablet with particular pharmacokinetic parameters is a particular advantage afforded by the present invention. Pharmacokinetic parameters refer to any suitable pharmacokinetic parameters, such as $T_{max}$, $C_{max}$, and AUC. Parameters should be measured in accordance with standards and practices which would be acceptable to a pharmaceutical regulatory agency such as FDA, EMA, MHLW, or WHO. The values may be based on measurements taken at appropriate intervals following the time of tablet ingestion, such as every hour, or at increasingly sparse sampling intervals, such as 2, 4, 6, 8, 10, 12, 16, and 24 hours after ingestion. The pharmacokinetic parameters can be assessed either following a single-dose of drug or at steady state, preferably following a single-dose. In certain embodiments, pharmacokinetic parameters are determined following a single dose of the pharmaceutical composition. In certain embodiments, pharmacokinetic parameters are determined in a multiple dosing regimen. For example, pharmacokinetic parameters may be determined after several dosing intervals, e.g., at steady state. The pharmacokinetic parameters can be assessed under fasting or fed conditions, preferably under fasting conditions.

$C_{max}$ refers to the peak concentration and, in particular, the maximum observed plasma/serum concentration of drug. $T_{max}$ refers to the time to reach the peak concentration. $AUC_t$ refers to the area under the plasma concentration-time curve, where t is the time of the last measurable plasma concentration in the study. AUC refers to the area under the plasma concentration-time curve from time zero to infinity following a single dose.

In some embodiments, a solid oral dosage form (in particular a tablet) as described herein is provided, for which the 90% confidence interval of log-transformed $C_{max}$, log-transformed $AUC_t$, and/or log-transformed AUC for Compound A or a pharmaceutically acceptable salt thereof in a population of human subjects falls completely within the range 80-125% of the log-transformed $C_{max}$, log-transformed $AUC_t$, and/or log-transformed AUC∞, respectively, of a reference tablet, wherein the reference tablet comprises sodium 4-((R)-2-[5-(2-fluoro-3-methoxy-phenyl)-3-(2-fluoro-6-trifluoromethyl-benzyl)-4-methyl-2,6-dioxo-3,6-dihydro-2H-pyrimidin-1-yl]-1-phenyl-ethylamino)butanoate in an amount equivalent to about 200 mg of Compound A; polyethylene glycol 3350; sodium carbonate monohydrate; crospovidone; colloidal silicon dioxide; magnesium stearate; and an optional film coating.

In some embodiments, a solid oral dosage form (in particular a tablet) as described herein is provided, for which the 90% confidence interval of log-transformed $C_{max}$, log-transformed $AUC_t$, and/or log-transformed AUC for Compound A or a pharmaceutically acceptable salt thereof in a population of human subjects falls completely within the range 80-125% of the log-transformed Cmax, log-transformed AUCt, and/or log-transformed AUC∞, respectively, of a reference tablet, wherein the reference tablet comprises sodium 4-((R)-2-[5-(2-fluoro-3-methoxy-phenyl)-3-(2-fluoro-6-trifluoromethyl-benzyl)-4-methyl-2,6-dioxo-3,6-dihydro-2H-pyrimidin-1-yl]-1-phenyl-ethylamino)butanoate in an amount equivalent to about 300 mg of Compound A; polyethylene glycol 3350; sodium carbonate monohydrate; crospovidone; colloidal silicon dioxide; magnesium stearate; and an optional film coating.

In some embodiments, a solid oral dosage form (in particular, a tablet) is provided as described herein, wherein the dosage comprises sodium 4-((R)-2-[5-(2-fluoro-3-methoxy-phenyl)-3-(2-fluoro-6-trifluoromethyl-benzyl)-4-methyl-2,6-dioxo-3,6-dihydro-2H-pyrimidin-1-yl]-1-phenyl-ethylamino)butanoate in an amount equivalent to about 300 mg of Compound A and wherein the dosage form when administered as a single dose to a population of human subjects provides an average $C_{max}$ from about 1490 ng/mL to about 2340 ng/mL, an average $AUC_G$ from about 3770 ng·hr/mL to about 5900 ng·hr/mL, and/or an average AUC, from about 3780 ng·hr/mL to about 5910 ng·hr/mL for the population of human subjects. In some such embodiments, the solid oral dosage form is administered under fasting conditions.

In certain embodiments, administration of a solid pharmaceutical composition comprising Compound A or a pharmaceutically acceptable salt thereof results in rapid suppression of luteinizing hormone (LH) and/or follicle-stimulating hormone (FSH) levels in a female patient with endometriosis or uterine fibroids. In certain embodiments, administration of a solid pharmaceutical composition comprising Compound A or a pharmaceutically acceptable salt thereof results in partial to substantially full suppression of estradiol levels in a female patient with endometriosis or uterine fibroids. In some such embodiments, estradiol levels are less than about 50 pg/mL. In some such embodiments, estradiol levels are between about 20 pg/mL and about 50 pg/mL. In some such embodiments, estradiol levels are less than about 20 pg/mL. In some such embodiments, estradiol levels are less than about 12 pg/mL (e.g., below the lowest limit of quantitation).

The solid pharmaceutical compositions may comprise other excipients such as excipients that function as fillers, binders, disintegrants, glidants and lubricants. Thus, a solid pharmaceutical composition comprising Compound A or a pharmaceutically acceptable salt thereof, further optionally comprises one or more conventional pharmaceutically acceptable excipients.

In certain embodiments, the disclosed solid pharmaceutical compositions comprise at least one excipient that functions as a filler. Fillers may include polyols, such as dextrose, isomalt, mannitol, sorbitol, lactose, and sucrose; natural or pre-gelatinized potato or corn starch; microcrystalline cellulose (e.g., Avicel®); or a combination thereof.

Examples of suitable fillers include mannitol, such as spray dried mannitol (e.g., Pearlitol® 100SD, Pearlitol® 200SD); pregelatinized starch, such as Starch 1500@; microcrystalline cellulose, such as Avicel®; lactose monohydrate, such as Foremost® 316 Fast Flo®; mixtures of isomaltulose derivatives such as galenIQ™ 720; and other suitable fillers and combinations thereof.

In certain embodiments, a filler is present in the solid pharmaceutical composition in an amount from about 5% to about 70% by weight (w/w) of the solid pharmaceutical composition. In certain embodiments, the filler is present in the solid pharmaceutical composition in an amount from about 10% to about 60% by weight (w/w) of the solid pharmaceutical composition. In certain embodiments, the filler is present in the solid pharmaceutical composition in an amount from about 20% to about 50% by weight (w/w) of the solid pharmaceutical composition. In certain embodiments, the filler is present in the solid pharmaceutical composition in an amount from about 30% to about 45% by weight (w/w) of the solid pharmaceutical composition.

In certain embodiments, the solid pharmaceutical compositions comprising Compound A or a pharmaceutically acceptable salt thereof include a pH modifying agent.

In certain embodiments, the pH modifying agent is present in the solid pharmaceutical composition in an amount from about 3% to about 50% by weight (w/w) of the solid pharmaceutical composition. In some such embodiments, the pH modifying agent is present in an amount wherein the weight ratio of Compound A, or salt thereof to the pH modifying agent is from about 1:1 to about 10:1. Alternatively the ratio is from about 2:1 to about 10:1. Alternatively, the ratio is from about 2:1 to about 8:1. Alternatively, the ratio is from about 2:1 to about 6:1. Alternatively, the ratio is from about 2:1 to about 4:1. Alternatively the ratio is from about 2:1 to about 1:1.

In certain embodiments, the weight ratio of Compound A or a pharmaceutically acceptable salt thereof to the pH modifying agent is from about 1:1 to about 10:1. In certain embodiments, the weight ratio of Compound A or a pharmaceutically acceptable salt thereof to the pH modifying agent is from about 2:1 to about 3:1. In certain embodiments, the weight ratio of Compound A or a pharmaceutically acceptable salt thereof to the pH modifying agent is about 2:1.

In certain embodiments, the pH modifying agent comprises sodium acetate, sodium bicarbonate, sodium carbonate, sodium hydrogen carbonate, sodium phosphate, potassium carbonate, potassium hydrogen carbonate, potassium phosphate, magnesium acetate, magnesium bicarbonate, magnesium carbonate, magnesium phosphate, or combinations thereof.

In certain embodiments, the pH modifying agent is sodium carbonate, such as sodium carbonate monohydrate or sodium carbonate anhydrous.

In certain embodiments, sodium carbonate is present in the solid pharmaceutical composition in an amount from about 3% to about 50% by weight (w/w) of the solid pharmaceutical composition. In certain embodiments, sodium carbonate is present in the solid pharmaceutical composition in an amount wherein the weight ratio of compound A, or salt thereof, to sodium carbonate, is from about 1:1 to about 10:1. Alternatively the ratio is from about 2:1 to about 10:1. Alternatively, the ratio is from about 2:1 to about 8:1. Alternatively, the ratio is from about 2:1 to about 6:1. Alternatively, the ratio is from about 2:1 to about 4:1. Alternatively the ratio is from about 2:1 to about 1:1.

As used herein, and in the absence of a specific reference to a particular hydrate (or anhydrous) form of sodium carbonate, any amounts, whether expressed in milligrams or as a percentage by weight or as a ratio with another ingredient, should be taken as referring to the amount of sodium carbonate monohydrate.

In certain embodiments, the pH modifying agent comprises weak bases with pKa ≥6, such as arginine, lysine, histidine, or combinations thereof. In certain embodiments, the pH modifying agent comprises polymeric bases, such as poly(meth)acrylate polymers (Eudragit E 100, Eudragit E 12, Eudragit E 5, Eudragit E PO), or combinations thereof. In certain embodiments, the pH modifying agent comprises ionic exchange resins, such as Amberlite IRA96RF, Amberlite IRA 67, or combinations thereof.

In certain embodiments, the disclosed solid pharmaceutical compositions comprise at least one excipient that functions as a glidant. Glidants may include, for example, colloidal silicon dioxide, including highly dispersed silica (Aerosil®) or any other suitable glidant such as animal or vegetable fats or waxes.

In certain embodiments, a glidant is present in the solid pharmaceutical composition in an amount from about 0.1% to about 5% by weight (w/w) of the solid pharmaceutical composition. In certain embodiments, a glidant is present in the solid pharmaceutical composition in an amount from about 0.1% to about 2% by weight (w/w) of the solid pharmaceutical composition. In certain embodiments, a glidant is present in the solid pharmaceutical composition in an amount from about 0.3% to about 3% by weight (w/w) of the solid pharmaceutical composition. In certain embodiments, a glidant is present in the solid pharmaceutical composition in an amount from about 1% to about 3% by weight (w/w) of the solid pharmaceutical composition. In certain embodiments, a glidant is present in the solid pharmaceutical composition in an amount from about 1% to about 2% by weight (w/w) of the solid pharmaceutical composition. In certain embodiments, the solid pharmaceutical composition includes about 1.6% by weight of a glidant. In certain embodiments, the glidant is colloidal silicon dioxide.

In certain embodiments, a glidant is included in an intragranular portion of the solid pharmaceutical composition. In certain embodiments, the intragranular portion of the solid pharmaceutical composition comprises a glidant in an amount from about 0.1% to about 5% by weight (w/w), on the basis of the weight of the total pharmaceutical composition. In certain embodiments, the intragranular portion of the solid pharmaceutical composition comprises a glidant in an amount from about 0.5% to about 3% by weight (w/w), on the basis of the weight of the total pharmaceutical composition. In certain embodiments, the intragranular portion of the solid pharmaceutical composition comprises about 1% by weight (w/w) of a glidant on the basis of the weight of the total pharmaceutical composition.

In certain embodiments, a glidant is included in an extragranular portion of the solid pharmaceutical composition. In certain embodiments, the extragranular portion of the solid pharmaceutical composition comprises a glidant in an amount from about 0.1% to about 5% by weight (w/w), on the basis of the weight of the total pharmaceutical composition. In certain embodiments, the extragranular portion of the solid pharmaceutical composition comprises a glidant in an amount from about 0.5% to about 2% by weight (w/w), on the basis of the weight of the total pharmaceutical composition. In certain embodiments, the extragranular portion of the solid pharmaceutical composition comprises about 0.6% by weight (w/w) of a glidant on the basis of the weight of the total pharmaceutical composition.

In certain embodiments, a glidant is included in both an intragranular portion and an extragranular portion of the solid pharmaceutical composition. In certain embodiments, the intragranular portion of the solid pharmaceutical composition comprises a glidant in an amount from about 0.1% to about 5% by weight (w/w), on the basis of the weight of the total pharmaceutical composition and the extragranular portion of the solid pharmaceutical composition comprises a glidant in an amount from about 0.1% to about 5% by weight (w/w), on the basis of the weight of the total pharmaceutical composition. In certain embodiments, the intragranular portion of the solid pharmaceutical composition comprises a glidant in an amount from about 0.5% to about 3% by weight (w/w), on the basis of the weight of the total pharmaceutical composition and the extragranular portion of the solid pharmaceutical composition comprises a glidant in an amount from about 0.5% to about 2% by weight (w/w), on the basis of the weight of the total pharmaceutical composition. In certain embodiments, the intragranular portion of the solid pharmaceutical composition comprises a glidant in an amount of about 1% by weight (w/w), on the basis of the weight of the total pharmaceutical composition and the extragranular portion of the solid pharmaceutical composition comprises a glidant in an amount of about 0.6% by weight (w/w), on the basis of the weight of the total pharmaceutical composition. In certain embodiments, colloidal silicon dioxide is used as a glidant at a level of about 1.6% weight/weight of the formulation with about 1% added intragranular and about 0.6% added extragranular.

In certain embodiments, the disclosed solid pharmaceutical compositions comprise at least one excipient that functions as a lubricant. Lubricants may include, for example, magnesium and calcium stearates, sodium stearyl fumarate, talc, or any other suitable lubricant.

In certain embodiments, a lubricant is present in the solid pharmaceutical composition in an amount from about 0.1% to about 5% by weight (w/w) of the solid pharmaceutical composition. In certain embodiments, a lubricant is present in the solid pharmaceutical composition in an amount from about 0.3% to about 3% by weight (w/w) of the solid pharmaceutical composition. In certain embodiments, a lubricant is present in the solid pharmaceutical composition in an amount from about 0.5% to about 1.5% by weight (w/w) of the solid pharmaceutical composition. In certain embodiments, the solid pharmaceutical composition includes about 1% by weight of a lubricant. In certain embodiments, the lubricant is magnesium stearate.

In certain embodiments, a lubricant is included in an extragranular portion of the solid pharmaceutical composition. In certain embodiments, the extragranular portion of the solid pharmaceutical composition comprises a lubricant in an amount from about 0.1% to about 5% by weight (w/w), on the basis of the weight of the total pharmaceutical composition. In certain embodiments, the extragranular portion of the solid pharmaceutical composition comprises a lubricant in an amount from about 0.3% to about 3% by weight (w/w), on the basis of the weight of the total pharmaceutical composition. In certain embodiments, magnesium stearate is used as a lubricant and the magnesium stearate is in the extragranular portion.

In certain embodiments, the disclosed solid pharmaceutical compositions comprise at least one excipient that functions as a disintegrant. Disintegrants may include, for example, cross-linked polymers such as cross-linked modified starches, cross-linked polyvinylpyrrolidone, also known as crospovidone, and cross-linked carboxymethyl cellulose, also known as croscarmellose.

In certain embodiments, a disintegrant is present in the solid pharmaceutical composition in an amount from about 0.1% to about 30% by weight (w/w) of the solid pharmaceutical composition. In certain embodiments, a disintegrant is present in the solid pharmaceutical composition in an amount from about 2% to about 8% by weight (w/w) of the solid pharmaceutical composition. In certain embodiments, a disintegrant is present in the solid pharmaceutical composition in an amount from about 4% to about 6% by weight (w/w) of the solid pharmaceutical composition. In certain embodiments, the solid pharmaceutical composition includes about 4.7% by weight of a disintegrant. In certain embodiments, the solid pharmaceutical composition includes about 4.8% by weight of a disintegrant. In certain embodiments, the disintegrant is crospovidone.

In certain embodiments, the solid pharmaceutical composition is a tablet, which may be coated with any suitable coating such as a film coat. A film coat may be used to, for example, contribute to the ease with which the tablet can be swallowed. A film coat may also be employed to improve taste and provide an elegant appearance. The film coat may comprise a polyvinyl alcohol-polyethylene glycol graft copolymer, such as Opadry® II and Kollicoat® IR. The film coat may also comprise talc as an anti-adhesive. The film coat may account for less than about 5% by weight of the weight of the tablet.

In at least one aspect, this disclosure is directed to providing Compound A or a pharmaceutically acceptable salt thereof in a single, stable solid oral dosage form that is pharmacologically efficacious and physically acceptable. The solid oral dosage forms disclosed herein are intended for pharmaceutical use in human subjects. Accordingly, they should be of an appropriate size and weight for oral human administration (e.g., they should have a total weight of less than about 1.6 g), in addition to being therapeutically efficacious. In order to facilitate the intake of such a dosage form by a mammal, the dosage form may be shaped into an appropriate shape such as a round or elongated shape.

The present disclosure provides solid pharmaceutical compositions comprising Compound A or a pharmaceutically acceptable salt thereof formulated in a solid dispersion. In certain embodiments, the solid dispersion comprises a pharmaceutically acceptable meltable binder. In certain embodiments, the salt of Compound A is the monosodium salt (sodium 4-((R)-2-[5-(2-fluoro-3-methoxy-phenyl)-3-(2-fluoro-6-trifluoromethyl-benzyl)-4-methyl-2,6-dioxo-3,6-dihydro-2H-pyrimidin-1-yl]-1-phenyl-ethylamino)butanoate). In some such embodiments, the salt of Compound A is amorphous sodium 4-((R)-2-[5-(2-fluoro-3-methoxy-phenyl)-3-(2-fluoro-6-trifluoromethyl-benzyl)-4-methyl-2,6-dioxo-3,6-dihydro-2H-pyrimidin-1-yl]-1-phenyl-ethylamino) butanoate.

In certain embodiments, the solid pharmaceutical composition is a tablet which comprises a solid matrix, such as amorphous solid dispersion, wherein the solid matrix, such as the amorphous solid dispersion comprises (i) Compound A or a pharmaceutically acceptable salt thereof and (ii) a pharmaceutically acceptable meltable binder. In some such embodiments, Compound A or the pharmaceutically acceptable salt thereof is the monosodium salt of Compound A (sodium 4-((R)-2-[5-(2-fluoro-3-methoxy-phenyl)-3-(2-fluoro-6-trifluoromethyl-benzyl)-4-methyl-2,6-dioxo-3,6-dihydro-2H-pyrimidin-1-yl]-1-phenyl-ethylamino)butanoate). In some such embodiments the pharmaceutically acceptable meltable binder is polyethylene glycol, such as PEG 3350. In certain embodiments, the solid matrix or the amorphous solid dispersion further comprises a glidant. The glidant and the disintegrant may be physically mixed in a multiple phase matrix. In some such embodiments, the glidant is silicon dioxide. In certain embodiments, the solid matrix, such as amorphous solid dispersion further comprises a disintegrant. In some such embodiments, the disintegrant is crospovidone.

In certain embodiments, the solid pharmaceutical composition of the invention is a tablet comprising (i) an amount of Compound A or a pharmaceutically acceptable salt thereof and (ii) a pharmaceutically acceptable meltable binder. In some such embodiments, the amount of Compound A or a pharmaceutically acceptable salt thereof is about 200 mg. In some such embodiments, the amount of Compound A or a pharmaceutically acceptable salt thereof is about 300 mg. In some such embodiments, Compound A or the pharmaceutically acceptable salt thereof is the monosodium salt of Compound A (e.g., present in the tablet in an amount of about 207 mg or in an amount of about 310 mg). High drug loading is a particular challenge for this drug substance, which is a unique challenge while formulating. In certain embodiments, the solid pharmaceutical composition comprises a solid matrix, such as amorphous solid dispersion. In some such embodiments, at least a portion of the amount of Compound A or a pharmaceutically acceptable salt thereof is molecularly dispersed in the solid matrix, such as amorphous solid dispersion. In some such embodiments, at least a portion of the amount of Compound A or a pharmaceutically acceptable salt thereof is mixed with the solid matrix, such as amorphous solid dispersion. In some such embodiments, a pH modifying agent is mixed with the solid matrix, such as amorphous solid dispersion. In certain embodiments, the solid matrix, such as amorphous solid dispersion further comprises a glidant. In some such embodiments, the glidant is silicon dioxide. In certain embodiments, the solid matrix, such as amorphous solid dispersion further comprises a disintegrant. In some such embodiments, the disintegrant is crospovidone. In certain embodiments, Compound A or the pharmaceutically acceptable salt thereof is the monosodium salt of Compound A (sodium 4-((R)-2-[5-(2-fluoro-3-methoxy-phenyl)-3-(2-fluoro-6-trifluoromethyl-benzyl)-4-methyl-2,6-dioxo-3,6-dihydro-2H-pyrimidin-1-yl]-1-phenyl-ethylamino)butanoate). In certain embodiments the pharmaceutically acceptable meltable binder is polyethylene glycol, such as PEG 3350.

For example, as set forth in Table 1 and Table 2, the disclosed solid pharmaceutical compositions may include one or more fillers, disintegrants, glidants and/or lubricants in combination with the active agent and the pharmaceutically acceptable meltable binder.

Compound A referenced in Table 1 and Table 2 below is Compound A sodium salt and the corresponding weight percent is provided based on that salt form.

TABLE 1

Exemplary Formulations.

| Ingredient | Function | Quantity (mg/Tablet) | %$^a$ (w/w) | %$^b$ (w/w) | Quantity (mg/Tablet) | %$^a$ (w/w) | %$^b$ (w/w) |
|---|---|---|---|---|---|---|---|
| Tablet Core Intragranular | | | | | | | |
| Compound A, sodium salt | Drug Substance | 207.0 | 59.6 | 58.7 | 310.5 | 59.6 | 58.7 |
| Polyethylene glycol 3350, NF | Binder | 16.7 | 4.8 | 4.7 | 25.0 | 4.8 | 4.7 |
| Crospovidone, NF | Disintegrant | 16.7 | 4.8 | 4.7 | 25.0 | 4.8 | 4.7 |
| Sodium carbonate monohydrate, NF | pH modifying agent | 103.5 | 29.8 | 29.4 | 155.25 | 29.8 | 29.4 |
| Colloidal Silicon Dioxide, NF | Glidant | 3.5 | 1.0 | 1.0 | 5.25 | 1.0 | 1.0 |
| Weight subtotal of intragranular components | | 347.3 | 100 | — | 521.0 | | 100 |
| Extragranular | | | | | | | |
| Colloidal Silicon Dioxide, NF | Glidant | 2.0 | — | 0.6 | 3 | — | 0.6 |
| Magnesium stearate, NF | Lubricant | 3.3 | — | 1.0 | 5 | — | 1.0 |
| Uncoated tablet weight | | 352.7 | — | 100 | 529.0 | | — |

$^a$Percents given based on the weight of intragranular components. Total percentage may not be 100% due to rounding.

$^b$Percents given based on the uncoated tablet weight. Total percentage may not be 100% due to rounding.

TABLE 2

Exemplary Formulation (containing a filler).

| Ingredient | Function | Quantity (mg/Tablet) | %$^a$ (w/w) | %$^b$ (w/w) |
|---|---|---|---|---|
| Tablet Core Intragranular | | | | |
| Compound A, sodium salt | Drug Substance | 310.5 | 59.6 | 51.8 |
| Polyethylene glycol 3350, NF | Binder | 25.0 | 4.8 | 4.2 |
| Crospovidone, NF | Disintegrant | 25.0 | 4.8 | 4.2 |
| Sodium carbonate monohydrate, NF | pH modifying agent | 155.25 | 29.8 | 25.9 |

TABLE 2-continued

Exemplary Formulation (containing a filler).

| Ingredient | Function | Quantity (mg/Tablet) | %$^a$ (w/w) | %$^b$ (w/w) |
|---|---|---|---|---|
| Colloidal Silicon Dioxide, NF | Glidant | 5.25 | 1.0 | 0.9 |
| Weight subtotal of intragranular components | | 521.0 | 100 | — |
| Extragranular | | | | |
| Mannitol | Filler | 70.0 | — | 11.7 |
| Colloidal Silicon Dioxide, NF | Glidant | 3.0 | — | 0.5 |
| Magnesium stearate, NF | Lubricant | 6.0 | — | 1.0 |
| Uncoated tablet weight | | 600.0 | — | 100 |

$^a$Percents given based on the weight of intragranular components. Total percentage may not be 100% due to rounding.
$^b$Percents given based on the uncoated tablet weight. Total percentage may not be 100% due to rounding.

The amount (mg) of Compound A or pharmaceutically acceptable salt thereof referenced in the following tables refers to the amount (mg) of Compound A free form (i.e., in the case of a pharmaceutically acceptable salt, the free form equivalent weight).

In certain embodiments, the solid pharmaceutical composition comprises:

| Ingredient | Amount (mg) |
|---|---|
| Compound A or pharmaceutically acceptable salt thereof | 180-330 |
| Polyethylene glycol | 15-40 |
| Crospovidone | 0.2-110 |
| Sodium Carbonate | 50-210 |
| Silicon dioxide | 0.2-10 |
| Magnesium Stearate | 0.2-10 |

In certain embodiments, the solid pharmaceutical composition comprises:

| Ingredient | Amount (mg) |
|---|---|
| Compound A or pharmaceutically acceptable salt thereof | 180-220 |
| Polyethylene glycol | 15-19 |
| Crospovidone | 15-19 |
| Sodium Carbonate | 90-110 |
| Silicon dioxide | 5-6 |
| Magnesium Stearate | 3-4 |

In certain embodiments, the solid pharmaceutical composition comprises:

| Ingredient | Amount (mg) |
|---|---|
| Compound A or pharmaceutically acceptable salt thereof | 270-330 |
| Polyethylene glycol | 22-28 |
| Crospovidone | 22-28 |
| Sodium Carbonate | 135-165 |
| Silicon dioxide | 7-9 |
| Magnesium Stearate | 4-6 |

In certain embodiments, the solid pharmaceutical composition comprises:

| Ingredient | Amount (mg) |
|---|---|
| Compound A or pharmaceutically acceptable salt thereof | 200 |
| Polyethylene glycol | 16.7 |
| Crospovidone | 16.7 |
| Sodium Carbonate | 103.5 |
| Silicon dioxide | 5.5 |
| Magnesium Stearate | 3.3 |

In certain embodiments, the solid pharmaceutical composition comprises:

| Ingredient | Amount (mg) |
|---|---|
| Compound A or pharmaceutically acceptable salt thereof | 300 |
| Polyethylene glycol | 25 |
| Crospovidone | 25 |
| Sodium Carbonate | 155 |
| Silicon dioxide | 8.3 |
| Magnesium Stearate | 5 |

D. METHODS OF MANUFACTURE

The disclosed solid pharmaceutical compositions may be prepared by any suitable method. In certain embodiments, the solid pharmaceutical formulation is manufactured by melt-processing, such as by melt granulation. Melt-processing may be carried out by mixing and heating Compound A or a pharmaceutically acceptable salt thereof and one or more excipients, such as a pharmaceutically acceptable meltable binder, to obtain a homogenous moldable mass and then cooling the melt until it solidifies. The melt can be milled or cut into pieces, either before (e.g., hot-cut) or after solidification (e.g., cold-cut).

"Melting" or "meltable" means a transition into a liquid or rubbery state in which it is possible for one component to become embedded, preferably homogeneously embedded, in the other component or components. Melting usually involves heating above the softening point of the binder(s). In certain embodiments, the active ingredient is miscible with the pharmaceutically acceptable meltable binder. In some such embodiments, the active ingredient becomes molecularly dispersed within the meltable binder. In certain embodiments, the active ingredient is only partially miscible with the pharmaceutically acceptable meltable binder. In some such embodiments, the active ingredient becomes molecularly dispersed within the meltable binder, or partially molecularly dispersed within the meltable binder and/ or also is mixed with the meltable binder.

In certain embodiments, one or more additional excipients are miscible with the pharmaceutically acceptable meltable binder. In some such embodiments, at least one additional excipient is mixed with the meltable binder. In one embodiment, the additional excipient may be molecularly dispersed with the meltable binder. In certain embodiments, at least one additional excipient is only partially miscible or immiscible with the pharmaceutically acceptable meltable binder. In some such embodiments, at least one additional excipient is mixed with the meltable binder.

The melting and/or mixing can take place in an apparatus customary for this purpose, such as high-shears mixer, extruders, injection molders, spray congealers and 3-D printers. Particularly suitable apparatuses are extruders or kneaders. Suitable extruders include single screw extruders, intermeshing screw extruders or multiscrew extruders, preferably twin screw extruders, which can be corotating or counter-rotating and, optionally, be equipped with kneading disks. It will be appreciated that the working temperatures will be determined by the kind of extruder or the kind of configuration within the extruder that is used. Part of the energy needed to melt, mix and dissolve the components in the extruder can be provided by heating elements. However, the friction and shearing of the material in the extruder may also provide a substantial amount of energy to the mixture and aid in the formation of a homogeneous melt of the components.

The preparation of the melt can take place in a variety of ways. The mixing of the components can take place before, during or after the formation of the melt. For example, the components can be mixed first and then melted or be simultaneously mixed and melted. The melt can also be homogenized in order to disperse the active ingredient(s) efficiently. In addition, it may be convenient first to melt the polymer(s) and then to mix in and homogenize the active ingredient(s). Various additives can also be included in the melt, for example, pH modifying agents, glidants, disintegrants, and/or fillers.

In certain embodiments, the solidified melt-processed product is further milled, ground or otherwise reduced to granules. In some such embodiments, the melt-processed product, as well as each granule produced, comprises a solid dispersion comprising the active ingredient and the pharmaceutically acceptable meltable binder. In some such embodiments, the melt-processed product, as well as each granule produced, comprises a solid dispersion comprising the active ingredient and the pharmaceutically acceptable meltable binder. In some such embodiments, the melt-processed product, as well as each granule produced, comprises a solid dispersion comprising the active ingredient and polyethylene glycol (PEG) such as PEG 3350. In some such embodiments, the melt-processed product, as well as each granule produced, comprises a solid dispersion comprising the active ingredient, the pharmaceutically acceptable meltable binder, and a disintegrant. In some such embodiments, the melt-processed product, as well as each granule produced, comprises a solid dispersion comprising the active ingredient, polyethylene glycol (PEG) such as PEG 3350, and a disintegrant.

In certain embodiments, a melt-processed product is blended with other excipient(s) or additive(s) before being milled or ground to granules. In certain embodiments, a melt-processed product is blended with other excipient(s) or additive(s) after being milled or ground to granules. For example, a melt-processed product may be milled and then blended with a glidant and/or a lubricant.

In one example, API, polyethylene glycol, a pH modifying agent, a disintegrant, and a lubricant are blended and then subject to melt-processing. The product thus produced can be milled and, optionally blended with further excipient(s).

A solid matrix, such as amorphous solid dispersion can be prepared by a variety of techniques such as, without limitation, melt-processing, spray-drying, fluid bed granulation co-precipitation, freeze drying, or other solvent evaporation techniques, with melt-processing being preferred.

As disclosed herein, one obstacle to the development of a high drug load formulation was obtaining a formulation with adequate compressibility. In certain embodiments, the pharmaceutical composition is a tablet manufactured by melt-processing. In some such embodiments, melt-processing accommodates the flow properties of the API without compromising the compressibility of the final formulation.

E. METHODS OF USE

In at least one aspect, the present invention includes a method of treating endometriosis comprising administering to a patient a pharmaceutical composition comprising Compound A or a pharmaceutically acceptable salt thereof. In certain embodiments, the method of treating endometriosis comprises administration of a pharmaceutical composition comprising Compound A or a pharmaceutically acceptable salt thereof at a dose of about 150 mg. In some such embodiments, the composition is administered once per day ("QD"). In certain embodiments, the method of treating endometriosis comprises administration of a pharmaceutical composition comprising Compound A or a pharmaceutically acceptable salt thereof at a dose of about 200 mg. In some such embodiments, the composition is administered twice per day ("BID"). In certain embodiments, the method of treating endometriosis comprises administration of a pharmaceutical composition comprising Compound A or a pharmaceutically acceptable salt thereof at a dose of about 300 mg. In some such embodiments, the composition is administered twice per day ("BID"). In certain embodiments, the method of treating endometriosis comprises administration of a pharmaceutical composition comprising Compound A or a pharmaceutically acceptable salt thereof at a dose of about 600 mg. In some such embodiments, the composition is administered once per day ("QD").

In at least one aspect, the present invention includes a method of treating uterine fibroids comprising administering to a patient a pharmaceutical composition comprising Compound A or a pharmaceutically acceptable salt thereof. In certain embodiments, the method of treating uterine fibroids comprises administration of a pharmaceutical composition comprising Compound A or a pharmaceutically acceptable salt thereof at a dose of about 150 mg. In some such embodiments, the composition is administered QD. In certain embodiments, the method of treating uterine fibroids comprises administration of a pharmaceutical composition comprising Compound A or a pharmaceutically acceptable salt thereof at a dose of about 200 mg. In some such embodiments, the composition is administered BID. In certain embodiments, the method of treating uterine fibroids comprises administration of a pharmaceutical composition comprising Compound A or a pharmaceutically acceptable salt thereof at a dose of about 300 mg. In some such embodiments, the composition is administered BID. In certain embodiments, the method of treating uterine fibroids comprises administration of a pharmaceutical composition comprising Compound A or a pharmaceutically acceptable salt thereof at a dose of about 600 mg. In some such embodiments, the composition is administered QD.

In certain embodiments, any of the above methods further comprise administering to the subject a hormone to reduce or alleviate potential side effects of Compound A or a pharmaceutically acceptable salt thereof. For example, the method may comprise administration of an estrogen, a progestin, or a combination thereof. Such treatments are commonly referred to as "add-back" therapy.

In some such embodiments, the add-back therapy comprises a progestogen, such as a progestin. In some such embodiments, the add-back therapy comprises an estrogen. In some such embodiments, the add-back therapy comprises a progestin and an estrogen.

The estrogen and/or progestogen can be administered orally, transdermally or intravaginally. Suitable progestogens for use in the add-back therapy include, for example, progesterone, norethindrone, norethindrone acetate, norgestimate, drospirenone, and medroxyprogestogen. Suitable estrogens for use in the add-back therapy include, for example, estradiol, ethinyl estradiol, and conjugated estrogens. Combined oral formulations containing an estrogen and a progestogen are known in the art and include, for example, Activella®, Angeliq®, FemHRT®, Jenteli™, Mimvey™, Prefest™, Premphase®, and Prempro®.

In certain embodiments, the estrogen is estradiol, ethinyl estradiol, or a conjugated estrogen. In some such embodiments, the estrogen is estradiol. In some such embodiments, the estradiol is administered once a day. In some such embodiments, the dose of estradiol is 0.5 mg. In other such embodiments, the dose of estradiol is 1.0 mg. In some such embodiments, the estrogen is ethinyl estradiol. In some such embodiments, the ethinyl estradiol is administered once a day. In some such embodiments, the dose of ethinyl estradiol is 2.5 mcg. In other such embodiments, the dose of ethinyl estradiol is 5.0 mcg. In some such embodiments, the estrogen is a conjugated estrogen. In some such embodiments, the conjugated estrogen is administered once a day. In some such embodiments, the dose of conjugated estrogen is 0.3 mg. In other such embodiments, the dose of conjugated estrogen is 0.45 mg or 0.625 mg.

In certain embodiments, the progestogen is progesterone, norethindrone, norethindrone acetate, norgestimate, medroxyprogesterone, or drospirenone. In some such embodiments, the progestogen is oral progesterone. In some such embodiments, the oral progesterone is used cyclically (for the last 12 days of the 28-30 day cycle). In some such embodiments, the dose of the oral progesterone is 100 or 200 mg. In some such embodiments, the progestogen is norethindrone or norethindrone acetate. In some such embodiments, the norethindrone or norethindrone acetate is administered once a day. In some such embodiments, the dose of norethindrone or norethindrone acetate is 0.1 mg. In some such embodiments, the dose of norethindrone or norethindrone acetate is 0.5 mg. In some such embodiments, the dose of norethindrone or norethindrone acetate is 1.0 mg. In some such embodiments, the progestogen is norgestimate. In some such embodiments, the norgestimate is administered once a day. In some such embodiments, the dose of norgestimate is 0.09 mg. In some such embodiments, the progestogen is medroxyprogesterone. In some such embodiments, the medroxyprogesterone is administered once a day. In some such embodiments, the dose of medroxyprogesterone is 1.5 mg. In some such embodiments, the dose of medroxyprogesterone is 2.5 mg or 5 mg. In some such embodiments, the progestogen is drospirenone. In some such embodiments, the drospirenone is administered once a day. In some such embodiments, the dose of drospirenone is 0.25 mg. In some such embodiments, the dose of drospirenone is 0.5 mg.

In certain embodiments, the add-back therapy comprises a norethisterone prodrug, such as norethindrone acetate. In some such embodiments, the add-back therapy further comprises estradiol. Thus, in some such embodiments, the add-back therapy comprises estradiol and norethindrone acetate. In some such embodiments, estradiol and norethindrone acetate are administered orally once per day. In some such embodiments, estradiol is administered in an amount of about 0.5 mg and norethindrone acetate is administered in an amount of about 0.1 mg per day. In other such embodiments, estradiol is administered in an amount of about 1.0 mg and norethindrone acetate is administered in an amount of about 0.5 mg per day. Alternatively, in certain embodiments, estradiol is administered continuously and norethindrone acetate is administered once per day during the last 12-14 days of a menstrual cycle.

In certain embodiments, the dose of Compound A or a pharmaceutically acceptable salt thereof is administered twice a day. In some such embodiments, add-back therapy is administered once a day. The administration of Compound A or a pharmaceutically acceptable salt thereof may be prior to, immediately prior to, during, immediately subsequent to or subsequent to the administration of the add-back therapy.

In certain embodiments, a dose of Compound A or pharmaceutically acceptable salt thereof (e.g., 300 mg) is administered in the morning with add-back therapy, such as a combination of an estrogen and a progestogen (e.g., estradiol and norethindrone acetate) and a dose of Compound A or pharmaceutically acceptable salt thereof (e.g., 300 mg) is administered in the evening without add-back therapy.

In certain embodiments, Compound A or a pharmaceutically acceptable salt thereof is co-packaged with the add-back therapy. For example, a blister pack may contain a dose of Compound A or a pharmaceutically acceptable salt thereof and a dose of the add-back therapy.

In certain embodiments, Compound A or a pharmaceutically acceptable salt thereof is present in a fixed dose combination with the add-back therapy. For example, a capsule may contain a caplet or tablet comprising Compound A or a pharmaceutically acceptable salt thereof and a caplet or tablet comprising the add-back therapy, such as a combination of an estrogen and a progestogen (e.g., estradiol and norethindrone acetate). In some such embodiments, the capsule comprises 300 mg Compound A or a pharmaceutically acceptable salt thereof, 1 mg estradiol, and 0.5 mg norethindrone acetate.

The pharmaceutical compositions, methods, and uses described herein will be better understood by reference to the following exemplary embodiments and examples, which are included as an illustration of and not a limitation upon the scope of the invention.

F. EXAMPLES

The following Examples demonstrate certain challenges encountered during formulation development and describe formulations that overcome those challenges.

Example 1: Formulations F1 and F2

Table 3 presents additional non-limiting examples of components of the disclosed formulations and their percentage by weight (w/w) of the formulation. Compound A referenced in the table below is the Compound A sodium salt and the corresponding weight percent is provided based on that salt form.

TABLE 3

Composition of Formulations F1 and F2

| | | Formulation F1 | | Formulation F2 | |
|---|---|---|---|---|---|
| Ingredient | Function | Quantity (mg/Tablet) | %$^a$ (w/w) | Quantity (mg/Tablet) | %$^a$ (w/w) |
| Compound A, sodium salt | Drug Substance | 207.0 | 58.7 | 310.5 | 58.7 |

TABLE 3-continued

Composition of Formulations F1 and F2

| Ingredient | Function | Formulation F1 Quantity (mg/Tablet) | Formulation F1 %$^a$ (w/w) | Formulation F2 Quantity (mg/Tablet) | Formulation F2 %$^a$ (w/w) |
|---|---|---|---|---|---|
| Polyethylene glycol 3350, NF | Binder | 16.7 | 4.7 | 25.0 | 4.7 |
| Crospovidone, NF | Disintegrant | 16.7 | 4.7 | 25.0 | 4.7 |
| Sodium carbonate monohydrate, NF | pH modifying agent | 103.5 | 29.4 | 155.3 | 29.4 |
| Colloidal silicon dioxide, NF | Glidant | 5.5 | 1.6 | 8.3 | 1.6 |
| Magnesium stearate, NF | Lubricant | 3.3 | 1.0 | 5 | 1.0 |
| Uncoated tablet weight | | 352.7 | | 529.0 | |

$^a$Percents given based on the uncoated tablet weight. Total percentage may not be 100% due to rounding.

Figure 2:
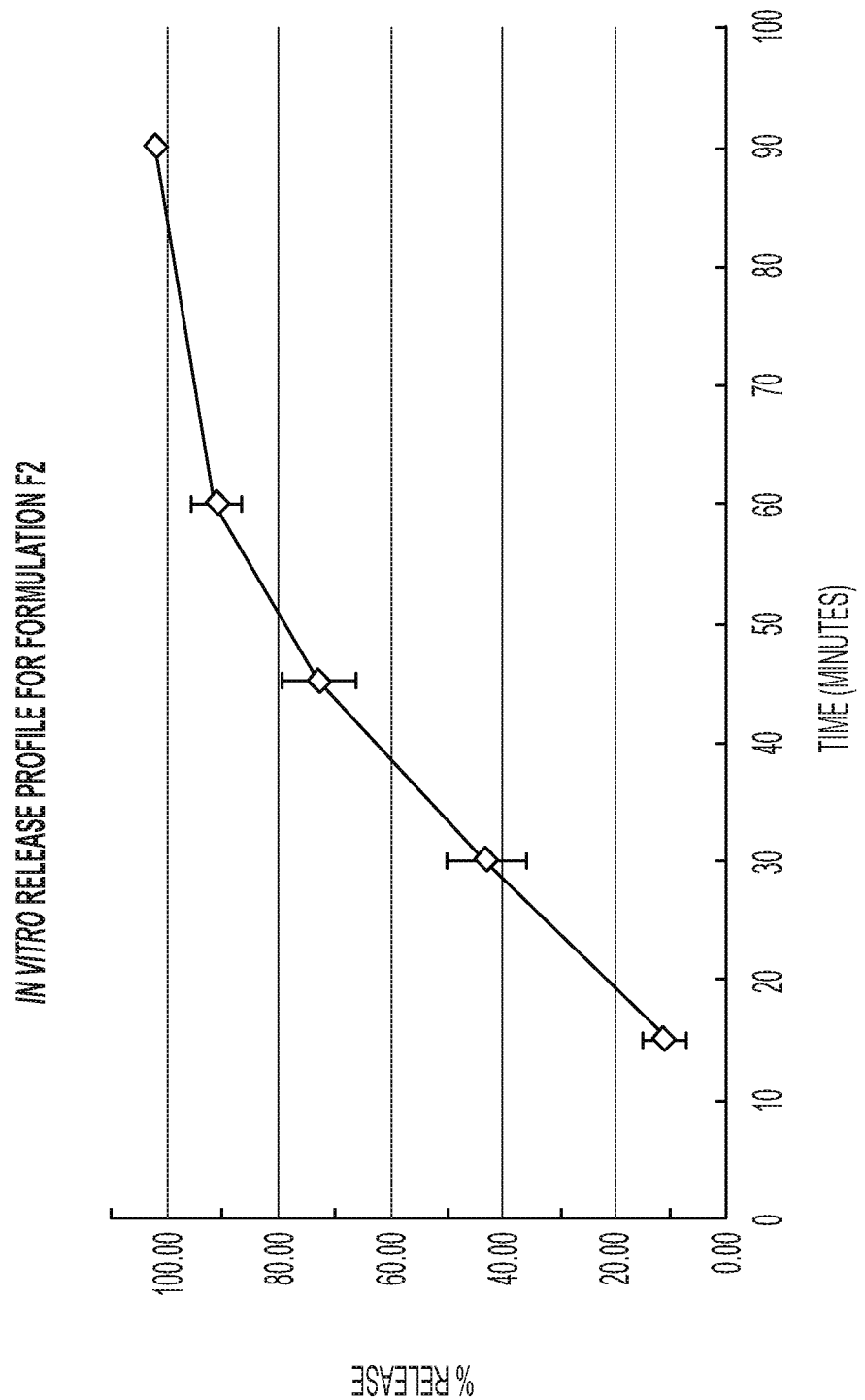
FIG. 2 is a graph showing an in vitro dissolution profile for Formulation F2.
Figure 3:
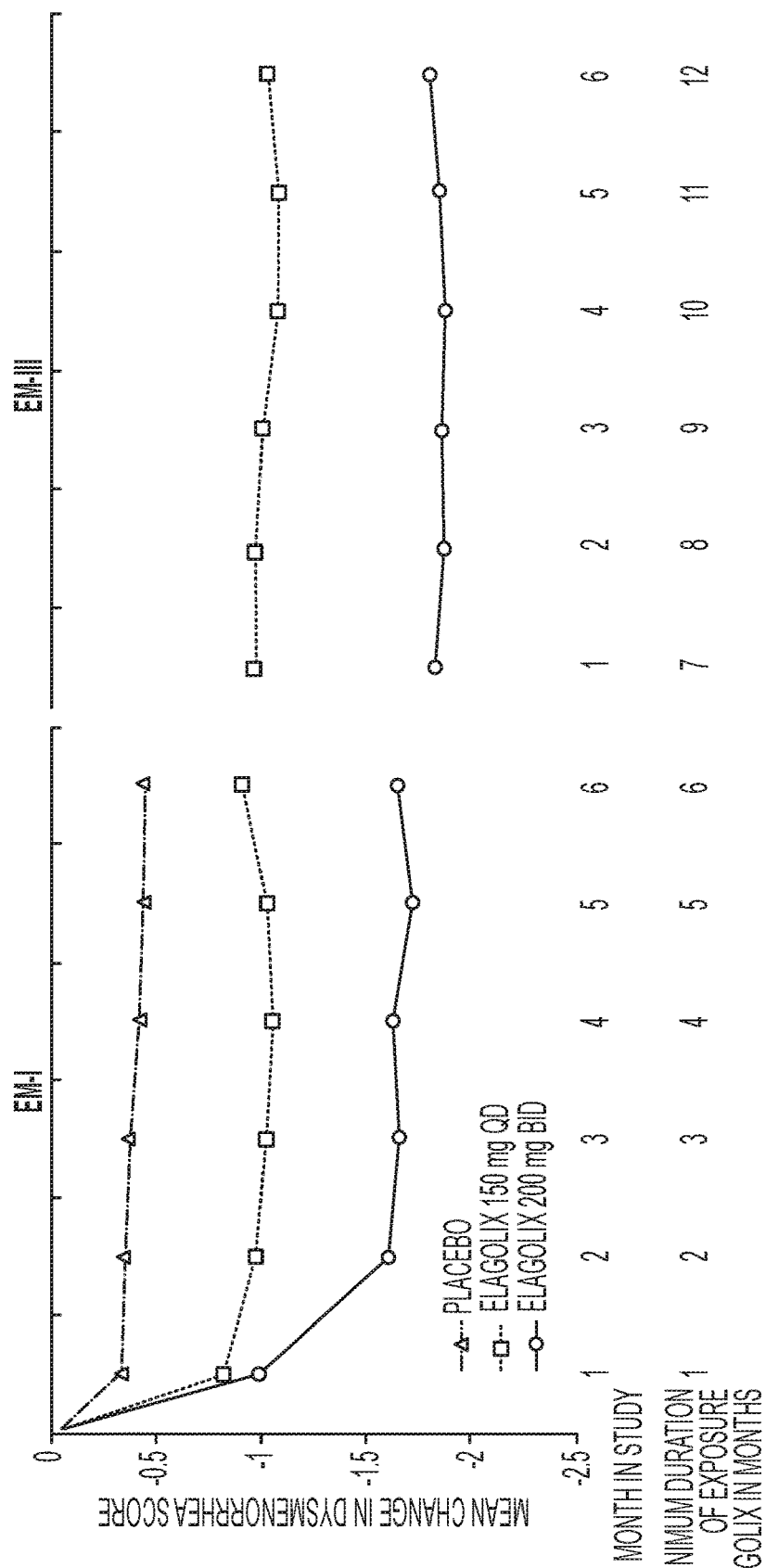
FIG. 3. Mean Change from Baseline in Mean Dysmenorrhea Pain Scores in Study EM-I and Maintenance of Response in its Extension Study EM-III over 12 Months.
Figure 4:
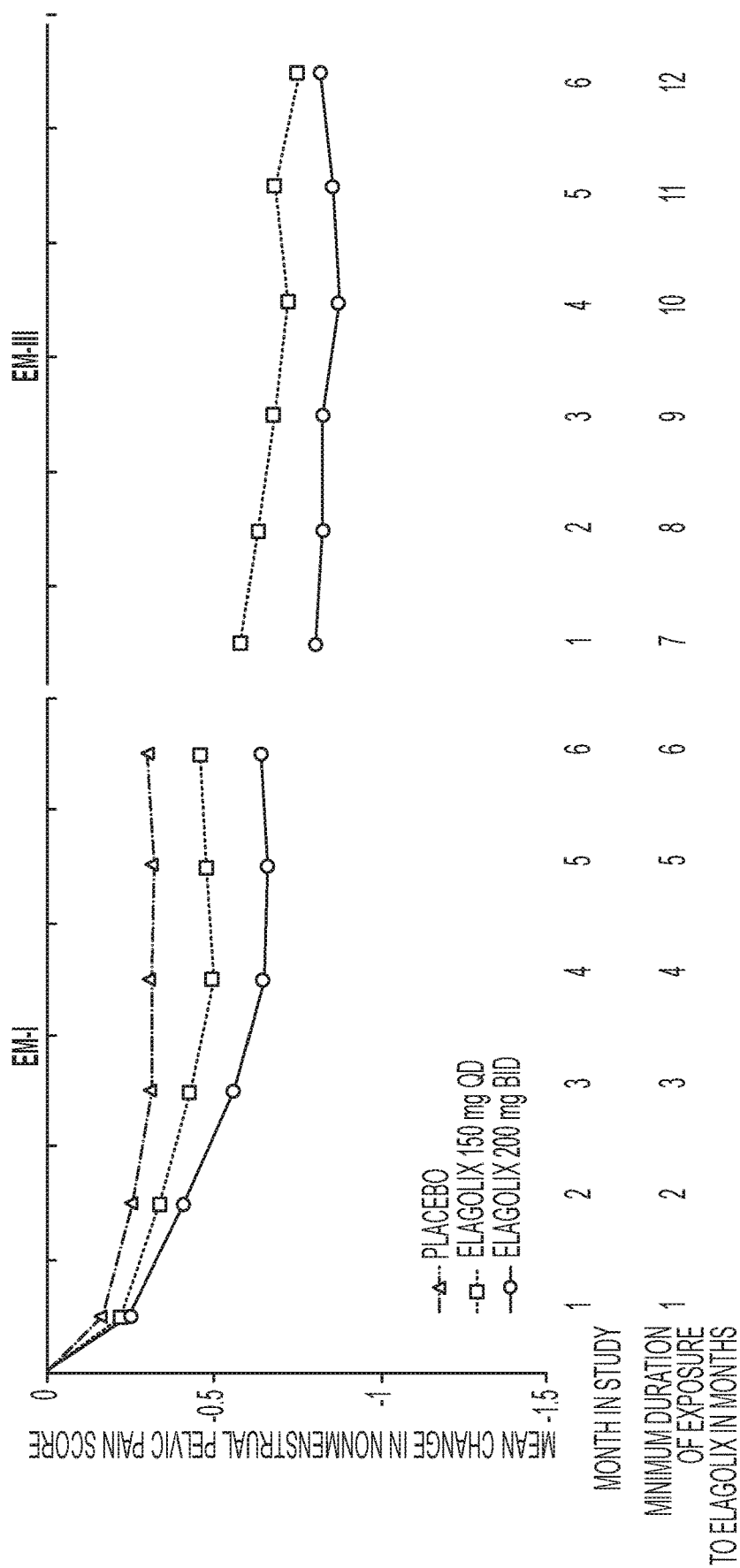
FIG. 4. Mean Change from Baseline in Mean NMPP Scores in Study EM-I and Maintenance of Response in its Extension Study EM-III over 12 Months.
Figure 5:
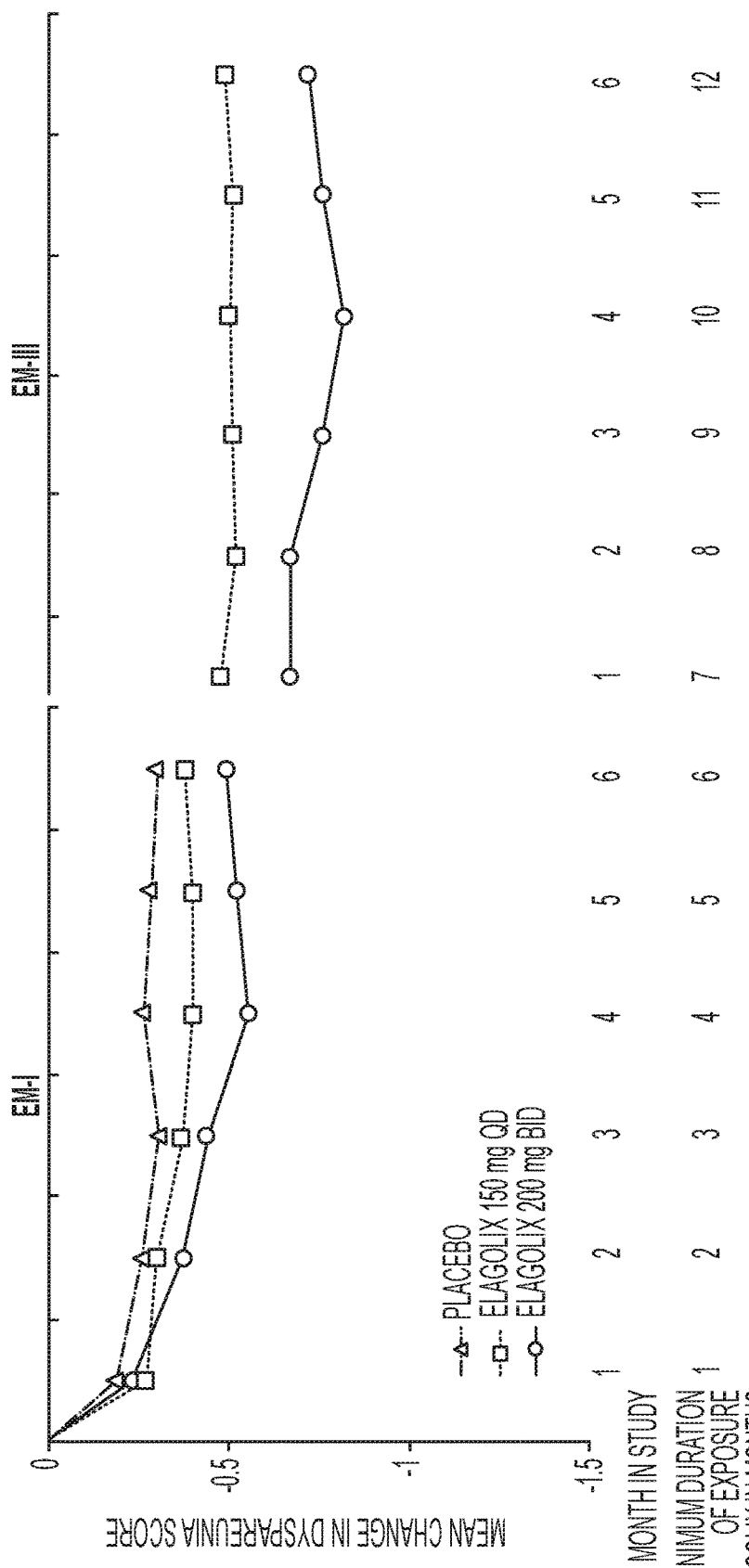
FIG. 5. Mean Change from Baseline in Mean Dyspareunia Pain Scores in Study EM-I and Maintenance of Response in its Extension Study EM-III over 12 Months
Figure 6:
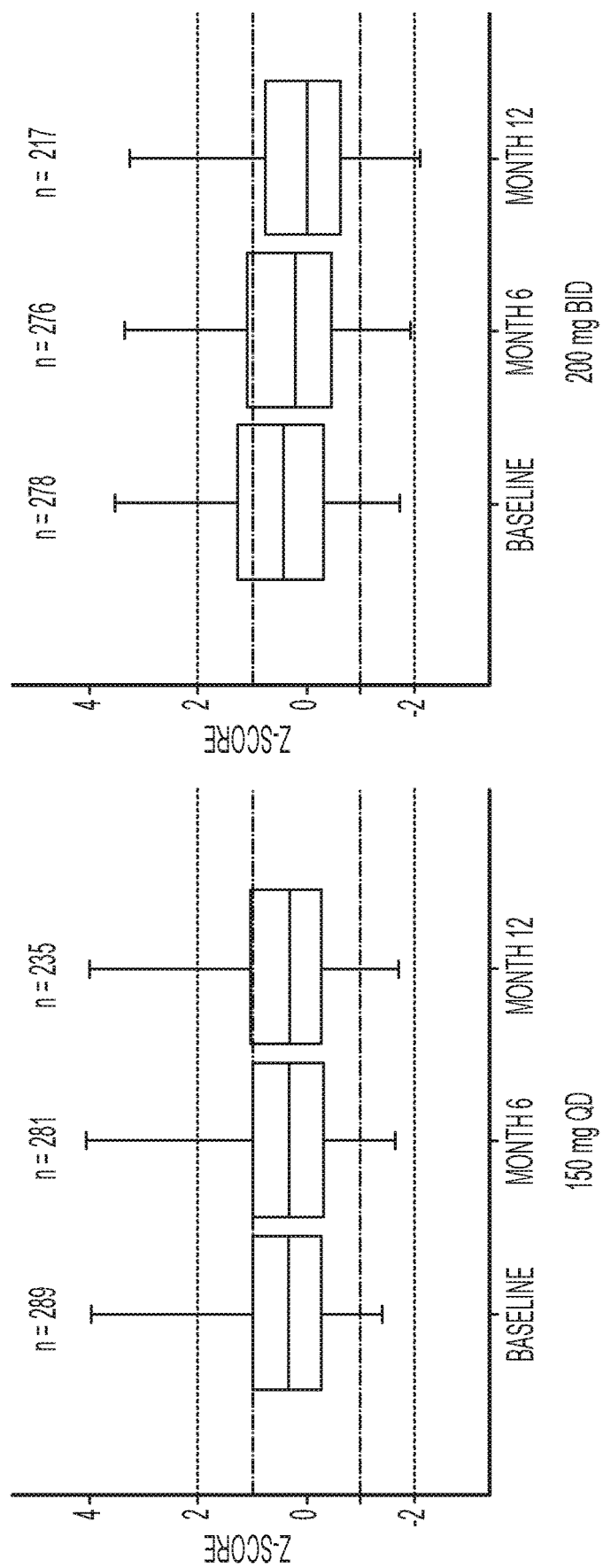
FIG. 6: Lumbar Spine BMD Z-score Box Plots at Baseline, Month 6 and Month 12 for Elagolix 150 mg QD and 200 mg BID.
Figure 7:
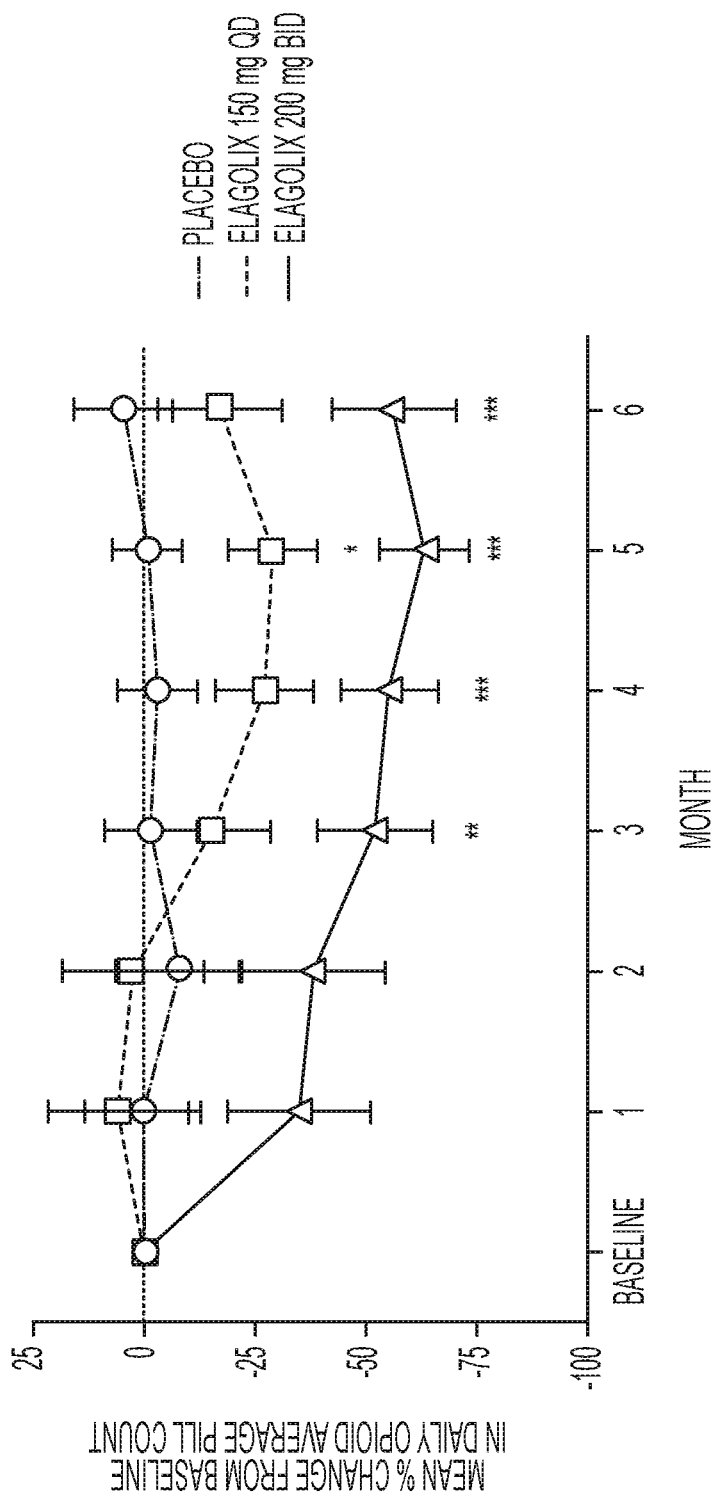
FIG. 7: Depicts rescue opioid pill counts results as mean percentage change from baseline. Significance vs. placebo is indicated for $P<0.05$ (*) and $P<0.001$ (***) from an ANCOVA model. Month=35-day interval.

Formulation F2 was tested for dissolution using USP apparatus II in 900 mL of sodium phosphate, pH 6.8, at 37° C. and paddle speed of 50 rpm. The dissolution profile of Formulation F2 tablets are shown in FIG. 2.

Example 2: Study of the Effect of Antigelling Agent on Chemical Stability

To investigate the effects of antigelling (pH modifying) agent on chemical stability of Compound A in the formulations, formulations containing different ratios of Compound A to the antigelling agent, sodium carbonate, were prepared as follows:

TABLE 4

Composition of Exemplary Formulations

| | Components | Formulation (mg) #1 | #2 | #3 | #4 | #5 (Control) |
|---|---|---|---|---|---|---|
| Intra-granular | Compound A | 310 | 310 | 310 | 310 | 310 |
| | Sodium carbonate anhydrate | 31 | 31 | 31 | 31 | 155 |
| | Polyethylene glycol 3350 | 25 | 25 | 25 | 25 | 25 |
| | Crospovidone | 25 | 25 | 25 | 25 | 25 |
| | Silicon dioxide | 5.2 | 5.2 | 5.2 | 5.2 | 5.2 |
| Extra-granular | Sodium carbonate anhydrate | 47 | 21 | 8 | 0 | 0 |
| | Silicon dioxide | 3 | 3 | 3 | 3 | 3 |
| | Magnesium stearate | 5 | 5 | 5 | 5 | 5 |
| | Total | 452 | 426 | 413 | 405 | 529 |
| | Compound A - Sodium carbonate ratio | 10:1 | 8:1 | 6:1 | 4:1 | 2:1 |

95 g Compound A, 9.5 g sodium carbonate anhydrate, 7.66 g polyethylene glycol 3350 and 7.66 g crospovidone were weighed and pre-blended. 1.6 g of silicon dioxide was subsequently added to the powder mixture after being sieved through a 30 mesh screen and blended for an additional 5 minutes. The powder blend was melt granulated using a Thermo Scientific™ Pharma 11 Twin-screw Extruder at 200-600 mg/hr and at 123-124° C. with the screw speed at 400 rpm. The granules were obtained by milling the off-white, opaque extrudate using a Fitzmill with impact forward and a 0.033" round screen at 5000 rpm. The milled granulation was mixed with the remaining sieved silicon dioxide, magnesium stearate and different quantities of sodium carbonate shown in Table x to produce powder blends for Formulations #1-4, respectively. Each individual final blend was compressed into tablet using a Carver press with the compression force at 1000-1400 lbs. The final tablet formulations prepared contain 4:1, 6:1, 8:1 and 10:1 w/w ratio of Compound A to sodium carbonate, respectively. Tablets of the control formulation (#5) with 2:1 w/w ratio of Compound A to sodium carbonate was prepared using the same process steps in a Micro 27 PH twin-screw extruder at pilot scale.

Figure 10:
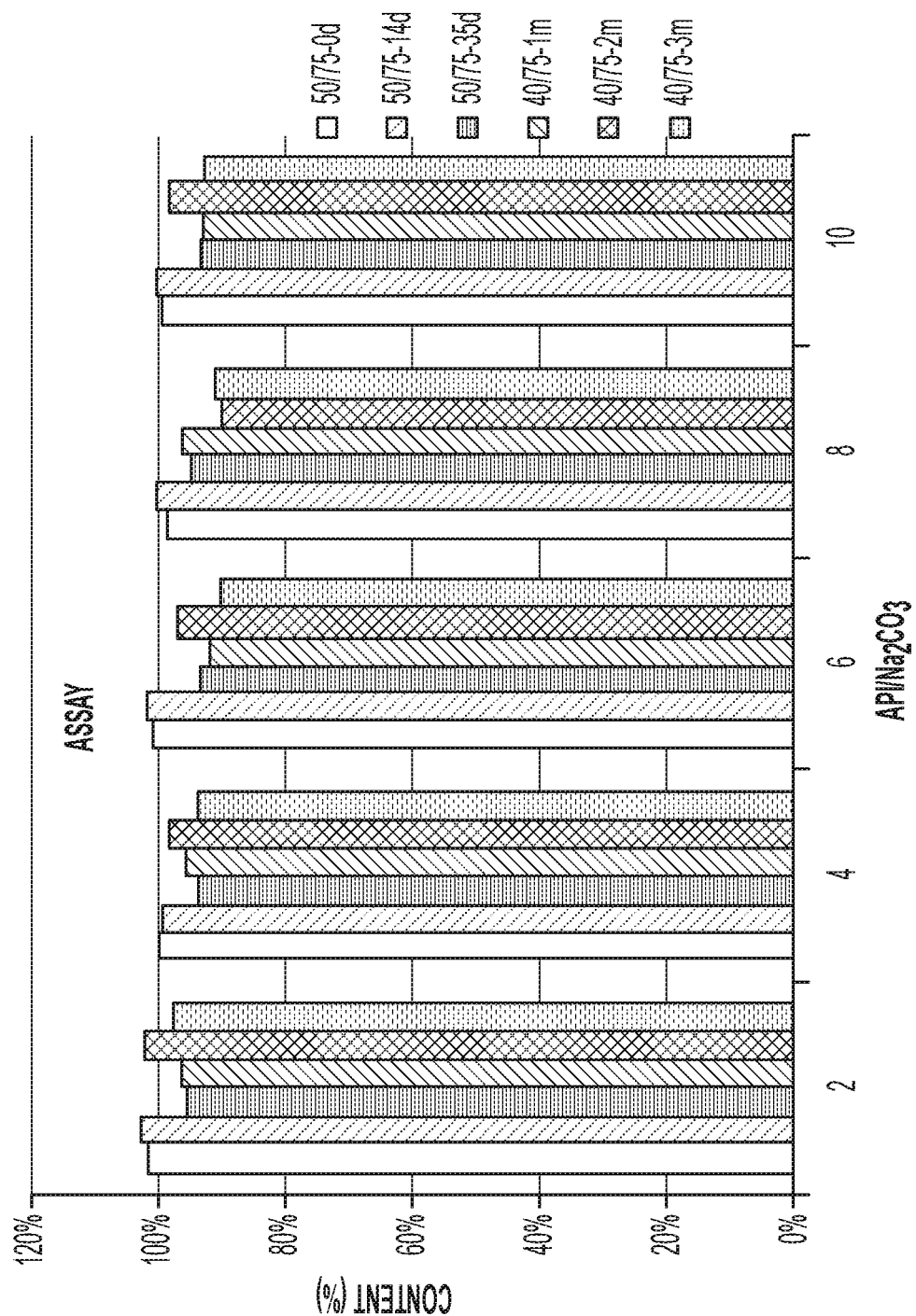
FIG. 10: The stability results are provided for Formulations #1-5. Degradation product, lactam, was used as the indicator of stability performance because it is the most sensitive to pH changes in the formulation. Results of stability studies of Formulations #1-5
Figure 10:
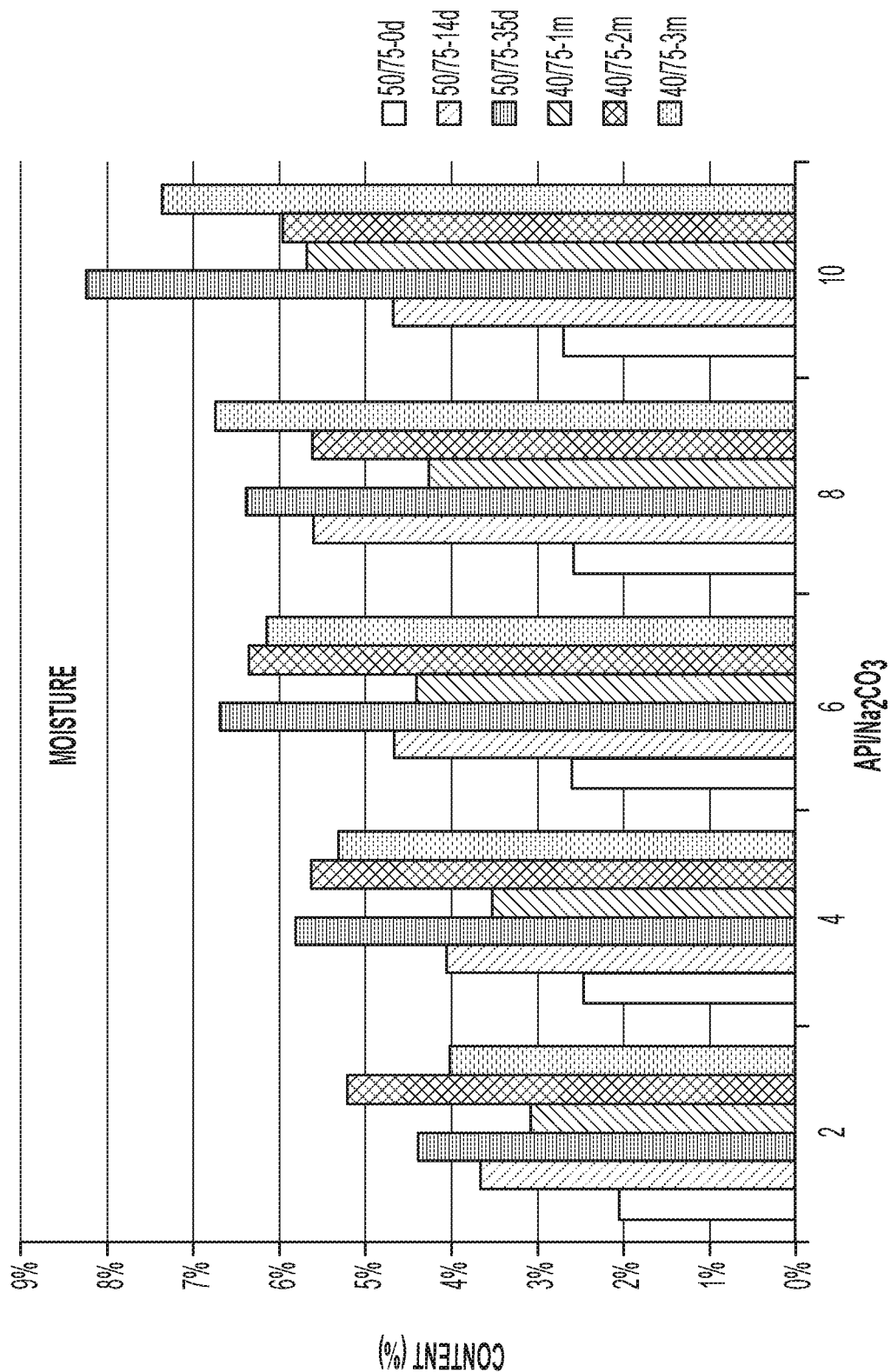

Tablets of Formulations #1-5 were placed in glass scintillation vials with screw caps and stored under stress and accelerated test conditions with elevated temperature and humidity, i.e., 50° C./75% RH or 40° C./75% RH, respectively. Formulation #5 containing 2:1 w/w ratio of Compound A to sodium carbonate anhydrate was used as a control because it has been shown to provide adequate antigelling properties and acceptable long term stability. Tablet samples were taken at predetermined time intervals and analyzed for content, degradation products and moisture content. The stability results are provided in FIG. 10. Degradation product, lactam, was used as the indicator of stability performance because it is the most sensitive to pH changes in the formulation. The study demonstrated acceptable stability of all test tablet formulations comparable with the control formulation despite of the higher moisture contents. At an antigelling agent (sodium carbonate) level as low as 10% of Compound A, the assay results and lactam degradant levels are well within the product specification limits of 90-110% and 0.5%, respectively. One degradation product of Compound A is Compound B, which has a lactam moiety. The lactam moiety may be determined using numerous techniques. In one embodiment, the lactam moiety is determined using reversed phase high performance liquid chromatography (HPLC) with ultraviolet (UV) detection at 275 nm. The HPLC system consists of a C8 column with a flow rate at 1.1 mL/min. The column temperature is kept at 50° C. throughout the analysis. Both mobile phase A and B are applied, where mobile phase A is triethylamine/acetic acid buffer solution with an ratio of water:triethylamines: acetic acid in 100:0.1:0.06 (v/v) at pH 5.3 and mobile phase B is Acetonitrile. The diluent is triethylamine/acetic acid buffer solution and acetonitrile in a 50:50 (v/v) ratio. The detection limit standard is prepared in diluent with an accurately known concentration of about 0.06 pg elagolix free form/mL. The typical relative retention times (RRT) for the lactam moiety is approximately at 1.48 and the normalization factor is (NF) is 1.08.

Example 3: Stability Study of Formulations Comprising Different Antigelling (pH Modifying) Agents To investigate the effects of different antigelling (pH modifying) agents on chemical stability of Compound A in the formulations, formulations containing different ratios of Compound A to the alternate pH modifying agents, Arginine and Eudragit E PO, were prepared as follows:

TABLE 5

Composition of Exemplary Formulations

| Components | Formulation A | Formulation B | Formulation C (Control) |
|---|---|---|---|
| Compound A | 310 | 310 | 310 |
| Arginine | 77.5 | — | — |
| Eudragit E | — | 155 | — |
| Polyethylene glycol 3350 | 25 | 25 | 25 |
| Crospovidone | 25 | 25 | 25 |
| Silicon dioxide | 3 | 3 | 3 |
| Magnesium stearate | 5 | 5 | 5 |
| Total | 445 | 523 | 368 |
| Compound A -pH modifying agent ratio | 4:1 | 2:1 | N/A |

Figure 11:
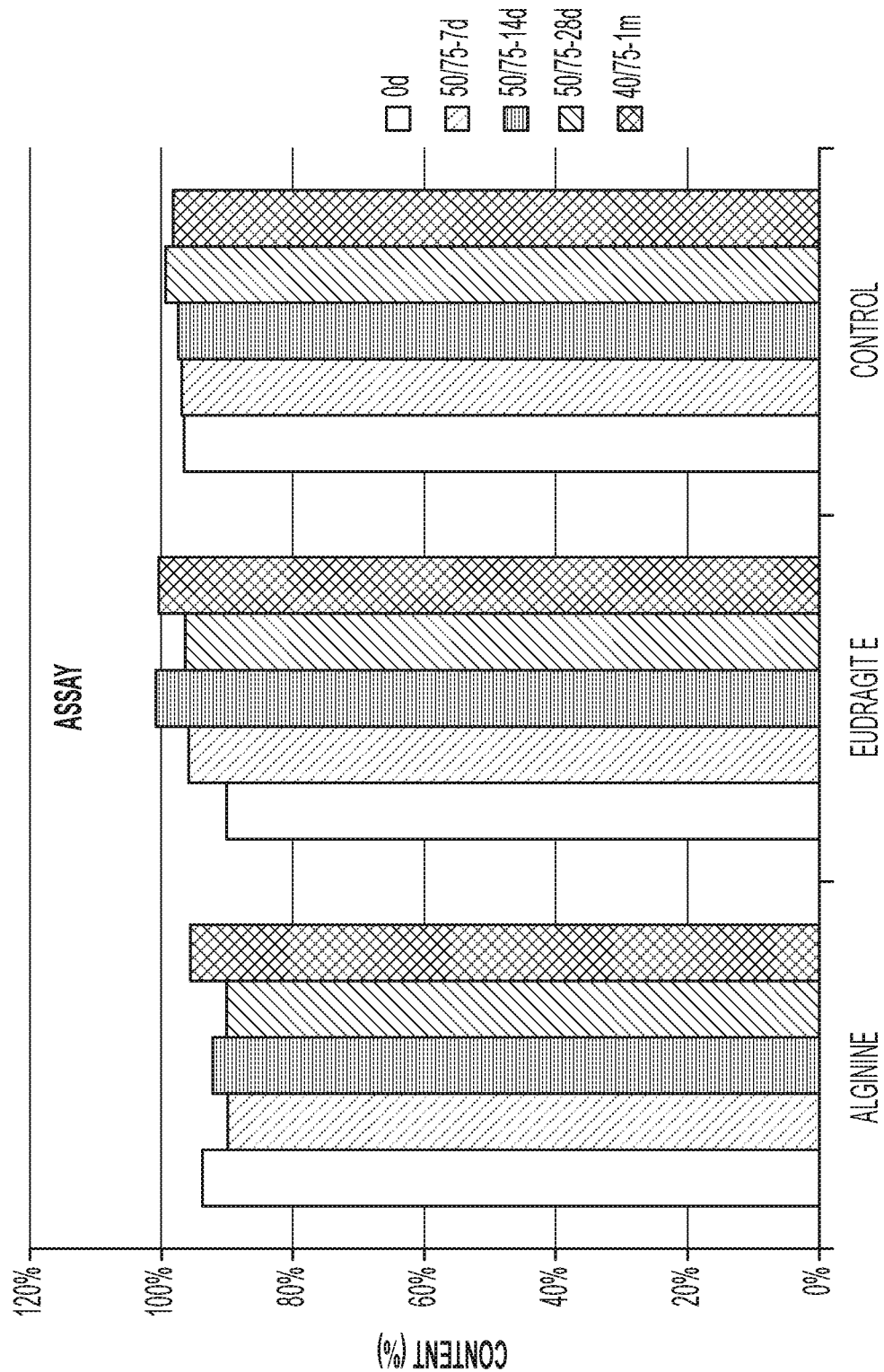
FIG. 11: The stability results are provided for Formulations A and B. Degradation product, lactam, was used as the indicator of stability performance because it is the most sensitive to pH changes in the formulation.
Figure 11:
Figure 11:
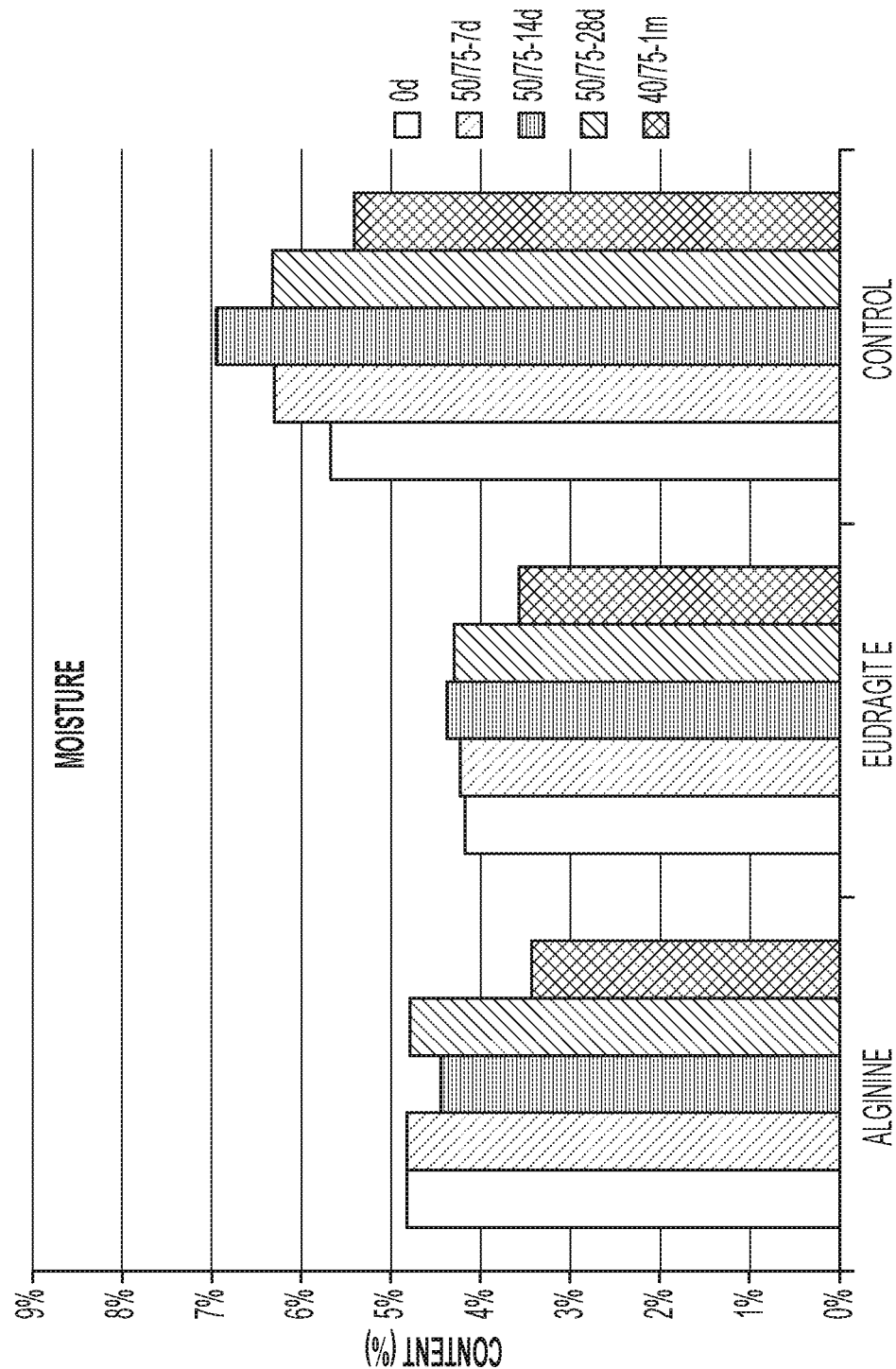

9.3 g Compound A, 0.75 g polyethylene glycol 3350, 0.75 g crospovidone and 2.325 g alginine (Formulation A) or 4.65 g Eudragit E PO (Formulation B) were weighed and pre-blended. 0.09 g of silicon dioxide was subsequently added to the powder mixture after being sieved through a 30 mesh screen and blended for 10 minutes. 0.15 g magnesium stearate was added and blended for an additional one minute. Each powder blend was compressed into tablet using a Carver press with the compression force of 2000 lbs. The final tablets of Formulation A and B contain 4:1 and 2:1 w/w ratio of Compound A to Arginine and Eudragit E, respectively. Formulation C does not contain an antigelling agent. Tablets of Formulations A and B were placed in glass scintillation vials with screw caps and stored under stress and accelerated test conditions with elevated temperature and humidity, i.e., 50° C./75% RH or 40° C./75% RH, respectively. Formulation C containing no pH modifying agent was used as a control. Tablet samples were taken at predetermined time intervals and analyzed for content, degradation products and moisture content. The stability results are provided in FIG. 11. Degradation product, lactam, was used as the indicator of stability performance because it is the most sensitive to pH changes in the formulation.

The study demonstrated acceptable stability of both Formulations A and B, comparable to the control formulation. Using Arginine or Eudragit E as pH modifying agent, changes in the assay results, tablet moisture and lactam degradant levels are similar to those of the control formulation. The lactam levels were well within the product specification limits 0.5%.

Example 4: Pharmacokinetic Parameters of F2

A study was conducted to assess the bioavailability of a single dose of a fixed dose combination of F2, estradiol (E2), and norethindrone acetate (NETA) under fasting conditions. A single capsule containing the 300 mg F2 tablet and a 1 mg/0.5 mg E2/NETA tablet was administered to 36 adult healthy postmenopausal females. The pharmacokinetic parameters are shown in Table 4. Data for $C_{max}$, $AUC_t$, and $AUC_\infty$ are presented as the mean (% CV); data for $T_{max}$ are presented as median (min-max); and data for Ti/2 are presented as harmonic mean (pseudo-sd).

TABLE 6

Pharmacokinetic Parameters of 300 mg F2

| Pharmacokinetic Parameters (units) | F2 300 mg tablet (N = 36) |
|---|---|
| $T_{max}$ (hr) | 1.5 (1.0-3.0) |
| $C_{max}$ (ng/mL) | 1871 (47) |
| $AUC_t$ (ng · hr/mL) | 4718 (44) |
| $AUC_\infty$ (ng · hr/mL) | 4726 (44) |
| $t_{1/2}$ (hr) | 3.0 (0.6) |

Example A-1: Efficacy and Safety of Elagolix in a Subgroup of Women with Uterine Fibroids and Non-Dominant Adenomyosis Adenomyosis is an estrogen-dependent disease of benign endometrial tissue growth within the uterine muscular tissue, and is associated with heavy menstrual bleeding (HMB) and dysmenorrhea. Adenomyosis occurs when endometrial tissue, which normally lines the uterus, exists within and grows into the muscular wall of the uterus. The displaced endometrial tissue continues to act as it normally would thickening, breaking down and bleeding during each menstrual cycle. An enlarged uterus and painful, heavy periods can result. Symptoms most often start late in the childbearing years after having children. The cause of adenomyosis remains unknown, but the disease typically disappears after menopause. For women who experience severe discomfort from adenomyosis, certain treatments can help, but hysterectomy is the only cure. Sometimes, adenomyosis is silent causing no signs or symptoms or only mildly uncomfortable. In other cases, adenomyosis may cause: Heavy or prolonged menstrual bleeding, severe cramping or sharp, knifelike pelvic pain during menstruation (dysmenorrhea), menstrual cramps that last throughout your period and worsen as you get older, pain during intercourse and blood clots that pass during your period.

An analysis of the efficacy and safety of elagolix in a subgroup of women with UF and adenomyosis was conducted.

Patients and Methods: A 6-month, randomized, double-blind, placebo-controlled, 2-cohort, phase 2b clinical trial evaluating the safety and efficacy of elagolix (Cohort 1, 300 mg twice daily [BID] and Cohort 2, 600 mg once daily [QD]), elagolix with 0.5 mg estradiol (E2)/0.1 mg norethindrone acetate (NETA), and elagolix with 1.0 mg E2/0.5 mg NETA in premenopausal women with HMB (≥80 mL/month) and UF was conducted. elagolix studied in this clinical trial comprised the sodium salt of Compound A.

All subjects were evaluated with ultrasound and a subset volunteered to also be evaluated by MRI. Women were excluded from the study if they had evidence of diffuse or segmental adenomyosis as a dominant condition (>50% of the myometrium via ultrasound/MRI). Efficacy and safety were evaluated post hoc in a subgroup of women who had confirmed non-dominant adenomyosis (ultrasound/MRI) at baseline. Menstrual blood loss (MBL) was quantified from sanitary products (alkaline hematin). The composite primary endpoint was the proportion of women who had a ≥50% reduction from baseline in HMB and <80 mL MBL in the last 28 days of treatment. Adverse events (AEs) were recorded.

Results: Of the 567 women treated in the study, 86 women (15%; Cohort 1, n=32; Cohort 2, n=54) had confirmed adenomyosis (ultrasound and/or MRI). The majority (72%) of women with confirmed adenomyosis were Black and 87% had a ≥25 BMI at baseline. The proportion of women in Cohort 1 who had a ≥50% reduction from baseline in HMB and <80 mL menstrual blood loss (MBL) in the last 28 days of treatment were 40% for placebo (n=10), 80% for elagolix 300 mg BID (n=5), 83% for elagolix 300 mg BID with 0.5 mg E2/0.1 mg NETA (n=12), and 100% for elagolix 300 mg BID with 1.0 mg E2/0.5 mg NETA (n=5); and in Cohort 2, 13% for placebo (n=16), 92% for elagolix 600 mg QD (n=13), 93% for elagolix 600 mg QD with 0.5 mg E2/0.1 mg NETA (n=14), and 89% for elagolix 600 mg QD with 1.0 mg E2/0.5 mg NETA (n=9). At least 1 AE, related or unrelated to study drug, was reporting in 90% of the placebo group (n=10) and 77% of elagolix-treated groups (n=22) in Cohort 1 and 88% of the placebo group (n=16) and 67% of the elagolix-treated groups (n=38) in Cohort 2.

Example A-2: Safety and Efficacy of Elagolix in Women with Symptomatic Adenomyosis The safety, efficacy, and tolerability of elagolix 300 mg BID in combination with E2/NETA (estradiol 1 mg/norethindrone acetate 0.5 mg QD), versus Placebo in premenopausal women 18-51 years of age with symptomatic adenomyosis will be assessed in a clinical trial.

Elagolix 300 mg BID equivalent with add-back treatment is expected to reduce heavy menstrual bleeding (HMB) and pelvic pain in women with symptomatic adenomyosis. Other doses of add back and elagolix as previously described may also be used for the treatment of symptomatic adenomyosis.

Various aspects of the evaluation where elagolix may be found to be efficacious and safe may include the following:
(a) Reduction in heavy menstrual bleeding to <80 ml/mo with a >50% reduction from baseline in menstrual blood loss (MBL) at Month 6;
(b) A clinically meaningful decrease (defined as >30% reduction from baseline) in pelvic pain at Month 3. This assessment will take other co-medications, such as analgesic into consideration as well;
(c) Reduction in heavy menstrual bleeding to <80 ml/mo with a >50% reduction from baseline in MBL at Month 3;
(d) Reduction in heavy menstrual bleeding to <80 ml/mo with a >50% reduction from baseline in MBL at Month 12;
(e) A clinically meaningful decrease (defined as >30% reduction) from baseline in pelvic pain at Month 6. This assessment will take other co-medications, such as analgesic into consideration as well;
(f) MBL volume mean change from baseline vs placebo;
(g) Suppression of bleeding as defined by amenorrhea+/− spotting;
(h) Suppression of menstrual cramps that last throughout the menstrual period;
(i) Reduction of pain during intercourse; or
(j) Reduction of blood clots that pass during menstrual period.

Safety evaluations may include physical examination, vital signs, endometrial assessments (endometrial thickness and biopsy), pelvic ultrasound [TAU (Transabdominal Ultrasound)/TVU (Transvaginal Ultrasound)], clinical laboratory tests and adverse events monitoring.

Example A-3: Safety and Efficacy of Elagolix in Endometriosis Related Conditions (I) Elagolix is an orally administered, short-acting, selective, non-peptide small molecule GnRH receptor antagonist that blocks endogenous GnRH signaling by binding competitively to GnRH receptors in the pituitary gland. Administration of elagolix results in dose-dependent suppression of luteinizing hormone (LH) and follicle-stimulating hormone (FSH) levels, leading to decreased blood levels of the ovarian sex hormones, estradiol and progesterone. LH and FSH suppression begins within hours of administration and is readily reversible upon discontinuation of elagolix.

(a) Pharmacodynamics: Effect on Ovulation and Estradiol

During the course of a 3-menstrual cycle study in healthy women, elagolix 150 mg QD and 200 mg BID resulted in an ovulation rate of approximately 50% and 32%, respectively. In the Phase 3 studies in women with endometriosis, partial suppression of estradiol to approximately 50 pg/mL was observed for ELAGOLIX 150 mg QD, whereas nearly full suppression of estradiol to approximately 12 pg/mL was observed following treatment with elagolix 200 mg BID.

(b) Effect of Elagolix on QT Interval

Elagolix does not prolong the QTc interval. The effect of elagolix (up to 1200 mg) on QTc interval was evaluated in an active-controlled (moxifloxacin 400 mg) thorough QT study. At 17- to 23-fold (relative to 200 mg BID and 150 mg QD regimens, respectively) of elagolix therapeutic concentrations elagolix did not prolong the QTc interval.

(II) The pharmacokinetic properties of elagolix in healthy subjects are provided in Table A-1. The steady state pharmacokinetic parameters are presented in Table A-2.

TABLE A-1

| Pharmacokinetic Properties of Elagolix in Healthy Subjects | |
| --- | --- |
| Absorption | |
| $T_{max}$ (h) | 1.0 |
| Effect of high-fat meal (relative to fasting) | ↓24% |
| Distribution | |
| % Bound to human plasma proteins | 80 |
| Blood-to-plasma ratio | 0.6 |
| Metabolism | |
| Metabolism | CYP3A (major) Minor pathways include: CYP2D6, CYP2C8, and uridine glucuronosyltransferases (UGTs) |
| Elimination | |
| Major route of elimination | Hepatic metabolism |
| Terminal phase elimination half-life ($t_{1/2}$) (h) | 4-6 |
| % of dose excreted in urine | <3 |
| % of dose excreted in feces | 90 |

TABLE A-2

Mean (% CV) Steady State Pharmacokinetic Parameters of Elagolix

| Pharmacokinetic Parameter (Units) | 150 mg QD | 200 mg BID |
|---|---|---|
| $C_{max}$ (ng/mL) | 574 (29) | 774 (68) |
| $AUC_\tau$ (ng · hr/mL) | 1292 (31) | 1725 (57) |

CV: Coefficient of variation
$C_{max}$: peak concentration
$AUC_\tau$: area under the plasma concentration-time curve during the dosing interval (τ) i.e., 12 hours for BID, 24 hours for QD.

(III) Pharmacokinetics in Specific Populations (a) Renal Impairment

Elagolix exposures (Cmax and AUC) are not altered by renal impairment. The mean exposures are similar for women with moderate to severe or end stage renal disease (including women on dialysis) compared to women with normal renal function.

(b) Hepatic Impairment

Elagolix exposures (Cmax and AUC) are similar between women with normal hepatic function and women with mild hepatic impairment. Elagolix exposures in women with moderate and severe hepatic impairment are approximately 3-fold and 7-fold, respectively, of exposures from women with normal hepatic function.

(IV) Drug Interaction Studies

Drug interaction studies were performed with elagolix and other drugs that are likely to be co-administered and with drugs commonly used as probes for pharmacokinetic interactions. Tables A-3 and A-4 summarize the pharmacokinetic effects when elagolix was co-administered with other drugs which showed potentially clinically relevant changes.

TABLE A-3

Drug Interactions: Change in Pharmacokinetic Parameters of Elagolix in the Presence of Co-administered Drug

| Co-administered Drug | Regimen of Co-administered Drug | Regimen of Elagolix | N | Ratio (90% CI)* $C_{max}$ | Ratio (90% CI)* AUC |
|---|---|---|---|---|---|
| Ketoconazole | 400 mg once daily | 150 mg single dose | 11 | 1.77 (1.48-2.12) | 2.20 (1.98-2.44) |
| Rifampin | 600 mg single dose | 150 mg single dose | 12 | 4.37 (3.62-5.28) | 5.58 (4.88-6.37) |
| | 600 mg once daily | | | 2.00 (1.66-2.41) | 1.65 (1.45-1.89) |

CI: Confidence interval
*ratios for $C_{max}$ and AUC compare co-administration of the medication with elagolix vs. administration of elagolix alone.

TABLE A-4

Drug Interactions: Change in Pharmacokinetic Parameters of Co-administered Drug in the Presence of Elagolix

| Co-administered Drug | Regimen of Co-administered Drug | Regimen of Elagolix | N | Ratio (90% CI)* $C_{max}$ | Ratio (90% CI)* AUC |
|---|---|---|---|---|---|
| Digoxin | 0.5 mg single dose | 200 mg twice daily × 10 days | 11 | 1.71 (1.53-1.91) | 1.26 (1.17-1.35) |
| Rosuvastatin | 20 mg once daily | 300 mg twice daily × 7 days | 10 | 0.99 (0.73-1.35) | 0.60 (0.50-0.71) |
| Midazolam | 2 mg single dose | 300 mg twice daily × 11 days | 20 | 0.56 (0.51-0.62) | 0.46 (0.41-0.50) |
| | | 150 mg once daily × 13 days | 11 | 0.81 (0.74-0.89) | 0.65 (0.58-0.72) |
| Norethindrone | 0.35 mg once daily × 112 days | 150 mg once daily × 56 days | 32 | 0.95 (0.86-1.05) | 0.88 (0.79-0.99) |
| Ethinyl Estradiol Norelgestromin[a] Norgestrel[a] | Ethinyl estradiol 35 mcg and triphasic norgestimate 0.18/0.215/0.25 mg once daily | 150 mg once daily | 21 | 1.15 (1.07-1.25) 0.87 (0.78-0.97) 0.89 (0.78-1.00) | 1.30 (1.19-1.42) 0.85 (0.78-0.92) 0.92 (0.84-1.01) |

CI: Confidence interval
*ratios for $C_{max}$ and AUC compare co-administration of the medication with elagolix vs. administration of the medication alone.
[a]metabolite of norgestimate (V) Drug Interactions (a) Potential for Elagolix to Affect Other Drugs Elagolix is a weak to moderate inducer of cytochrome P450 (CYP) 3A enzyme. Co-administration with elagolix may decrease plasma concentration of drugs that are substrates of CYP3A.

Elagolix is an inhibitor of efflux transporter P-glycoprotein (P-gp) at 200 mg BID or higher, such as 300 mg BID or 400 mg QD or 600 mg QD. Co-administration with ELAGOLIX 200 mg BID may increase plasma concentration of drugs that are substrates of P-gp.

(b) Potential for Other Drugs to Affect Elagolix

Elagolix is a substrate of CYP3A, P-gp, and organic anion transporting polypeptide (OATP)1B1. Clinically meaningful interactions are not expected when elagolix is co-administered with drugs that inhibit CYP3A or P-gp.

Co-administration of elagolix with drugs that induce CYP3A may decrease elagolix plasma concentrations.

Co-administration of elagolix with drugs that inhibit OATP1B1 may increase elagolix plasma concentrations. Use of potent OATP1B1 inhibitors are not recommended with elagolix 200 mg BID regimen.

(c) Established and Other Potential Drug Interactions

Table A-5 provides the effect of co-administration of elagolix on concentrations of concomitant drugs and the effect of concomitant drugs on elagolix.

TABLE A-5

Established Drug Interactions Based on Drug Interaction Trials

| | | |
|---|---|---|
| Antiarrhythmics digoxin | ↑ digoxin | Clinical monitoring is recommended for digoxin when co-administered with ORILISSA. |
| Antimycobacterial rifampin | ↑ elagolix | Concomitant use of ORILISSA 200 mg twice daily and rifampin is not recommended. Limit concomitant use of ORILISSA 150 mg once daily and rifampin to 6 months. |
| Benzodiazepines oral midazolam | ↓ midazolam | Consider increasing the dose of midazolam and individualize therapy based on the patient's response. |
| Statins rosuvastatin | ↓ rosuvastatin | Consider increasing the dose of rosuvastatin. |

See Clinical Pharmacology, Tables A-3 and A-4.

The direction of the arrow indicates the direction of the change in AUC (↑=increase, ↓=decrease).

(d) Drugs with No Observed Clinically Significant Interactions with Elagolix

No dose adjustment is required when elagolix is co-administered with the following medications: ketoconazole, fluconazole, sertraline, and norethindrone or other progestin-only contraceptives.

(VI) Nonclinical Toxicology (a) Carcinogenesis

The 2-year carcinogenicity studies (conducted in mice and rats) revealed no increase in tumors in mouse at any dose, but an increase in thyroid (male and female) and liver (males only) tumors occurred in rat at the high dose (13-fold margin of safety with respect to 200 mg BID in women). The rat tumors were identified as being species-specific and of negligible relevance to humans. This conclusion is based on a follow-on thyroid and hepatic effects-related investigative study performed to document the possibility that thyroid and liver tumors may be specific to rat and occurred via induction of hepatic drug metabolizing enzymes at the high dose.

(b) Mutagenesis

Mutagenicity studies have been performed with elagolix using in vitro and in vivo test systems. These studies provided no evidence of a mutagenic or clastogenic potential.

(c) Impairment of Fertility

Effects on fertility and reproductive organs were evaluated in studies with rats and monkeys that achieved plasma concentrations less than the AUC at MRHD for rats and approximately 0.28-fold to 9.9-fold in monkeys, when adjusted for species difference in GnRH receptor binding affinity. In rats there was no effect in a fertility study (doses 50, 150, 300 mg/kg/day) but involution and a decrease in corpora lutea in ovaries were observed in a repeat-dose study (doses 600, 800 mg/kg/day). In a monkeys repeat-dose study (75, 150, 300 and 600 mg/kg/day), a reversible atrophy of reproductive organs (cervix, uterus and vagina) was observed at all doses. Based on pharmacologic actions of elagolix in humans a reversible effect on fertility may be expected in women.

(VII) Clinical Studies

The efficacy of elagolix 150 mg QD and 200 mg BID in the management of endometriosis with associated pain was demonstrated in two international double-blind, placebo-controlled studies in 1686 premenopausal women (Study EM-I and EM-II), and two uncontrolled, blinded extension studies (Study EM-III and EM-IV). Each placebo-controlled study assessed the reduction in endometriosis-associated pain over 6 months of treatment. More than 75 percent of women who completed Study EM-I and EM-II enrolled in the extension studies for an additional 6 month treatment period. Subjects were followed for up to 12 months post-treatment. See FIGS. 3-7.

(a) Reduction in Pain

The co-primary efficacy endpoints were the proportion of responders for dysmenorrhea and pelvic pain not related to menses (also known as non-menstrual pelvic pain [NMPP]) at Month 3 compared to placebo. The primary analysis independently evaluated these endpoints using a daily diary that asked patients to assess their pain and its impact on their daily activities, over the previous 24 hours. The Daily Endometriosis Pain Impact Scale, consisted of patient reported pain levels of None, Mild, Moderate or Severe (correlating with score of 0 to 3, respectively) and included a functional component for each score.

Women were defined as responders if they experienced clinically meaningful reduction in dysmenorrhea and/or NMPP with no increased analgesic use for endometriosis associated pain.

A higher proportion of women treated with elagolix 150 mg QD or 200 mg BID were responders for dysmenorrhea and NMPP versus placebo in a dose-dependent manner at Month 3. The persistence of efficacy was observed through Month 6 [see Table A-6].

Dyspareunia was evaluated as a secondary endpoint using the Daily Endometriosis Pain Impact Scale.

A higher proportion of women treated with elagolix 200 mg BID reported clinically meaningful reduction in dyspareunia versus placebo at Month 3 through Month 6.

TABLE A-6

Proportion and Number of Responders† for Dysmenorrhea, Non-Menstrual Pelvic Pain and Dyspareunia at Month 3 and Month 6 in Studies EM-I and EM-II, using the Daily Endometriosis Pain Impact Scale

|  | Study EM-I | | | Study EM-II | | |
|---|---|---|---|---|---|---|
|  | Elagolix | | | Elagolix | | |
|  | 150 mg QD %/(n/N) | 200 mg BID %/(n/N) | Placebo %/(n/N) | 150 mg QD %/(n/N) | 200 mg BID % (n/N) | Placebo % (n/N) |
| Dysmenorrhea (Month 3) | 46.4*** (115/248) | 75.8*** (185/244) | 19.6 (73/373) | 43.4%*** (96/221) | 72.4*** (163/225) | 22.7 (80/353) |
| Dysmenorrhea (Month 6)α | 42.1*** (104/247) | 75.3*** (183/243) | 23.1 (86/372) | 46.2%*** (102/221) | 76.9*** (173/225) | 25.4 (90/355) |
| Non-Menstrual Pelvic Pain (Month 3) | 50.4*** (125/248) | 54.5*** (133/244) | 36.5 (136/373) | 49.8** (110/221) | 57.8*** (130/225) | 36.5 (129/353) |
| Non-Menstrual Pelvic Pain (Month 6)α | 45.7** (113/247) | 62.1*** (151/243) | 34.9 (130/372) | 51.6** (114/221) | 62.2*** (140/225) | 40.6 (144/355) |
| Dyspareuniaα (Month 3) | 39.6 (74/187) | 47.1*** (81/172) | 31.9 (90/282) | 44.0 (70/159) | 53.7** (87/162) | 39.5 (101/256) |
| Dyspareuniaα (Month 6) | 39.6 (74/187) | 50.3*** (81/161) | 33.3 (90/270) | 39.9 (65/163) | 55.8*** (92/165) | 39.4 (100/254) |

†A responder had a reduction in pain from baseline to the analysis month greater than or equal to a calculated, clinically important threshold of improvement, and also had stable or decreased rescue analgesic use.
αA secondary endpoint
*, , *P ≤ 0.001, 0.01, and 0.05, respectively, for test of difference from placebo Both elagolix treatment groups showed mean decreases from Baseline in dysmenorrhea scores that were statistically significantly greater than placebo beginning at Month 1 and persisted through Month 6.

Women in these studies also provided a daily self-assessment of their endometriosis pain using the Numeric Rating Scale (NRS), on a scale ranging from 0 (no pain) to 10 (worst pain ever). Women taking elagolix 150 mg QD and 200 mg BID reported a highly statistically (p<0.001) significant reduction in NRS scores compared to placebo at Month 3 and Month 6.

In the two blinded extension studies EM-III and EM-IV, where the patients who were originally on elagolix in the controlled studies EM-I and EM-II were maintained on their dose, the durability of improvement in dysmenorrhea, NMPP and dyspareunia was demonstrated for a total of 12 months. In study EM-IV, efficacy was maintained when elagolix was taken with and without food.

Results on efficacy endpoints from Study EM-II were consistent with those observed in Study EM-I.

(b) Reduction in Pain Medication Use

In these studies, women taking elagolix 200 mg BID reduced the amount of opioid (hydrocodone with acetaminophen) or naproxen rescue medication used to treat their endometriosis-associated pain compared to the amount required at baseline. In addition, there was a significant reduction in the percentage of days per month of the opioid or naproxen rescue medication use for women taking elagolix 200 mg BID compared to women taking placebo. These effects were less consistently observed for women taking elagolix 150 mg QD. See FIG. 7. Compared with placebo, the 200 mg BID elagolix group had a significant decrease from baseline in the percent change of averaged daily opioid pills at Months 3 through 6. Reduction in pain may be reflected by reduction in pain medication, such as prescription opioids or non-steroidal anti-inflammatory agents (NSAIDs) that may be prescribed or found over the counter, for example, naproxen or acetaminophen. 150 mg once a day or twice a day is also expected to reduce intake of pain medication and show reduction in pain, similarly 300 mg doses whether taken once a day or twice a day, is also expected to reduce intake of pain medication and show reduction in pain. In this pooled analysis of rescue analgesic use in two phase 3 trials, compared with placebo: (1) both doses of elagolix 150 QD and 200 BID, showed a significant reduction in the percentage of days in which rescue opioid medication was taken; (2) 200 mg BID elagolix dose showed a significant reduction in the mean percent daily pill counts; (3) fewer women in each elagolix group had increases in the opioid dose and more women had a decreased or stable opioid dose.

In EM-1 and EM-2, 59% and 60% of patients used an opioid rescue analgesic for pain at baseline. The opioid rescue analgesics used at baseline were predominantly hydrocodone/acetaminophen (HC/APAP) and codeine/APAP at strengths of 5/300-325 mg and 30/300-500 mg. In EM-1, of all patients on an opioid at baseline, 98% and 2% were on HC/APAP and codeine/APAP, respectively. In EM-2, of all patients on an opioid at baseline, 50% were on HC/APAP, 16% were on codeine/APAP, 3% were on codeine, and 32% were on tramadol/APAP.

(c) Effects on Bleeding Patterns

Effects on Menstrual Bleeding Patterns

The effects of elagolix on menstrual bleeding were evaluated for up to 12 months using an electronic daily diary where subjects classified their flow of menstrual bleeding (if present in the last 24 hours) as spotting, light, medium, or heavy. Elagolix led to a dose-dependent reduction in mean number of bleeding and spotting days and bleeding intensity in those subjects who reported menstrual bleeding.

TABLE B-3

Mean Bleeding/Spotting Days and Mean Intensity Scores at Month 3

|  | Elagolix 150 mg Once Daily | | Elagolix 200 mg Twice Daily | | Placebo | |
|---|---|---|---|---|---|---|
|  | Baseline | Month 3 | Baseline | Month 3 | Baseline | Month 3 |
| Mean bleeding/spotting days in prior 28 days | 5.3 | 2.8 | 5.7 | 0.8 | 5.4 | 4.6 |
| Mean Intensity score[a] | 2.6 | 2.2 | 2.5 | 2.0 | 2.6 | 2.4 |

[a]Intensity for subjects who reported at least 1 day of bleeding or spotting during 28 day interval. Scale ranges from 1 to 4, 1 = spotting, 2 = light, 3 = medium, 4 = heavy Elagolix also demonstrated a dose-dependent increase in the percentage of women with amenorrhea (defined as no bleeding or spotting in a 56-day interval) over the treatment period. The incidence of amenorrhea during the first six months of treatment ranged from 6-17% for elagolix 150 mg once daily, 13-52% for elagolix 200 mg twice daily and less than 1% for placebo. During the second 6 months of treatment, the incidence of amenorrhea ranged from 11-15% for elagolix 150 mg once daily and 46-57% for elagolix 200 mg twice daily.

After 6 months of therapy with elagolix 150 mg once daily, resumption of menses after stopping was reported by 59%, 87%, and 95% of women within 1, 2, and 6 months respectively. After 6 months of therapy with elagolix 200 mg twice daily, resumption of menses after stopping treatment was reported by 60%, 88%, and 97% of women within 1, 2, and 6 months, respectively.

After 12 months of therapy with elagolix 150 mg once daily resumption of menses after stopping treatment was reported by 77%, 95% and 98% of women within 1, 2, and 6 months respectively. After 12 months of therapy with elagolix 200 mg twice daily resumption of menses after stopping treatment was reported by 55%, 91% and 96% of women within 1, 2, and 6 months respectively.

(VII) Lactation

Risk Summary: No human studies have been conducted to assess the impact of elagolix on milk production, its presence in breast milk, or its effects on the breastfed child. It is not known whether elagolix and its metabolites are present in human breast milk, affect human milk production or have effects on the breastfed infant.

(a) In Rats Elagolix is Secreted Minimally Via Milk.

The developmental and health benefits of breastfeeding should be considered along with the mother's clinical need for elagolix and any potential adverse effects on the breastfed child from elagolix.

(b) Data: Animal Data

Pregnant rats were given diet containing elagolix throughout the gestation and lactation periods to achieve a daily elagolix dose of 400 mg/kg. During nursing the dams and litters were divided into restricted feeding and non-restricted groups to determine whether elagolix was secreted in the mother's milk. At post natal day 10 and 20 elagolix plasma concentrations in pups of the restricted feeding litters were not measurable. In pups of the non-restricted feeding group, elagolix plasma concentrations were measurable and approximately 1% of the mother's plasma concentrations. Using plasma concentrations in pups as a surrogate of exposure via lactation elagolix is considered to be minimally secreted in milk.

(IX) Adverse Reactions (a) Clinical Trials Experience

Because clinical trials are conducted under widely varying conditions, adverse reaction rates observed in the clinical trials of a drug cannot be directly compared to rates in the clinical trials of another drug and may not reflect the rates observed in clinical practice.

The safety of elagolix was evaluated in two six-month placebo-controlled clinical studies (Study EM-I and Study EM-II) in which a total of 952 women were treated with 150 mg QD or with 200 mg BID. The population age range was 18-49 years old. Women who completed six months of treatment and met eligibility criteria continued treatment in two blinded six-month extension studies, for a total treatment duration of up to 12 months.

(b) Adverse Reactions (>1%) Leading to Study Discontinuation

In the two controlled studies (EM-I and EM-II), 5.5% of patients treated with elagolix 150 mg QD and 9.6% of patients treated with elagolix 200 mg BID discontinued therapy due to adverse reactions. Discontinuations for both dosage forms were most commonly due to hot flush (0.8% and 2.5%) and nausea (0.8% and 1.5%). The majority of discontinuation due to hot flushes and nausea occurred within the first 2 months of therapy. No woman discontinued elagolix 150 mg QD for hot flushes during the extension study after receiving it for 6 months in the controlled study.

(c) Common Adverse Reactions:

Adverse reactions reported in ≥5% of women in the two placebo-controlled studies in either elagolix dose group and at a greater frequency than placebo are noted in the following table A-7.

TABLE A-7

Percentage of Patients in Studies EM-I and EM-II with Treatment-Emergent Adverse Reactions Occurring in at Least 5% of Patients (either elagolix Dose Group) and Greater than Placebo

|  | Elagolix 150 mg QD N = 475 % | Elagolix 200 mg BID N = 477 % | Placebo N = 734 % |
|---|---|---|---|
| Gastrointestinal Disorders | | | |
| Nausea | 11 | 16 | 13 |
| Infections and Infestations | | | |
| Nasopharyngitis | 6 | 6 | 4 |
| Sinusitis | 5 | 6 | 4 |
| Upper Respiratory Tract Infection | 6 | 4 | 5 |

TABLE A-7-continued

Percentage of Patients in Studies EM-I and EM-II with Treatment-Emergent Adverse Reactions Occurring in at Least 5% of Patients (either elagolix Dose Group) and Greater than Placebo

| | Elagolix 150 mg QD N = 475 % | Elagolix 200 mg BID N = 477 % | Placebo N = 734 % |
|---|---|---|---|
| Musculoskeletal and Connective Tissue Disorder | | | |
| Arthralgia | 3 | 5 | 3 |
| Nervous System Disorders | | | |
| Headache | 17 | 20 | 12 |
| Psychiatric Disorders | | | |
| Anxiety | 3 | 5 | 3 |
| Insomnia | 6 | 9 | 3 |
| Reproductive System and Breast Disorders | | | |
| Amenorrhoea* | 4 | 7 | <1 |
| Vascular Disorders | | | |
| Hot Flush | 23 | 45 | 9 |

*[See Clinical Studies - Effects on Bleeding Patterns (VII)]

In the extension studies, the adverse reaction profile was similar to that noted in Placebo-controlled studies, as noted in Table A-7.

(d) Less Common Adverse Reactions:

In EM-I and EM-II, adverse reactions reported in ≥3% and <5% in either elagolix dose group and greater than placebo included:
 a) Investigations: weight increased;
 b) Psychiatric Disorders: depression, irritability, libido decreased, mood swings;
 c) Gastrointestinal Disorders: diarrhea, abdominal pain, constipation;
 d) Nervous System Disorders: dizziness; or
 e) Skin and Subcutaneous Tissue Disorders: night sweats.

Events of hot flushes were dose-dependent and the majority were assessed as mild to moderate. All other adverse events were comparable between both doses of elagolix. The addition of low dose hormone add-back therapy may reduce the occurrence of symptoms associated with estrogen reductions such as hot flush.

(e) Changes in Bone Mineral Density

In the placebo-controlled and extension clinical studies, BMD was measured by DXA. The BMD data of the lumbar spine from these studies are presented in Table A-8. Changes observed in BMD at other anatomical sites (femoral neck, total hip) were generally smaller than lumbar spine.

Following 12 months of elagolix treatment, no patient on the 150 mg daily dose and less than 1% of patients on the 200 mg BID dose had a Z-score below the normal lower bound of −2.0. In both ELAGOLIX treatment groups, there was progressive recovery of BMD at three DXA sites: lumbar spine, total hip and femoral neck at post-treatment months 6 and 12.

Additional analysis from exposure-response modeling shows that for elagolix 150 mg QD, the predicted mean (95% CI) Z-score is 0.23 (0.01-0.45) and 0.18 (−0.04-0.40) at Months 12 and 24, respectively. The model predicts that in subjects who initiate treatment on elagolix 150 mg QD for 3 months then increase the dose to 200 mg BID, the predicted mean (95% CI) Z-score is 0.23 (−0.01-0.47) and 0.11 (−0.13-0.36) at Months 6 and 12, respectively.

(f) Changes in Laboratory Values During Treatment (i) Lipids

While dose-dependent increases in total cholesterol, low-density lipoprotein cholesterol (LDL-C), high density lipoprotein cholesterol (HDL-C), and triglycerides were noted during elagolix treatment, these values remained generally within the normal range.

Lipid increases typically occurred within 1 to 2 months after the start of elagolix therapy and remained stable thereafter over 12 months. Elevated levels of lipids returned to baseline one month after stopping treatment.

The mean increase from pretreatment baseline in LDL-C was 5.25 mg/dL for 150 mg QD and 13.10 mg/dL for 200 mg BID. The mean increase from pretreatment baseline in HDL-C was 2.24 mg/dL for 150 mg QD and 4.16 mg/dL for 200 mg BID. The mean increase from pretreatment baseline in triglycerides was 0.42 mg/dL for 150 mg QD and 11.08 mg/dL for 200 mg BID following 6-month treatment of elagolix.

Changes in lipid ratios were minimal due to increases in both LDL-C and HDL-C.

Lipid profiles should be assessed and managed according to current clinical practice guidelines.

(ii) Endometrial Safety

Endometrial biopsies were performed in subjects in Study EM-I and its extension at Month 6 and Month 12. The results indicate a dose-dependent decrease in proliferative and secretory biopsy patterns and an increase in quiescent/minimally stimulated biopsy patterns. There were no abnormal biopsy findings post-baseline, such as endometrial hyperplasia or cancer.

Based on transvaginal ultrasound, during the course of a 3-menstrual cycle study in healthy women, elagolix 150 mg

TABLE A-8

Mean Percentage Change From Baseline in Bone Mineral Density and Percent of Subjects with Z-score ≤ −1.5 of Lumbar Spine

| | Elagolix 150 mg QD | | | Elagolix 200 mg BID | | |
|---|---|---|---|---|---|---|
| | N | Mean Percent Change (95% CI) | % Subjects Z-score ≤ −1.5 On Treatment | N | Mean Percent Change (95% CI) | % Subjects Z-score ≤ −1.5 |
| Month 6 | 360 | −0.52 (−0.79, −0.26) | 0.8% | 365 | −2.54 (−2.81, −2.28) | 4.1% |
| Month 12 | 235 | −0.87 (−1.29, −0.45) | 1.3% | 217 | −3.76 (−4.19, −3.32) | 5.1% |

QD and 200 mg BID resulted in a dose dependent decrease in the mean endometrial thickness compared to the pretreatment values.

(X) Decrease in Bone Mineral Density

Elagolix reduces serum estradiol levels in a dose-dependent manner that may also be associated with a dose-dependent decrease in bone mineral density (BMD). There is progressive recovery of BMD at 6 and 12 months after stopping treatment [see Adverse Reactions (6.1)].

Assess BMD by dual-energy x-ray absorptiometry (DXA) after 12 months of continuous use. Discontinue elagolix if BMD Z-score is lower than −2.0 until BMD is in the age-appropriate range.

If use of elagolix continues for longer than 12 months, it is recommended that BMD be assessed as clinically indicated. The loss of BMD in premenopausal women should be considered in the benefit/risk assessment for women receiving elagolix for continuous long-term use.

Consider assessment of BMD sooner than annually in patients at greater risk of low BMD. Risk factors include: taking elagolix 200 mg twice daily, a Z-score of less than −2.0 after a previous course of treatment with elagolix, prior use of GnRH agonists, metabolic bone disease, chronic alcohol and/or tobacco use, anorexia nervosa, strong family history of osteoporosis, or chronic use of drugs that can reduce bone mass such as anticonvulsants or corticosteroids.

Although there are no studies addressing whether calcium and vitamin D may lessen BMD loss in women using elagolix, all patients should have adequate calcium and vitamin D intake.

Clinical studies with GnRH analogs or elagolix (in other populations) suggest the use of low dose hormonal add-back therapy (estrogens/progestins or norethindrone acetate) may be effective in reducing the bone mineral loss which occurs with these agents alone.

(XI) Dosage and Administration
(a) Dosing Information

Elagolix will be available as either 150 mg tablets (once daily, QD) or 200 mg tablets (twice daily, BID), 150 mg BID, 300 mg BID or 400 mg QD or 600 mg QD to be taken orally with or without food.

(b) Dosing Recommendation

Based on the severity of symptoms and treatment objectives, use the lowest effective dose [see Clinical Studies (VII)]. Treatment with elagolix may be initiated at any time during a patient's menstrual cycle.

TABLE B-1

In one embodiment, the recommended Dosage and Duration of Use

| Dosing Regimen | Maximum Treatment Duration | Coexisting Condition |
| --- | --- | --- |
| Initiate treatment with ORILISSA 150 mg once daily | 24 months | None |
| Consider initiating treatment with ORILISSA 200 mg twice daily | 6 months | Dyspareunia |
| Initiate treatment with ORILISSA 150 mg once daily. Use of 200 mg twice daily is not recommended. | 6 months | Moderate hepatic impairment (Child-Pugh Class B) |

No dosage adjustment of elagolix is required in women with mild hepatic impairment (Child-Pugh A).

Compared to women with normal liver function, those with moderate hepatic impairment had approximately 3-fold higher elagolix exposures and those with severe hepatic impairment had approximately 7-fold higher elagolix exposures. Because of these increased exposures and risk for bone loss: elagolix 150 mg once daily is recommended for women with moderate hepatic impairment (Child-Pugh B) with the duration of treatment limited to 6 months. Use of elagolix 200 mg twice daily is not recommended for women with moderate hepatic impairment. Elagolix is contraindicated in women with severe hepatic impairment (Child-Pugh C).

Each tablet contains 155.2 mg of elagolix sodium equivalent to 150 mg of elagolix. Each tablet contains 207.0 mg of elagolix sodium equivalent to 200 mg of elagolix.

(c) Renal Impairment

No dose adjustment of elagolix is required in women with any degree of renal impairment or end-stage renal disease (including women on dialysis) [see Use in Specific Populations and Clinical Pharmacology].

(d) Hepatic Impairment

No dosage adjustment of elagolix is required in women with mild hepatic impairment (Child-Pugh A). Elagolix 150 mg QD regimen is recommended in women with moderate hepatic impairment (Child-Pugh B); the 200 mg BID regimen is not recommended.

Elagolix is contraindicated in women with severe hepatic impairment (Child-Pugh C).

Hepatic Transaminase Elevations

In clinical trials, dose-dependent elevations of serum alanine aminotransferase (ALT) at least 3-times the upper limit of the reference range occurred with elagolix. Use the lowest effective dose of elagolix and is recommended. Further, patients are instructed to promptly seek medical attention in case of symptoms or signs that may reflect liver injury, such as jaundice. Patients are promptly evaluated for elevations in liver tests to determine whether the benefits of continued therapy outweigh the risks.

In the placebo-controlled clinical trials (Studies EM-1 and EM-2), dose-dependent asymptomatic elevations of serum ALT to at least 3-times the upper limit of the reference range occurred during treatment with ORILISSA (150 mg once daily—1/450, 0.2%; 200 mg twice daily—5/443, 1.1%; placebo—1/696, 0.1%). Similar increases were seen in the extension trials (Studies EM-3 and EM-4).

(e) Suicidal Ideation, Suicidal Behavior, and Exacerbation of Mood Disorders

Subjects using elagolix had a higher incidence of depression and mood changes compared to placebo, and elagolix users subjects with a history of suicidality or depression had a higher incidence of depression compared to users subjects without such a history. Patients with depressive symptoms should be evaluated to determine whether the risks of continued therapy outweigh the benefits. Patients with new or worsening depression, anxiety or other mood changes should be referred to a mental health professional, as appropriate. Patients with suicidal ideation and behavior should seek immediate medical attention. Benefits and risks of continuing elagolix should be revaluated if such events occur and optionally, elagolix should be stopped with worsening or serious depression, anxiety, mood changes or suicidal ideation.

In the placebo-controlled trials (Studies EM-1 and EM-2), elagolix was associated with adverse mood changes, particularly in those with a history of depression.

TABLE B-2

Suicidal Ideation, Suicidal Behavior and
Mood Disorders in Studies EM-1 and EM-2

| Adverse Reactions | Elagolix 150 mg Once Daily (N = 475) N (%) | Elagolix 200 mg Twice Daily (N = 477) N (%) | Placebo (N = 734) N (%) |
|---|---|---|---|
| Completed Suicide | 1 (0.2) | 0 | 0 |
| Suicidal ideation | 1 (0.2) | 1 (0.2) | 0 |
| Depressed Mood, depression, depressive symptoms and or tearfulness | 13 (2.7) | 29 (6.1) | 17 (2.3) |
| Mood altered, mood swings | 25 (5.7) | 25 (5.2) | 25 (3.4) |

NOTE:
The same subject may be included in more than one row if she reported more than one adverse reaction (e.g., suicidal ideation and depression).

Example A-4. Elagolix Reduces Fatigue in Patients with Moderate to Severe Endometriosis Pain A Phase III study was conducted to assess the effects of elagolix for clinically meaningful reductions in pain and other symptoms. Data provided examined the impact of elagolix on fatigue in women with moderate to severe endometriosis-related pain. In the study of three cohorts, first cohort comprised women who received placebo, second cohort comprised women who received 150 mg of elagolix once daily and third cohort comprised women who received 200 mg of elagolix twice daily. It is expected that 300 mg once daily or twice daily and 600 mg once daily, or similar doses will similarly show reduction in fatigue. Fatigue was assessed using the Patient Reported Outcome Measurement Information System (PROMIS®), Fatigue Short Form (SF) 6a. Six items assessed a range of self-reported symptoms from mild, subjective feelings of tiredness to overwhelming, sustained sense of exhaustion that likely decreases one's ability to execute daily activities and function normally. The domain was divided into the experience of fatigue (frequency, duration and intensity) and impact of fatigue on physical, mental and social activities. All items assessed fatigue over the previous seven days. Responses to each question was filed on a 5-item Likert scale: 1—"Not at all"; 2—"A little bit"; 3—"Somewhat"; 4—"Quite a bit"; and 5—"Very much." The questionnaire was administered at baseline and months 1, 3, and 6. Lower scores indicated less fatigue. Post-hoc, Fatigue SF-6a raw scores were converted to T-scores. The T-score rescales 5 the raw score into a standardized score such that the general population has a mean of 50 and a standard deviation (SD) of 10.

Analysis: Changes from baseline in PROMIS Fatigue SF-6a T-scores were compared between each active treatment (elagolix 150 mg QD and 200 mg BID) and placebo. 1-way Analysis of Covariance (ANCOVA) was utilized. ANCOVA controlled for treatment as main effect. Baseline Fatigue SF-6a T-score included as a covariate.

Figure 8:
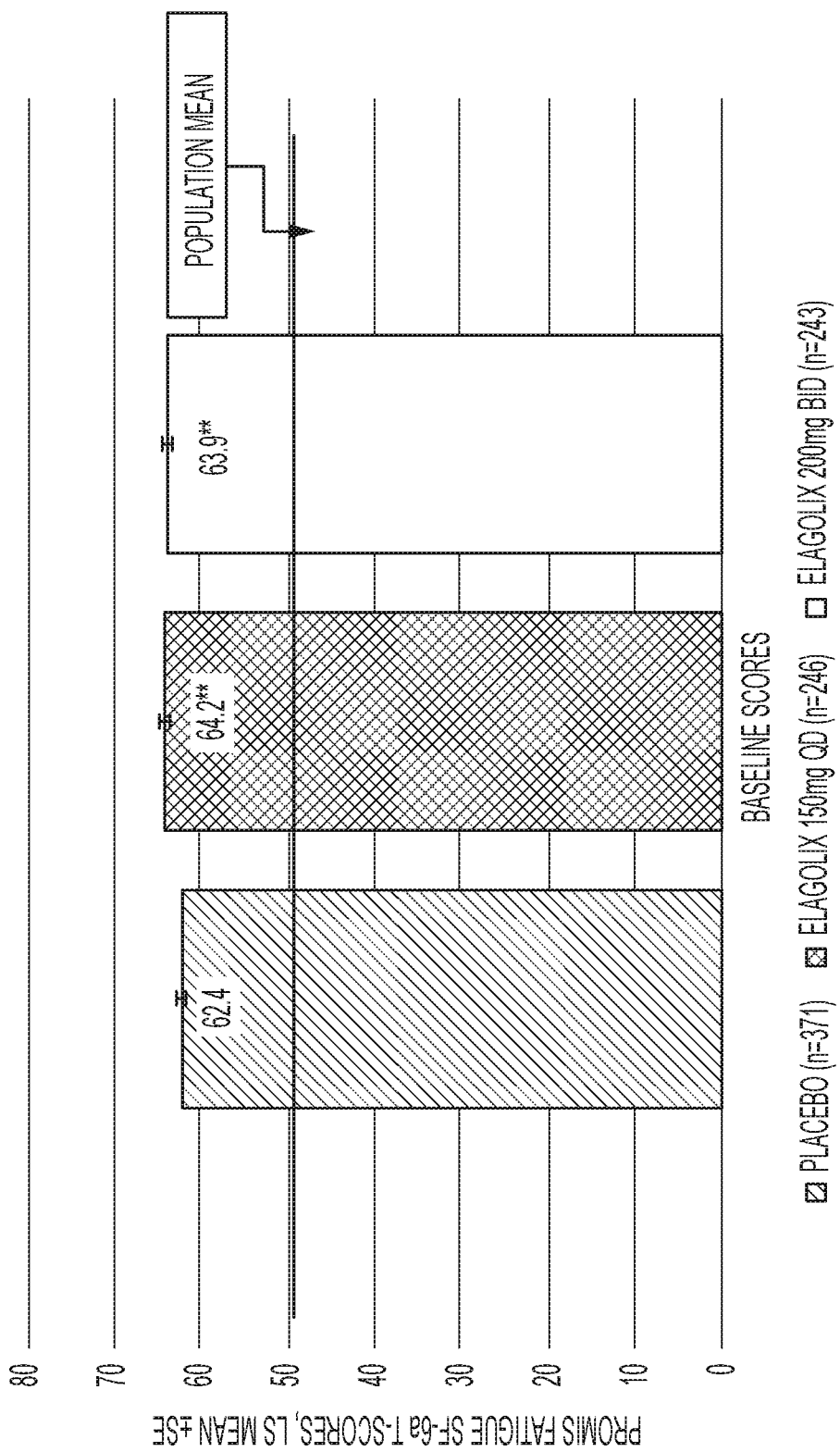
FIG. 8: Depicts that the baseline Promis Fatigue SF-6a T-Scores, on average, were more than 1 SD above the population norm [mean=50; SD=10].  denotes $P<0.01$;  shows statistical significance for elagolix arms versus placebo from ANOVA model for fatigue, including treatment as the main factor. The Maximum SF-6a T-Score=76.8.
Figure 9:
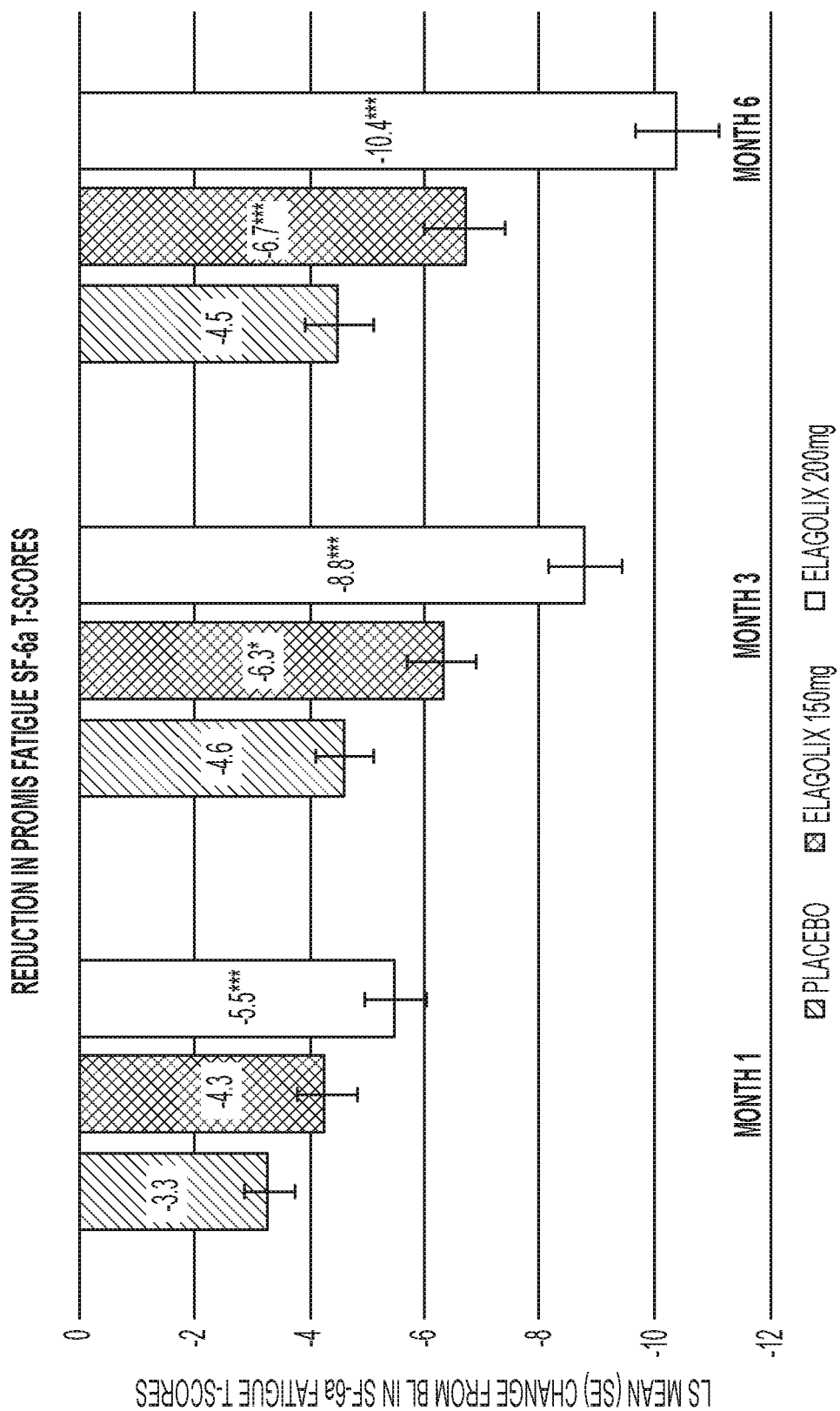
FIG. 9: Depicts that elagolix reduced Fatigue Score from baseline among Endometriosis Patients. Statistical significance versus placebo, $P<0.05$, $<0.01$, $<0.001$ (*,,*), from ANCOVA model for fatigue is shown, including treatment as the main factor and baseline fatigue as a covariate, which compared each treatment group to placebo.

Fatigue among women with endometriosis-related pain remains an unmet medical need. At baseline, women in this study had levels of fatigue that were 1SD worse on average than women in the general population. Compared to placebo, elagolix improved fatigue in a dose dependent manner in women with moderate to sever pain associated with endometriosis. See FIG. 8. Statistically significant reductions relative to placebo in the PROMIS Fatigue SF-6a T-Score observed with both doses of elagolix at Months 3 and 6. A statistically significant reduction in fatigue with elagolix 200 mg was also observed as early as Month 1. See FIG. 9. It is expected that all therapeutic doses of elagolix described above would reduced fatigue in women suffering from moderate to severe endometriosis.

Example 5: Gel Formation and pH of Elagolix Sodium Solution 1.23 gram of elagolix sodium was added to 2 mL purified water in a test tube. It was observed that elagolix sodium started to form gel during the dissolution process. To facilitate continued dissolution, the solution was stirred and the gel was dispersed continuously using a spatula. The solution pH was measured with undissolved solid present using a calibrated pH meter. The pH value of the solution was 9.80 at 20° C.

It is understood that the foregoing detailed description and accompanying examples are merely illustrative and are not to be taken as limitations upon the scope of the invention, which is defined solely by the appended claims and their equivalents. Various changes and modifications to the disclosed embodiments will be apparent to those skilled in the art. Such changes and modifications, including without limitation those relating to the chemical structures, substituents, derivatives, intermediates, syntheses, formulations, or methods, or any combination of such changes and modifications of use of the invention, may be made without departing from the spirit and scope thereof.

All references (patent and non-patent) cited above are incorporated by reference into this patent application. The discussion of those references is intended merely to summarize the assertions made by their authors. No admission is made that any reference (or a portion of any reference) is relevant prior art (or prior art at all). Applicant reserves the right to challenge the accuracy and pertinence of the cited references.

The invention claimed is:

1. A high drug load, stable tablet comprising sodium 4-((R)-2-[5-(2-fluoro-3-methoxy-phenyl)-3-(2-fluoro-6-trifluoromethyl-benzyl)-4-methyl-2,6-dioxo-3,6-dihydro-2H-pyrimidin-1-yl]-1-phenyl-ethylamino)butanoate ("elagolix sodium");
   wherein the high drug load, stable tablet comprises from about 50% to about 90% of elagolix sodium by weight of the tablet and from about 0.1% to about 20% of a pharmaceutically acceptable meltable binder by weight of the tablet, wherein about 310 mg elagolix sodium is present in the tablet and wherein the pharmaceutically acceptable meltable binder is selected from the group consisting of a polyethylene glycol (PEG), a cellulose derivative, a poloxamer, and combinations thereof; and
   wherein the high drug load, stable tablet controls degradation of elagolix sodium to within pharmaceutically acceptable levels for at least 1 month when said tablet is stored at 40° C./75% relative humidity.

2. The tablet of claim 1, wherein the elagolix sodium is present in an amount from about 55% to about 60% by weight of the tablet.

3. The tablet of claim 1, wherein the pharmaceutically acceptable meltable binder is present in an amount from about 2% to about 10% by weight of the tablet.

4. The tablet of claim 1, wherein the elagolix sodium is present in an amount from about 55% to about 60% by weight of the tablet and the pharmaceutically acceptable meltable binder is present in an amount from about 2% to about 10% by weight of the tablet.

5. The tablet of claim 1, wherein not more than about 0.5% of a lactam degradant is present in the tablet following storage for at least 1 month at 40° C./75% relative humidity.

6. The tablet of claim 1, wherein the pharmaceutically acceptable meltable binder is selected from the group consisting of polyethylene glycol 3350, hydroxypropylcellulose, poloxamer 188, and combinations thereof.

7. The tablet of claim 1, wherein the pharmaceutically acceptable meltable binder is polyethylene glycol 3350.

8. The tablet of claim 1, further comprising at least one pharmaceutically acceptable excipient selected from the group consisting of a disintegrant, a glidant, a pH modifying agent, and a combination thereof.

9. The tablet of claim 1, further comprising a disintegrant, wherein the disintegrant is selected from the group consisting of cross-linked modified starches, cross-linked polyvinylpyrrolidone, cross-linked carboxymethyl cellulose, and combinations thereof.

10. The tablet of claim 9, further comprising a disintegrant, wherein the disintegrant is present in an amount from about 2% to about 8% by weight of the tablet.

11. The tablet of claim 1, further comprising a glidant, wherein the glidant is colloidal silicon dioxide.

12. The tablet of claim 1, further comprising a glidant, wherein the glidant is present in an amount from about 0.5% to about 3% by weight of the tablet.

13. The tablet of claim 1, further comprising a pH modifying agent, wherein the pH modifying agent is present in an amount from about 25% to about 35% by weight of the tablet.

14. The tablet of claim 13, wherein the pH modifying agent is an alkali or alkaline earth metal hydroxide or an alkali or alkaline earth metal salt.

15. The tablet of claim 13, wherein the pH modifying agent is sodium carbonate.

16. The tablet of claim 1, wherein the tablet comprises a first solid phase and the first solid phase comprises elagolix sodium and the pharmaceutically acceptable meltable binder.

17. A high drug load, stable tablet comprising:
(a) from about 55% to about 60% by weight of sodium 4-((R)-2-[5-(2-fluoro-3-methoxy-phenyl)-3-(2-fluoro-6-trifluoromethyl-benzyl)-4-methyl-2,6-dioxo-3,6-dihydro-2H-pyrimidin-1-yl]-1-phenyl-ethylamino)butanoate ("elagolix sodium");
(b) from about 4% to about 6% by weight of a pharmaceutically acceptable meltable binder, wherein the pharmaceutically acceptable meltable binder is selected from the group consisting of polyethylene glycol 3350, hydroxypropylcellulose, poloxamer 188, and combinations thereof;
(c) from about 4% to about 6% by weight of a disintegrant;
(d) from about 0.1% to about 2% by weight of a glidant; and
(e) from about 25% to about 35% by weight of a pH modifying agent;
wherein said high drug load, stable tablet controls degradation of elagolix sodium to within pharmaceutically acceptable levels for at least 1 month when said tablet is stored at 40° C./75% relative humidity.

18. The tablet of claim 17, wherein about 310 mg elagolix sodium is present in the tablet.

19. The tablet of claim 17, wherein the pharmaceutically acceptable meltable binder is polyethylene glycol 3350.

20. A method of treating endometriosis, the method comprising administering the tablet of claim 1 to a patient in need thereof.

21. The method according to claim 20, wherein the tablet comprises:
(a) from about 55% to about 60% by weight of elagolix sodium;
(b) from about 4% to about 6% by weight of the pharmaceutically acceptable meltable binder;
(c) from about 4% to about 6% by weight of a disintegrant;
(d) from about 0.1% to about 2% by weight of a glidant; and
(e) from about 25% to about 35% by weight of a pH modifying agent.

22. A method of treating uterine fibroids, the method comprising administering the tablet of claim 1 to a patient in need thereof.

23. The method according to claim 22, wherein the tablet comprises:
(a) from about 55% to about 60% by weight of elagolix sodium;
(b) from about 4% to about 6% by weight of the pharmaceutically acceptable meltable binder;
(c) from about 4% to about 6% by weight of a disintegrant;
(d) from about 0.1% to about 2% by weight of a glidant; and
(e) from about 25% to about 35% by weight of a pH modifying agent.

24. A high drug load, stable tablet comprising sodium 4-((R)-2-[5-(2-fluoro-3-methoxy-phenyl)-3-(2-fluoro-6-trifluoromethyl-benzyl)-4-methyl-2,6-dioxo-3,6-dihydro-2H-pyrimidin-1-yl]-1-phenyl-ethylamino)butanoate ("elagolix sodium");
wherein the high drug load, stable tablet comprises from about 50% to about 90% of elagolix sodium by weight of the tablet and from about 0.1% to about 20% of a pharmaceutically acceptable meltable binder by weight of the tablet, wherein the pharmaceutically acceptable meltable binder is suitable for use in melt processing techniques for tablet preparation and wherein the tablet comprises a solid matrix, the solid matrix comprising a molecular dispersion of elagolix sodium and the pharmaceutically acceptable meltable binder; and
wherein the high drug load, stable tablet controls degradation of elagolix sodium to within pharmaceutically acceptable levels for at least 1 month when said tablet is stored at 40° C./75% relative humidity.

25. The tablet of claim 24, wherein the pharmaceutically acceptable meltable binder is a polyalkylene glycol.

26. The tablet of claim 24, wherein the pharmaceutically acceptable meltable binder has a melting point of less than 124° C.

27. The tablet of claim 24, wherein the pharmaceutically acceptable meltable binder is selected from the group consisting of a polyethylene glycol (PEG), a cellulose derivative, a poloxamer, and combinations thereof.

28. The tablet of claim 24, wherein the pharmaceutically acceptable meltable binder is a polyethylene glycol (PEG).

29. The tablet of claim 24, wherein the pharmaceutically acceptable meltable binder is polyethylene glycol 3350.

30. The tablet of claim 24, wherein the pharmaceutically acceptable meltable binder is a poloxamer.

31. The tablet of claim 24, wherein the pharmaceutically acceptable meltable binder is poloxamer 188.

32. The tablet of claim 24, further comprising a disintegrant, wherein the disintegrant is selected from the group consisting of cross-linked modified starches, cross-linked polyvinylpyrrolidone, cross-linked carboxymethyl cellulose, and combinations thereof.

33. The tablet of claim 24, further comprising a disintegrant, wherein the disintegrant is present in an amount from about 2% to about 8% by weight of the tablet.

34. A high drug load, stable tablet comprising sodium 4-((R)-2-[5-(2-fluoro-3-methoxy-phenyl)-3-(2-fluoro-6-trifluoromethyl-benzyl)-4-methyl-2,6-dioxo-3,6-dihydro-2H-pyrimidin-1-yl]-1-phenyl-ethylamino)butanoate ("elagolix sodium");
wherein the high drug load, stable tablet comprises from about 50% to about 90% of elagolix sodium by weight of the tablet, from about 0.1% to about 20% of a pharmaceutically acceptable meltable binder by weight of the tablet, and a disintegrant selected from the group consisting of cross-linked modified starches, cross-linked polyvinylpyrrolidone, cross-linked carboxymethyl cellulose, and combinations thereof; and
wherein the high drug load, stable tablet controls degradation of elagolix sodium to within pharmaceutically acceptable levels for at least 1 month when said tablet is stored at 40° C./75% relative humidity.

35. The tablet of claim 34, wherein the disintegrant is present in an amount from about 2% to about 8% by weight of the tablet.

36. The tablet of claim 34, wherein the pharmaceutically acceptable meltable binder has a melting point of less than 124° C.

37. The tablet of claim 34, wherein the pharmaceutically acceptable meltable binder is selected from the group consisting of a polyethylene glycol (PEG), a cellulose derivative, a poloxamer, and combinations thereof.

38. The tablet of claim 34, wherein the pharmaceutically acceptable meltable binder is a polyalkylene glycol.

39. The tablet of claim 34, wherein the pharmaceutically acceptable meltable binder is polyethylene glycol 3350.

40. The tablet of claim 34, the tablet comprising:
(a) from about 55% to about 60% by weight of elagolix sodium;
(b) from about 4% to about 6% by weight of the pharmaceutically acceptable meltable binder;
(c) from about 4% to about 6% by weight of the disintegrant;
(d) from about 0.1% to about 2% by weight of a glidant; and
(e) from about 25% to about 35% by weight of a pH modifying agent.

41. A high drug load, stable tablet comprising:
from about 55% to about 60% by weight of sodium 4-((R)-2-[5-(2-fluoro-3-methoxy-phenyl)-3-(2-fluoro-6-trifluoromethyl-benzyl)-4-methyl-2,6-dioxo-3,6-dihydro-2H-pyrimidin-1-yl]-1-phenyl-ethylamino)butanoate ("elagolix sodium"); and
from about 4% to about 6% by weight of a pharmaceutically acceptable meltable binder, wherein the pharmaceutically acceptable meltable binder is selected from the group consisting of polyethylene glycol 3350, hydroxypropylcellulose, poloxamer 188, and combinations thereof,
wherein said high drug load, stable tablet controls degradation of elagolix sodium to within pharmaceutically acceptable levels for at least 1 month when said tablet is stored at 40° C./75% relative humidity.

42. The tablet of claim 41, wherein about 310 mg elagolix sodium is present in the tablet.

43. The tablet of claim 41, wherein the pharmaceutically acceptable meltable binder is polyethylene glycol 3350.

44. The tablet of claim 41, wherein about 310 mg elagolix sodium is present in the tablet and wherein the pharmaceutically acceptable meltable binder is polyethylene glycol 3350.

45. The tablet of claim 41, further comprising a disintegrant, wherein the disintegrant is present in an amount from about 2% to about 8% by weight of the tablet.

46. The tablet of claim 45, wherein the disintegrant is selected from the group consisting of cross-linked modified starches, cross-linked polyvinylpyrrolidone, cross-linked carboxymethyl cellulose, and combinations thereof.

* * * * *

UNITED STATES PATENT AND TRADEMARK OFFICE
CERTIFICATE OF CORRECTION

PATENT NO. : 12,083,227 B2  
APPLICATION NO. : 16/105440  
DATED : September 10, 2024  
INVENTOR(S) : Yihong Qiu et al.

Page 1 of 1

It is certified that error appears in the above-identified patent and that said Letters Patent is hereby corrected as shown below:

On the Title Page

In Column 1, below item (60), insert -- (30) Foreign Application Priority Data
July 23, 2018 (WO) ............. PCT/US2018/043321 --, therefor.

In the Claims

In Column 53, Claim 10, Line 20, delete "claim 9," and insert -- claim 1, --, therefor.

In Column 56, Claim 41, Line 21, delete "thereof," and insert -- thereof; --, therefor.

Signed and Sealed this
Sixteenth Day of September, 2025

Coke Morgan Stewart
*Acting Director of the United States Patent and Trademark Office*